United States Patent
Nagy

(10) Patent No.: US 12,371,695 B2
(45) Date of Patent: Jul. 29, 2025

(54) METHODS AND COMPOSITIONS TO PROMOTE TARGETED GENOME MODIFICATIONS USING HUH ENDONUCLEASES

(71) Applicant: Monsanto Technology LLC, St. Louis, MO (US)

(72) Inventor: Ervin D. Nagy, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 614 days.

(21) Appl. No.: 17/632,435

(22) PCT Filed: Jul. 31, 2020

(86) PCT No.: PCT/US2020/044501
§ 371 (c)(1),
(2) Date: Feb. 2, 2022

(87) PCT Pub. No.: WO2021/025999
PCT Pub. Date: Feb. 11, 2021

(65) Prior Publication Data
US 2022/0282259 A1    Sep. 8, 2022

Related U.S. Application Data

(60) Provisional application No. 62/882,266, filed on Aug. 2, 2019.

(51) Int. Cl.
| | | |
|---|---|---|
| C12N 15/52 | (2006.01) | |
| C12N 15/64 | (2006.01) | |
| C12Q 1/68 | (2018.01) | |
| C12Q 1/6811 | (2018.01) | |

(52) U.S. Cl.
CPC ............. *C12N 15/52* (2013.01); *C12N 15/64* (2013.01); *C12Q 1/6811* (2013.01); *C07K 2319/00* (2013.01); *C12N 2310/20* (2017.05)

(58) Field of Classification Search
CPC .. C12N 15/64; C12N 2310/20; C12Q 1/6811; C07K 2319/00
See application file for complete search history.

(56) References Cited

U.S. PATENT DOCUMENTS

| | | | |
|---|---|---|---|
| 2006/0123505 A1 | 6/2006 | Kikuchi et al. | |
| 2016/0186197 A1 | 6/2016 | Pankratov et al. | |
| 2016/0208243 A1 | 7/2016 | Zhang et al. | |
| 2016/0340395 A1* | 11/2016 | Gordon | C07K 14/4702 |
| 2018/0073012 A1* | 3/2018 | Liu | C12Y 305/04004 |
| 2018/0371497 A1 | 12/2018 | Gill et al. | |
| 2019/0062735 A1 | 2/2019 | Welstead et al. | |
| 2019/0185843 A1 | 6/2019 | Roubos et al. | |
| 2019/0202856 A1* | 7/2019 | Davis | C12N 15/102 |
| 2019/0233814 A1 | 8/2019 | Zhang et al. | |

FOREIGN PATENT DOCUMENTS

| | | | |
|---|---|---|---|
| JP | 2016501532 A | 1/2016 | |
| JP | 2019507599 A | 3/2019 | |
| WO | 2014093635 A1 | 6/2014 | |
| WO | WO-2016103233 A2 * | 6/2016 | ............. C12N 15/11 |
| WO | 2016205711 A1 | 12/2016 | |
| WO | 2017152015 A1 | 9/2017 | |
| WO | WO-2018231999 A1 * | 12/2018 | ............. C12N 15/11 |
| WO | 2019084148 A1 | 5/2019 | |
| WO | 2019104058 A1 | 5/2019 | |

OTHER PUBLICATIONS

Guo et al., 2004, Protein tolerance to random amino acid change. Proceedings of the National Academy of Sciences, 101(25), 9205-9210. (Year: 2004).*
Bagemann et al., 2017, Precise insertion and guided editing of higher plant genomes using Cpf1 CRISPR nucleases. Scientific reports, 7(1), 11606. (Year: 2017).*
Aird, E. J. et al. (May 31, 2018). "Increasing Cas9-Mediated Homology-Directed Repair Efficiency through Covalent Tethering of DNA Repair Template," Communications Biol. 1:54, 6 pages.
Ali, Z. et al. (Jan. 23, 2020). "Fusion of the Cas9 Endonuclease and the VirD2 Relaxase Facilitates Homology-Directed Repair for Precise Genome Engineering in Rice," Communications Biol. 3(1):44, 13 pages.
Anzalone, A. et al. (Dec. 2019). "Search-and-Replace Genome Editing Without Double-Strand Breaks or Donor DNA," Nature 576(7785):149-157.
Chandler, M. et al. (Aug. 2013). "Breaking and Joining Single-Stranded DNA: The HUH Endonuclease Superfamily," Nature Reviews Microbiology 11(8):525-538.
Chen, Y. et al. (Jan. 2014). "High throughput Agrobacterium Tumefaciens-Mediated Germline Transformation of Mechanically Isolated Meristem Explants of Cotton (*Gossypium hirsutum* L.)," Plant Cell Reports 33(1):153-164.
De Boer, H.A. et al. (Jan. 1983). "The Tac Promoter: a Functional Hybrid Derived From the trp and lac Promoters," Proc. Natl. Acad. Sci. U.S.A. 80(1):21-25.
Doring, P. et al. (Feb. 2000). "The Role of AHA Motifs in the Activator Function of Tomato Heat Stress Transcription Factors HsfA1 and HsfA2," Plant Cell 12(2):265-278.
Dostal, L. et al. (2011, e-pub. Nov. 24, 2010). "Tracking F Plasmid TraI Relaxase Processing Reactions Provides Insight into F Plasmid Transfer," Nucleic Acids Res 39(7):2658-2670.

(Continued)

Primary Examiner — David H Kruse
Assistant Examiner — Santosh Sharma
(74) Attorney, Agent, or Firm — Morrison & Foerster LLP

(57) ABSTRACT

This disclosure provides compositions and methods for improving site-directed integration of nucleic acids using RNA-guided nucleases coupled with HUH endonucleases. In one aspect, this disclosure provides a ribonucleoprotein comprising: (a) a re-combinant polypeptid comprising: (i) an amino acid sequence encoding a Cas12a nuclease; (ii) an amino acid sequence encoding a linker; and (iii) an amino acid sequence encoding a HUH nuclease; and (b) at least one guide nucleic acid.

21 Claims, 9 Drawing Sheets
Specification includes a Sequence Listing.

(56) References Cited

OTHER PUBLICATIONS

Gaudelli, N. M. et al. (Nov. 23, 2017). "Programmable Base Editing Of A*T To G*C In Genomic DNA Without DNA Cleavage," Nature 551:464-471.
Gilbert, L.A. et al. (Oct. 23, 2014). "Genome-Scale CRISPR-Mediated Control of Gene Repression and Activation," Cell 159:647-661.
Gu, B. et al. (Aug. 2018). "Efficient Generation of Targeted Large Insertions by Microinjection into Two-Cell-Stage Mouse Embryos," Nature Biotechnology 36(7):632-637.
Hollingshead, S. et al. (Jan. 1985). "Nucleotide Sequence Analysis of a Gene Encoding a Streptomycin/Spectinomycin Adenylyltransferase," Plasmid 13(1):17-30.
International Search Report, dated Nov. 18, 2020, for PCT Application No. PCT/US2020/044501, filed Jul. 31, 2020, 6 pages.
Jinek et al. (Aug. 17, 2012). "A Programmable Dual-RNA-Guided DNA Endonuclease In Adaptive Bacterial Immunity," Science 337(6096):816-821.
Komor, A. C. et al. (May 19, 2016). "Programmable Editing Of a Target Base In Genomic DNA Without Double-Stranded DNA Cleavage," Nature 533:420-424.
Krupovic, M. et al. (Jun. 1, 2020). "Cressdnaviricota: a Virus Phylum Unifying Seven Families of Rep-Encoding Viruses with Single-Stranded, Circular DNA Genomes," Journal of Virology 94(12):e00582-00520, 4 pages.
Li, H. et al. (May 2020). "Precise Modifications of Both Exogenous and Endogenous Genes in Rice by Prime Editing," Mol Plant 13(5):671-674.
Lovendahl, K. N. et al. (May 24, 2017). "Sequence-Directed Covalent Protein-DNA Linkages in a Single Step Using HUH-Tags," J Am Chem Soc. 139(2):7030-7035.
Lowder, L. G. et al. (Oct. 2015). "A CRISPR/Cas9 Toolbox for Multiplexed Plant Genome Editing and Transcriptional Regulation," Plant Physiology 169(2):971-985.
Ma, M. et al. (Mar. 7, 2017). "Efficient Generation of Mice Carrying Homozygous Double-Floxp Alleles Using the Cas9-Avidin/Biotin-donor DNA System," Cell Res 27:578-581.

Savic, N. et al. (May 29, 2018). "Covalent Linkage of the DNA Repair Template to the CRISPR-Cas9 Nuclease Enhances Homology-Directed Repair," Elife 7:e33761, 18 pages.
Schmidt, C. et al. (2019). "DNA Break Repair in Plants and Its Application for Genome Engineering," Methods Mol Biol. 1864:237-266.
Tang, X. et al. (May 4, 2020). "Plant Prime Editors Enable Precise Gene Editing in☐Rice Cells," Mol Plant 13(5):667-670.
Timchenko, T. et al. (Dec. 1999). "A Single Rep Protein Initiates Replication of Multiple Genome Components of Faba Bean Necrotic Yellows Virus, a Single-Stranded DNA Virus of Plants," J. of Virol. 73(12):10173-10182.
Van Eck, J. (Sep. 18, 2020). "Applying Gene Editing to Tailor Precise Genetic Modifications in Plants," Journal of Biological Chemistry 295(38):13267-13276.
Vega-Rocha, S. et al. (May 2, 2007). "Solution Structure of the Endonuclease Domain from the Master Replication Initiator Protein of the Nanovirus Faba Bean Necrotic Yellows Virus and Comparison with the Corresponding Geminivirus and Circovirus Structures," Biochemistry 46(21):6201-6212.
Ye, X. et al. (Aug. 2011). "Enhanced Production of Single Copy Backbone-Free Transgenic Plants in Multiple Crop Species using Binary Vectors with a PRi Replication Origin in *Agrobacterium tumefaciens*," Transgenic Research 20(4):773-786.
Zetsche, B. et al. (Oct. 22, 2015). "Cpf1 Is A Single RNA-Guided Endonuclease Of A Class 2 CRISPR-Cas System," Cell 163:759-771.
Zong, Y. et al. (Feb. 27, 2017). "Precise Base Editing in Rice, Wheat and Maize with a Cas9-Cytidine Deaminase Fusion," Nature Biotechnology 35:438-440.
Nagy, E. D. et al. (Aug. 2022, e-pub. Jun. 19, 2022). "Site-directed Integration of Exogenous DNA into the Soybean Genome by LbCas12a Fused to a Plant Viral HUH Endonuclease," The Plant Journal 111(3):905-916.
Zhang, Y. et al. (Aug. 2019, e-pub. Jul. 15, 2019). "The Emerging and Uncultivated Potential of CRISPR technology in Plant Science," Nat Plants 5(8):778-794, 17 pages.

* cited by examiner

SEQUENCE LISTING

<160> NUMBER OF SEQ ID NOS: 28

<210> SEQ ID NO 1
<211> LENGTH: 1227
<212> TYPE: PRT
<213> ORGANISM: Artificial Sequence
<220> FEATURE:
<223> OTHER INFORMATION: Synthetic sequence. Cys-free LbCas12a

<400> SEQUENCE: 1

Ser Lys Leu Glu Lys Phe Thr Asn Leu Tyr Ser Leu Ser Lys Thr Leu
1               5                   10                  15

Arg Phe Lys Ala Ile Pro Val Gly Lys Thr Gln Glu Asn Ile Asp Asn
            20                  25                  30

Lys Arg Leu Leu Val Glu Asp Glu Lys Arg Ala Glu Asp Tyr Lys Gly
        35                  40                  45

Val Lys Lys Leu Leu Asp Arg Tyr Tyr Leu Ser Phe Ile Asn Asp Val
    50                  55                  60

Leu His Ser Ile Lys Leu Lys Asn Leu Asn Asn Tyr Ile Ser Leu Phe
65                  70                  75                  80

Arg Lys Lys Thr Arg Thr Glu Lys Glu Asn Lys Glu Leu Glu Asn Leu
                85                  90                  95

Glu Ile Asn Leu Arg Lys Glu Ile Ala Lys Ala Phe Lys Gly Asn Glu
            100                 105                 110

Gly Tyr Lys Ser Leu Phe Lys Lys Asp Ile Ile Glu Thr Ile Leu Pro
        115                 120                 125

Glu Phe Leu Asp Asp Lys Asp Glu Ile Ala Leu Val Asn Ser Phe Asn
    130                 135                 140

```
Gly Phe Thr Thr Ala Phe Thr Gly Phe Phe Asp Asn Arg Glu Asn Met
145                 150                 155                 160

Phe Ser Glu Glu Ala Lys Ser Thr Ser Ile Ala Phe Arg Ile Ile Asn
                165                 170                 175

Glu Asn Leu Thr Arg Tyr Ile Ser Asn Met Asp Ile Phe Glu Lys Val
            180                 185                 190

Asp Ala Ile Phe Asp Lys His Glu Val Gln Glu Ile Lys Glu Lys Ile
        195                 200                 205

Leu Asn Ser Asp Tyr Asp Val Glu Asp Phe Phe Gly Glu Phe Phe
    210                 215                 220

Asn Phe Val Leu Thr Gln Glu Gly Ile Asp Val Tyr Asn Ala Ile Ile
225                 230                 235                 240

Gly Gly Phe Val Thr Glu Ser Gly Glu Lys Ile Lys Gly Leu Asn Glu
                245                 250                 255

Tyr Ile Asn Leu Tyr Asn Gln Lys Thr Lys Gln Lys Leu Pro Lys Phe
                260                 265                 270

Lys Pro Leu Tyr Lys Gln Val Leu Ser Asp Arg Glu Ser Leu Ser Phe
            275                 280                 285

Tyr Gly Glu Gly Tyr Thr Ser Asp Glu Glu Val Leu Glu Val Phe Arg
290                 295                 300

Asn Thr Leu Asn Lys Asn Ser Glu Ile Phe Ser Ser Ile Lys Lys Leu
305                 310                 315                 320

Glu Lys Leu Phe Lys Asn Phe Asp Glu Tyr Ser Ser Ala Gly Ile Phe
                325                 330                 335

Val Lys Asn Gly Pro Ala Ile Ser Thr Ile Ser Lys Asp Ile Phe Gly
            340                 345                 350

Glu Trp Asn Val Ile Arg Asp Lys Trp Asn Ala Glu Tyr Asp Asp Ile
            355                 360                 365

His Leu Lys Lys Lys Ala Val Val Thr Glu Lys Tyr Glu Asp Asp Arg
    370                 375                 380

Arg Lys Ser Phe Lys Lys Ile Gly Ser Phe Ser Leu Glu Gln Leu Gln
385                 390                 395                 400

Glu Tyr Ala Asp Ala Asp Leu Ser Val Val Glu Lys Leu Lys Glu Ile
                405                 410                 415

Ile Ile Gln Lys Val Asp Glu Ile Tyr Lys Val Tyr Gly Ser Ser Glu
            420                 425                 430

Lys Leu Phe Asp Ala Asp Phe Val Leu Glu Lys Ser Leu Lys Lys Asn
        435                 440                 445

Asp Ala Val Val Ala Ile Met Lys Asp Leu Leu Asp Ser Val Lys Ser
450                 455                 460

Phe Glu Asn Tyr Ile Lys Ala Phe Phe Gly Glu Gly Lys Glu Thr Asn
465                 470                 475                 480

Arg Asp Glu Ser Phe Tyr Gly Asp Phe Val Leu Ala Tyr Asp Ile Leu
                485                 490                 495

Leu Lys Val Asp His Ile Tyr Asp Ala Ile Arg Asn Tyr Val Thr Gln
            500                 505                 510

Lys Pro Tyr Ser Lys Asp Lys Phe Lys Leu Tyr Phe Gln Asn Pro Gln
        515                 520                 525

Phe Met Gly Gly Trp Asp Lys Asp Lys Glu Thr Asp Tyr Arg Ala Thr
            530                 535                 540

Ile Leu Arg Tyr Gly Ser Lys Tyr Tyr Leu Ala Ile Met Asp Lys Lys
545                 550                 555                 560

Tyr Ala Lys Ser Leu Gln Lys Ile Asp Lys Asp Asp Val Asn Gly Asn
```

-continued

```
                565                 570                 575
Tyr Glu Lys Ile Asn Tyr Lys Leu Leu Pro Gly Pro Asn Lys Met Leu
                580                 585                 590

Pro Lys Val Phe Phe Ser Lys Lys Trp Met Ala Tyr Tyr Asn Pro Ser
                595                 600                 605

Glu Asp Ile Gln Lys Ile Tyr Lys Asn Gly Thr Phe Lys Lys Gly Asp
            610                 615                 620

Met Phe Asn Leu Asn Asp Leu His Lys Leu Ile Asp Phe Phe Lys Asp
625                 630                 635                 640

Ser Ile Ser Arg Tyr Pro Lys Trp Ser Asn Ala Tyr Asp Phe Asn Phe
                645                 650                 655

Ser Glu Thr Glu Lys Tyr Lys Asp Ile Ala Gly Phe Tyr Arg Glu Val
                660                 665                 670

Glu Glu Gln Gly Tyr Lys Val Ser Phe Glu Ser Ala Ser Lys Lys Glu
                675                 680                 685

Val Asp Lys Leu Val Glu Glu Gly Lys Leu Tyr Met Phe Gln Ile Tyr
            690                 695                 700

Asn Lys Asp Phe Ser Asp Lys Ser His Gly Thr Pro Asn Leu His Thr
705                 710                 715                 720

Met Tyr Phe Lys Leu Leu Phe Asp Glu Asn Asn His Gly Gln Ile Arg
                725                 730                 735

Leu Ser Gly Gly Ala Glu Leu Phe Met Arg Arg Ala Ser Leu Lys Lys
                740                 745                 750

Glu Glu Leu Val Val His Pro Ala Asn Ser Pro Ile Ala Asn Lys Asn
                755                 760                 765

Pro Asp Asn Pro Lys Lys Thr Thr Thr Leu Ser Tyr Asp Val Tyr Lys
            770                 775                 780

Asp Lys Arg Phe Ser Glu Asp Gln Tyr Glu Leu His Ile Pro Ile Ala
785                 790                 795                 800

Ile Asn Lys Ala Pro Lys Asn Ile Phe Lys Ile Asn Thr Glu Val Arg
                805                 810                 815

Val Leu Leu Lys His Asp Asp Asn Pro Tyr Val Ile Gly Ile Asp Arg
            820                 825                 830

Gly Glu Arg Asn Leu Leu Tyr Ile Val Val Val Asp Gly Lys Gly Asn
            835                 840                 845

Ile Val Glu Gln Tyr Ser Leu Asn Glu Ile Ile Asn Asn Phe Asn Gly
850                 855                 860

Ile Arg Ile Lys Thr Asp Tyr His Ser Leu Leu Asp Lys Lys Glu Lys
865                 870                 875                 880

Glu Arg Phe Glu Ala Arg Gln Asn Trp Thr Ser Ile Glu Asn Ile Lys
                885                 890                 895

Glu Leu Lys Ala Gly Tyr Ile Ser Gln Val Val His Lys Ile Val Glu
                900                 905                 910

Leu Val Glu Lys Tyr Asp Ala Val Ile Ala Leu Glu Asp Leu Asn Ser
            915                 920                 925

Gly Phe Lys Asn Ser Arg Val Lys Val Glu Lys Gln Val Tyr Gln Lys
            930                 935                 940

Phe Glu Lys Met Leu Ile Asp Lys Leu Asn Tyr Met Val Asp Lys Lys
945                 950                 955                 960

Ser Asn Pro Ser Ala Thr Gly Gly Ala Leu Lys Gly Tyr Gln Ile Thr
                965                 970                 975

Asn Lys Phe Glu Ser Phe Lys Ser Met Ser Thr Gln Asn Gly Phe Ile
                980                 985                 990
```

```
Phe Tyr Ile Pro Ala Trp Leu Thr Ser Lys Ile Asp Pro Ser Thr Gly
        995                 1000                1005

Phe Val Asn Leu Leu Lys Thr Lys Tyr Thr Ser Ile Ala Asp Ser
    1010                1015                1020

Lys Lys Phe Ile Ser Ser Phe Asp Arg Ile Met Tyr Val Pro Glu
    1025                1030                1035

Glu Asp Leu Phe Glu Phe Ala Leu Asp Tyr Lys Asn Phe Ser Arg
    1040                1045                1050

Thr Asp Ala Asp Tyr Ile Lys Lys Trp Lys Leu Tyr Ser Tyr Gly
    1055                1060                1065

Asn Arg Ile Arg Ile Phe Arg Asn Pro Lys Lys Asn Asn Val Phe
    1070                1075                1080

Asp Trp Glu Glu Val Pro Leu Thr Ser Ala Tyr Lys Glu Leu Phe
    1085                1090                1095

Asn Lys Tyr Gly Ile Asn Tyr Gln Gln Gly Asp Ile Arg Ala Leu
    1100                1105                1110

Leu Leu Glu Gln Ser Asp Lys Ala Phe Tyr Ser Ser Phe Met Ala
    1115                1120                1125

Leu Met Ser Leu Met Leu Gln Met Arg Asn Ser Ile Thr Gly Arg
    1130                1135                1140

Thr Asp Val Asp Phe Leu Ile Ser Pro Val Lys Asn Ser Asp Gly
    1145                1150                1155

Ile Phe Tyr Asp Ser Arg Asn Tyr Glu Ala Gln Glu Asn Ala Ile
    1160                1165                1170

Leu Pro Lys Asn Ala Asp Ala Asn Gly Ala Tyr Asn Ile Ala Arg
    1175                1180                1185

Lys Val Leu Trp Ala Ile Gly Gln Phe Lys Lys Ala Glu Asp Glu
    1190                1195                1200

Lys Leu Asp Lys Val Lys Ile Ala Ile Ser Asn Lys Glu Trp Leu
    1205                1210                1215

Glu Tyr Ala Gln Thr Ser Val Lys His
    1220                1225

<210> SEQ ID NO 2
<211> LENGTH: 98
<212> TYPE: PRT
<213> ORGANISM: Faba bean necrosis yellow virus
<220> FEATURE:
<223> OTHER INFORMATION: FBNYV HUH Endonuclease

<400> SEQUENCE: 2

Met Ala Arg Gln Val Ile Cys Trp Cys Phe Thr Leu Asn Asn Pro Leu
1               5                   10                  15

Ser Pro Leu Ser Leu His Asp Ser Met Lys Tyr Leu Val Tyr Gln Thr
                20                  25                  30

Glu Gln Gly Glu Ala Gly Asn Ile His Phe Gln Gly Tyr Ile Glu Met
            35                  40                  45

Lys Lys Arg Thr Ser Leu Ala Gly Met Lys Lys Leu Ile Pro Gly Ala
        50                  55                  60

His Phe Glu Lys Arg Arg Gly Thr Gln Gly Glu Ala Arg Ala Tyr Ser
65                  70                  75                  80

Met Lys Glu Asp Thr Arg Leu Glu Gly Pro Trp Glu Tyr Gly Glu Phe
                85                  90                  95

Val Pro
```

<210> SEQ ID NO 3
<211> LENGTH: 16
<212> TYPE: PRT
<213> ORGANISM: Artificial Sequence
<220> FEATURE:
<223> OTHER INFORMATION: Synthetic sequence. Linker

<400> SEQUENCE: 3

Ser Ala Ser Asp Thr Gly Gly Ser Ser Glu Thr Gly Thr Leu Asp Ser
1               5                   10                  15

<210> SEQ ID NO 4
<211> LENGTH: 3681
<212> TYPE: DNA
<213> ORGANISM: Artificial Sequence
<220> FEATURE:
<223> OTHER INFORMATION: Synthetic sequence. Cys-free LbCas12a

<400> SEQUENCE: 4

| | | | | | |
|---|---|---|---|---|---|
| agcaaactgg | aaaaattcac | caacctgtac | tccctgagca | aaaccctgcg | cttcaaagcg | 60 |
| atcccggttg | gtaaaaccca | ggaaaacatc | gataacaagc | gcctcctggt | cgaagacgag | 120 |
| aaacgcgcag | aggactacaa | aggcgtcaaa | aagctgctcg | atcgctacta | cctgagcttc | 180 |
| atcaacgatg | tgttgcacag | catcaaactg | aagaacctga | caactacat | cagcctgttc | 240 |
| cgcaagaaaa | cccgtaccga | aaagagaac | aaagaactgg | aaaacctgga | aattaacctg | 300 |
| cgtaaagaaa | tcgctaaagc | gttcaaaggt | aacgagggct | acaaatctct | gttcaaaaag | 360 |
| gacatcatcg | aaaccatcct | gccggaattt | ctggatgaca | agatgaaat | cgcgctggtg | 420 |
| aactcgttca | acggcttcac | gaccgcgttc | acgggttct | tcgacaaccg | cgagaacatg | 480 |
| tttagcgagg | aagcgaaaag | caccagcatc | gccttccgta | tcatcaacga | aaacctgacc | 540 |
| cgctacatca | gcaacatgga | catttccgag | aaggttgacg | ctatctttga | caaacacgag | 600 |
| gttcaggaga | tcaaggagaa | atcctgaac | agcgactacg | atgtggaaga | cttcttcgaa | 660 |
| ggcgagttct | tcaacttcgt | tctgacccaa | gagggcatcg | acgtttacaa | cgccatcatt | 720 |
| ggcggcttcg | taaccgaaag | cggtgaaaag | atcaaagggc | tgaacgagta | tatcaacctg | 780 |
| tataaccaga | aaccaaaca | gaaactgccg | aaattcaagc | cgctgtacaa | gcaggttctg | 840 |
| tccgaccgcg | agagcctgag | cttctatggc | gagggctaca | cgtccgacga | ggaagtgctc | 900 |
| gaagtcttcc | gcaacaccct | gaacaagaac | agcgagatct | ctcgtccat | caaaagctg | 960 |
| gagaaactgt | tcaagaactt | cgacgagtac | tcttctgcgg | gcatcttcgt | gaaaaacggc | 1020 |
| ccggccatca | gcacgatttc | caaggatatc | tttggcgagt | ggaacgtgat | ccgcgacaaa | 1080 |
| tggaacgctg | aatacgacga | catccatctg | aagaagaagg | cggtcgttac | cgaaaaatac | 1140 |
| gaagatgacc | gccgcaagtc | ttttaaaaag | atcggctcgt | tcagcctgga | gcagctgcag | 1200 |
| gaatacgcgg | acgctgactt | gagcgtggtc | gagaaactga | agagatcat | catccagaag | 1260 |
| gtcgacgaaa | tctacaaagt | gtacggcagt | agcgaaaaac | tgttcgacgc | tgatttcgtc | 1320 |
| ctggaaaaga | gcctgaaaaa | gaacgacgcg | gtggtggcga | tcatgaagga | cctgctggac | 1380 |
| agcgttaagt | cgttcgaaaa | ctacattaaa | gcgttttcg | gggaaggcaa | agaaaccaac | 1440 |
| cgcgacgaat | cttttacgg | tgactttgtc | ctcgcctacg | acatcctgct | caaagtcgac | 1500 |
| cacatctatg | acgctatccg | caactacgtg | acccagaagc | cgtacagcaa | agacaaattc | 1560 |
| aagctgtact | tccagaaccc | ccagttcatg | ggcggctggg | ataaggacaa | ggaaaccgac | 1620 |
| taccgcgcca | ccatcctgcg | ctacggtagc | aaatattacc | tggcgatcat | ggacaaaaaa | 1680 |

-continued

```
tacgccaaat ctttgcagaa aatcgacaag gacgacgtga acggtaacta cgaaaaaatt   1740
aactataaac tgctgccggg tccgaacaaa atgctgccga aagtgttctt cagcaaaaaa   1800
tggatggcat actacaaccc gtctgaagat attcagaaaa tctacaaaaa cggcaccttc   1860
aaaaaaggtg atatgttcaa cctgaacgat ctgcacaaac tgattgattt cttcaaggac   1920
tcgatctctc gttatccgaa atggtctaac gcgtacgact tcaacttcag cgaaaccgaa   1980
aaatacaaag atatcgcggg tttctatcgt gaagttgaag aacagggcta caaagtgtct   2040
ttcgaatccg cgtccaaaaa ggaagtggat aaactggtcg aagaaggtaa actgtacatg   2100
ttccagatct ataacaaaga cttcagcgat aaatcccatg gcacccccgaa cctgcacacc   2160
atgtacttca aactgctgtt cgatgaaaac aaccacggcc agatccgtct gtccggcggt   2220
gcagaactgt ttatgcgccg tgcgtccctg aaaaaagaag agctggtagt acatccggca   2280
aactctccga tcgctaacaa aaacccggac aacccgaaga aaaccaccac cctgagctat   2340
gatgtatata aagataaacg tttctccgaa gatcagtacg aactgcacat cccgatcgca   2400
attaacaaag cgccgaaaaa catcttcaaa atcaacaccg aagtgcgtgt tctgctgaaa   2460
cacgatgata acccgtacgt tattggcatc gaccgtggcg aacgtaacct gctgtacatc   2520
gttgtggttg acggtaaagg taacattgtg gaacagtata gcctgaacga aatcattaac   2580
aacttcaacg gtatccgtat caaaaccgat tatcacagcc tgctggataa aaaagaaaaa   2640
gaacgttttg aagcgcgtca gaactggacc agcatcgaaa acatcaaaga actgaaagcg   2700
ggctacatct cgcaggttgt tcacaaaatc gtggaactgg ttgaaaaata cgatgcagtt   2760
atcgcgctgg aagatctgaa cagcggtttc aaaaactcac gtgtaaaagt tgaaaaacag   2820
gtttaccaga aattcgaaaa aatgctgatt gataaactga actatatggt ggataaaaaa   2880
tctaacccga gcgcgactgg tggcgcactg aaaggctatc agatcaccaa caagttcgag   2940
agcttcaaaa gcatgagcac ccagaacggt ttcatcttct atatcccggc ctggctgacc   3000
tctaaaattg acccgagcac tggcttcgtg aacctgctga aaaccaaata cactagcatc   3060
gctgacagca aaaaattcat ctcctccttt gaccgtatca tgtacgtgcc ggaagaagac   3120
ctgttcgaat ttgcactgga ttacaaaaac ttctcccgca ctgacgccga ctatattaaa   3180
aaatggaaac tgtactctta tggtaaccgt atccgtatct tccgtaaccc gaagaaaaac   3240
aacgttttcg attgggaaga agtgccgctg accagcgcgt ataaagaact gttcaacaaa   3300
tacggcatta actaccagca gggcgacatt cgtgcgctgc tgctggaaca gtccgataaa   3360
gcgttctaca gctccttcat ggcactgatg tccctgatgc tgcagatgcg taacagcatt   3420
actggccgta ccgatgtgga tttcctgatc agcccggtta aaaactctga cggcatcttt   3480
tacgacagcc gtaactacga agcgcaggaa aacgcgattc tgccgaaaaa cgcggacgct   3540
aacggcgcat acaacatcgc acgtaaagtg ctgtgggcga tcggtcagtt caaaaaagcg   3600
gaagatgaaa aactggataa agtgaaaatc gcgatcagca acaaagaatg gctggaatac   3660
gcgcagacca gcgttaaaca c                                            3681
```

<210> SEQ ID NO 5
<211> LENGTH: 294
<212> TYPE: DNA
<213> ORGANISM: Artificial Sequence
<220> FEATURE:
<223> OTHER INFORMATION: Synthetic sequence. FBNYV HUH.

<400> SEQUENCE: 5

```
atggcgcgcc aggtgatttg ctggtgcttt accctgaaca acccgctgag cccgctgagc     60
```
ctgcatgata gcatgaaata tctggtgtat cagaccgaac agggcgaagc gggcaacatt      120
cattttcagg gctatattga aatgaaaaaa cgcaccagcc tggcgggcat gaaaaaactg      180
attccgggcg cgcattttga aaaacgccgc ggcacccagg gcgaagcgcg cgcgtatagc      240
atgaaagaag atacccgcct ggaaggcccg tgggaatatg gcgaatttgt gccg            294

<210> SEQ ID NO 6
<211> LENGTH: 48
<212> TYPE: DNA
<213> ORGANISM: Artificial Sequence
<220> FEATURE:
<223> OTHER INFORMATION: Synthetic sequence. Linker.

<400> SEQUENCE: 6
tctgcttctg atactggtgg ttcttctgaa actggtactt tagattct                   48

<210> SEQ ID NO 7
<211> LENGTH: 4023
<212> TYPE: DNA
<213> ORGANISM: Artificial Sequence
<220> FEATURE:
<223> OTHER INFORMATION: Synthetic sequence. Cys-free
    LbCas12a:linker:FBNYV

<400> SEQUENCE: 7
agcaaactgg aaaaattcac caacctgtac tccctgagca aaaccctgcg cttcaaagcg      60
atcccggttg gtaaaaccca ggaaaacatc gataacaagc gcctcctggt cgaagacgag     120 aaaacgcgcag aggactacaa aggcgtcaaa agctgctcg atcgctacta cctgagcttc     180
atcaacgatg tgttgcacag catcaaactg aagaacctga caactacat cagcctgttc     240 cgcaagaaaa cccgtaccga aaagagaac aaagaactgg aaaacctgga attaacctg      300 cgtaaagaaa tcgctaaagc gttcaaaggt aacgagggct acaaatctct gttcaaaaag     360
gacatcatcg aaaccatcct gccggaattt ctggatgaca agatgaaat cgcgctggtg     420 aactcgttca acggcttcac gaccgcgttc acgggttct cgacaaccg cgagaacatg      480 tttagcgagg agcgaaaag caccagcatc gccttccgta tcatcaacga aaacctgacc     540
cgctacatca gcaacatgga cattttcgag aaggttgacg ctatctttga caaacacgag     600
gttcaggaga tcaaggagaa atcctgaac agcgactacg atgtggaaga cttcttcgaa      660
ggcgagttct tcaacttcgt tctgacccaa gagggcatcg acgtttacaa cgccatcatt     720
ggcggcttcg taaccgaaag cggtgaaaag atcaaaggc tgaacgagta tatcaacctg     780
tataaccaga aaccaaaca gaaactgccg aaattcaagc cgctgtacaa gcaggttctg     840
tccgaccgcg agagcctgag cttctatggc gagggctaca cgtccgacga ggaagtgctc     900
gaagtcttcc gcaacaccct gaacaagaac agcgagatct tctcgtccat caaaaagctg     960
gagaaactgt tcaagaactt cgacgagtac tcttctgcgg gcatcttcgt gaaaaacggc    1020
ccggccatca gcacgatttc caaggatatc tttggcgagt ggaacgtgat ccgcgacaaa    1080
tggaacgctg aatacgacga catccatctg aagaagaagg cggtcgttac gaaaaatac    1140 gaagatgacc gccgcaagtc ttttaaaag atcggctcgt tcagcctgga gcagctgcag    1200
gaatacgcgg acgctgactt gagcgtggtc gagaaactga aagagatcat catccagaag    1260
gtcgacgaaa tctacaaagt gtacggcagt agcgaaaaac tgttcgacgc tgatttcgtc    1320
ctggaaaaga gcctgaaaaa gaacgacgcg gtggtggcgc tcatgaagga cctgctggac    1380
agcgttaagt cgttcgaaaa ctacattaaa gcgttttcg gggaaggcaa agaaaccaac    1440

```
cgcgacgaat cttttacgg tgactttgtc ctcgcctacg acatcctgct caaagtcgac   1500
cacatctatg acgctatccg caactacgtg acccagaagc cgtacagcaa agacaaattc   1560
aagctgtact tccagaaccc ccagttcatg ggcggctggg ataaggacaa ggaaaccgac   1620
taccgcgcca ccatcctgcg ctacggtagc aaatattacc tggcgatcat ggacaaaaaa   1680
tacgccaaat ctttgcagaa atcgacaag gacgacgtga acggtaacta cgaaaaaatt   1740
aactataaac tgctgccggg tccgaacaaa atgctgccga agtgttctt cagcaaaaaa   1800 tggatggcat actacaaccc gtctgaagat attcagaaaa tctacaaaaa cggcaccttc   1860
aaaaaaggtg atatgttcaa cctgaacgat ctgcacaaac tgattgattt cttcaaggac   1920
tcgatctctc gttatccgaa atggtctaac gcgtacgact caacttcag cgaaaccgaa   1980 aaatacaaag atatcgcggg tttctatcgt gaagttgaag aacagggcta caaagtgtct   2040
ttcgaatccg cgtccaaaaa ggaagtggat aaactggtcg aagaaggtaa actgtacatg   2100
ttccagatct ataacaaaga cttcagcgat aaatcccatg gcaccccgaa cctgcacacc   2160
atgtacttca aactgctgtt cgatgaaaac aaccacggcc agatccgtct gtccggcggt   2220
gcagaactgt tatgcgccg tgcgtccctg aaaaagaag agctggtagt acatccggca   2280
aactctccga tcgctaacaa aaacccggac aacccgaaga aaaccaccac cctgagctat   2340
gatgtatata agataaacg ttttctccgaa gatcagtacg aactgcacat cccgatcgca   2400
attaacaaag cgccgaaaaa catcttcaaa atcaacaccg aagtgcgtgt tctgctgaaa   2460
cacgatgata cccgtacgt tattggcatc gaccgtggcg aacgtaacct gctgtacatc   2520
gttgtggttg acggtaaagg taacattgtg aacagtata gcctgaacga atcattaac   2580 aacttcaacg gtatccgtat caaaaccgat tatcacagcc tgctggataa aaagagaaaa   2640
gaacgttttg aagcgcgtca gaactggacc agcatcgaaa acatcaaaga actgaaagcg   2700
ggctacatct cgcaggttgt tcacaaaatc gtggaactgg ttgaaaaata cgatgcagtt   2760
atcgcgctgg aagatctgaa cagcggtttc aaaaactcac gtgtaaaagt tgaaaaacag   2820
gtttaccaga aattcgaaaa aatgctgatt gataaactga actatatggt ggataaaaaa   2880
tctaacccga gcgcgactgg tggcgcactg aaaggctatc agatcaccaa caagttcgag   2940
agcttcaaaa gcatgagcac ccagaacggt ttcatcttct atatcccggc ctggctgacc   3000
tctaaaattg acccgagcac tggcttcgtg aacctgctga aaccaaata cactagcatc   3060 gctgacagca aaaaattcat ctcctccttt gaccgtatca tgtacgtgcc ggaagaagac   3120
ctgttcgaat ttgcactgga ttacaaaaac ttctcccgca ctgacgccga ctatattaaa   3180
aaatggaaac tgtactctta tggtaaccgt atccgtatct tccgtaaccc gaagaaaaac   3240
aacgttttcg attgggaaga agtgccgctg accagcgcgt ataaagaact gttcaacaaa   3300
tacggcatta actaccagca gggcgacatt cgtgcgctgc tgctggaaca gtccgataaa   3360
gcgttctaca gctccttcat ggcactgatg tccctgatgc tgcagatgcg taacagcatt   3420
actggccgta ccgatgtgga tttcctgatc agcccggtta aaaactctga cggcatcttt   3480
tacgacagcc gtaactacga agcgcaggaa aacgcgattc tgccgaaaaa cgcggacgct   3540
aacggcgcat acaacatcgc acgtaaagtg ctgtgggcga tcggtcagtt caaaaaagcg   3600
gaagatgaaa aactggataa agtgaaaatc gcgatcagca caaagaatg gctggaatac   3660 gcgcagacca gcgttaaaca ctctgcttct gatactggtg gttcttctga aactggtact   3720
ttagattcta tggcgcgcca ggtgatttgc tggtgctta ccctgaacaa cccgctgagc   3780
```

```
ccgctgagcc tgcatgatag catgaaatat ctggtgtatc agaccgaaca gggcgaagcg    3840
ggcaacattc attttcaggg ctatattgaa atgaaaaaac gcaccagcct ggcgggcatg    3900
aaaaaactga ttccgggcgc gcattttgaa aaacgccgcg gcacccaggg cgaagcgcgc    3960
gcgtatagca tgaaagaaga tacccgcctg gaaggcccgt gggaatatgg cgaatttgtg    4020
ccg                                                                  4023

<210> SEQ ID NO 8
<211> LENGTH: 30
<212> TYPE: DNA
<213> ORGANISM: Solanum tuberosum
<220> FEATURE:
<223> OTHER INFORMATION: Nuclear localization signal

<400> SEQUENCE: 8
ggtagcaaaa agaggcgtat caagcaggac                                     30

<210> SEQ ID NO 9
<211> LENGTH: 30
<212> TYPE: DNA
<213> ORGANISM: Lycopersicon esculentum
<220> FEATURE:
<223> OTHER INFORMATION: Nuclear localization signal

<400> SEQUENCE: 9
ggatctaaga agcgtaggat caagcaagat                                     30

<210> SEQ ID NO 10
<211> LENGTH: 36
<212> TYPE: DNA
<213> ORGANISM: Artificial Sequence
<220> FEATURE:
<223> OTHER INFORMATION: Synthetic sequence. HIS tag.

<400> SEQUENCE: 10
atgggcagca gccatcatca ccaccatcac catatg                              36

<210> SEQ ID NO 11
<211> LENGTH: 28
<212> TYPE: DNA
<213> ORGANISM: Escherichia coli
<220> FEATURE:
<223> OTHER INFORMATION: P.Ec.tac promoter

<400> SEQUENCE: 11
ttgacaatta atcatcggct cgtataat                                       28

<210> SEQ ID NO 12
<211> LENGTH: 15
<212> TYPE: DNA
<213> ORGANISM: Porcine circovirus
<220> FEATURE:
<223> OTHER INFORMATION: HUH ori polynucleotide

<400> SEQUENCE: 12
aagtattacc agaaa                                                     15

<210> SEQ ID NO 13
<211> LENGTH: 348
<212> TYPE: DNA
<213> ORGANISM: Artificial Sequence
<220> FEATURE:
<223> OTHER INFORMATION: Synthetic sequence. PCV HUH Endonuclease (PCV)

<400> SEQUENCE: 13
```

-continued

```
agcccgagca aaaaaaacgg ccgcagcggc ccgcagccgc ataaacgctg ggtgtttacc        60
ctgaacaacc cgagcgaaga tgaacgcaaa aaaattcgcg atctgccgat tagcctgttt       120
gattatttta ttgtgggcga agaaggcaac gaagaaggcc gcaccccgca tctgcagggc       180
tttgcgaact ttgtgaaaaa acagacccct aacaaagtga atggtatctg ggcgcgcgc       240 tgccatattg aaaaagcgaa aggcaccgat cagcagaaca agaatattg cagcaaagaa       300 ggcaacctgc tgatggaatg cggcgcgccg cgcagccagg ccagcgc                     348
```

<210> SEQ ID NO 14
<211> LENGTH: 116
<212> TYPE: PRT
<213> ORGANISM: Porcine circovirus
<220> FEATURE:
<223> OTHER INFORMATION: PCV HUH

<400> SEQUENCE: 14

```
Ser Pro Ser Lys Lys Asn Gly Arg Ser Gly Pro Gln Pro His Lys Arg
 1               5                  10                  15

Trp Val Phe Thr Leu Asn Asn Pro Ser Glu Asp Glu Arg Lys Lys Ile
            20                  25                  30

Arg Asp Leu Pro Ile Ser Leu Phe Asp Tyr Phe Ile Val Gly Glu Glu
        35                  40                  45

Gly Asn Glu Glu Gly Arg Thr Pro His Leu Gln Gly Phe Ala Asn Phe
    50                  55                  60

Val Lys Lys Gln Thr Phe Asn Lys Val Lys Trp Tyr Leu Gly Ala Arg
65                  70                  75                  80

Cys His Ile Glu Lys Ala Lys Gly Thr Asp Gln Gln Asn Lys Glu Tyr
                85                  90                  95

Cys Ser Lys Glu Gly Asn Leu Leu Met Glu Cys Gly Ala Pro Arg Ser
            100                 105                 110

Gln Gly Gln Arg
        115
```

<210> SEQ ID NO 15
<211> LENGTH: 1299
<212> TYPE: PRT
<213> ORGANISM: Francisella novicida
<220> FEATURE:
<223> OTHER INFORMATION: FnCas12a

<400> SEQUENCE: 15

```
Ser Ile Tyr Gln Glu Phe Val Asn Lys Tyr Ser Leu Ser Lys Thr Leu
 1               5                  10                  15

Arg Phe Glu Leu Ile Pro Gln Gly Lys Thr Leu Glu Asn Ile Lys Ala
            20                  25                  30

Arg Gly Leu Ile Leu Asp Asp Glu Lys Arg Ala Lys Asp Tyr Lys Lys
        35                  40                  45

Ala Lys Gln Ile Ile Asp Lys Tyr His Gln Phe Phe Ile Glu Glu Ile
    50                  55                  60

Leu Ser Ser Val Cys Ile Ser Glu Asp Leu Leu Gln Asn Tyr Ser Asp
65                  70                  75                  80

Val Tyr Phe Lys Leu Lys Lys Ser Asp Asp Asp Asn Leu Gln Lys Asp
                85                  90                  95

Phe Lys Ser Ala Lys Asp Thr Ile Lys Lys Gln Ile Ser Glu Tyr Ile
            100                 105                 110

Lys Asp Ser Glu Lys Phe Lys Asn Leu Phe Asn Gln Asn Leu Ile Asp
```

```
            115                 120                 125
Ala Lys Lys Gly Gln Glu Ser Asp Leu Ile Leu Trp Leu Lys Gln Ser
130                 135                 140

Lys Asp Asn Gly Ile Glu Leu Phe Lys Ala Asn Ser Asp Ile Thr Asp
145                 150                 155                 160

Ile Asp Glu Ala Leu Glu Ile Ile Lys Ser Phe Lys Gly Trp Thr Thr
                165                 170                 175

Tyr Phe Lys Gly Phe His Glu Asn Arg Lys Asn Val Tyr Ser Ser Asn
            180                 185                 190

Asp Ile Pro Thr Ser Ile Ile Tyr Arg Ile Val Asp Asp Asn Leu Pro
        195                 200                 205

Lys Phe Leu Glu Asn Lys Ala Lys Tyr Glu Ser Leu Lys Asp Lys Ala
210                 215                 220

Pro Glu Ala Ile Asn Tyr Glu Gln Ile Lys Lys Asp Leu Ala Glu Glu
225                 230                 235                 240

Leu Thr Phe Asp Ile Asp Tyr Lys Thr Ser Glu Val Asn Gln Arg Val
                245                 250                 255

Phe Ser Leu Asp Glu Val Phe Glu Ile Ala Asn Phe Asn Asn Tyr Leu
            260                 265                 270

Asn Gln Ser Gly Ile Thr Lys Phe Asn Thr Ile Ile Gly Gly Lys Phe
        275                 280                 285

Val Asn Gly Glu Asn Thr Lys Arg Lys Gly Ile Asn Glu Tyr Ile Asn
290                 295                 300

Leu Tyr Ser Gln Gln Ile Asn Asp Lys Thr Leu Lys Lys Tyr Lys Met
305                 310                 315                 320

Ser Val Leu Phe Lys Gln Ile Leu Ser Asp Thr Glu Ser Lys Ser Phe
                325                 330                 335

Val Ile Asp Lys Leu Glu Asp Asp Ser Asp Val Val Thr Thr Met Gln
            340                 345                 350

Ser Phe Tyr Glu Gln Ile Ala Ala Phe Lys Thr Val Glu Glu Lys Ser
        355                 360                 365

Ile Lys Glu Thr Leu Ser Leu Leu Phe Asp Asp Leu Lys Ala Gln Lys
370                 375                 380

Leu Asp Leu Ser Lys Ile Tyr Phe Lys Asn Asp Lys Ser Leu Thr Asp
385                 390                 395                 400

Leu Ser Gln Gln Val Phe Asp Asp Tyr Ser Val Ile Gly Thr Ala Val
                405                 410                 415

Leu Glu Tyr Ile Thr Gln Gln Ile Ala Pro Lys Asn Leu Asp Asn Pro
            420                 425                 430

Ser Lys Lys Glu Gln Glu Leu Ile Ala Lys Lys Thr Glu Lys Ala Lys
        435                 440                 445

Tyr Leu Ser Leu Glu Thr Ile Lys Leu Ala Leu Glu Glu Phe Asn Lys
450                 455                 460

His Arg Asp Ile Asp Lys Gln Cys Arg Phe Glu Glu Ile Leu Ala Asn
465                 470                 475                 480

Phe Ala Ala Ile Pro Met Ile Phe Asp Glu Ile Ala Gln Asn Lys Asp
                485                 490                 495

Asn Leu Ala Gln Ile Ser Ile Lys Tyr Gln Asn Gln Gly Lys Lys Asp
            500                 505                 510

Leu Leu Gln Ala Ser Ala Glu Asp Asp Val Lys Ala Ile Lys Asp Leu
        515                 520                 525

Leu Asp Gln Thr Asn Asn Leu Leu His Lys Leu Lys Ile Phe His Ile
530                 535                 540
```

```
Ser Gln Ser Glu Asp Lys Ala Asn Ile Leu Asp Lys Asp Glu His Phe
545                 550                 555                 560

Tyr Leu Val Phe Glu Glu Cys Tyr Phe Glu Leu Ala Asn Ile Val Pro
                565                 570                 575

Leu Tyr Asn Lys Ile Arg Asn Tyr Ile Thr Gln Lys Pro Tyr Ser Asp
            580                 585                 590

Glu Lys Phe Lys Leu Asn Phe Glu Asn Ser Thr Leu Ala Asn Gly Trp
        595                 600                 605

Asp Lys Asn Lys Glu Pro Asp Asn Thr Ala Ile Leu Phe Ile Lys Asp
    610                 615                 620

Asp Lys Tyr Tyr Leu Gly Val Met Asn Lys Asn Asn Lys Ile Phe
625                 630                 635                 640

Asp Asp Lys Ala Ile Lys Glu Asn Lys Gly Glu Gly Tyr Lys Lys Ile
                645                 650                 655

Val Tyr Lys Leu Leu Pro Gly Ala Asn Lys Met Leu Pro Lys Val Phe
            660                 665                 670

Phe Ser Ala Lys Ser Ile Lys Phe Tyr Asn Pro Ser Glu Asp Ile Leu
        675                 680                 685

Arg Ile Arg Asn His Ser Thr His Thr Lys Asn Gly Ser Pro Gln Lys
    690                 695                 700

Gly Tyr Glu Lys Phe Glu Phe Asn Ile Glu Asp Cys Arg Lys Phe Ile
705                 710                 715                 720

Asp Phe Tyr Lys Gln Ser Ile Ser Lys His Pro Glu Trp Lys Asp Phe
                725                 730                 735

Gly Phe Arg Phe Ser Asp Thr Gln Arg Tyr Asn Ser Ile Asp Glu Phe
            740                 745                 750

Tyr Arg Glu Val Glu Asn Gln Gly Tyr Lys Leu Thr Phe Glu Asn Ile
        755                 760                 765

Ser Glu Ser Tyr Ile Asp Ser Val Val Asn Gln Gly Lys Leu Tyr Leu
    770                 775                 780

Phe Gln Ile Tyr Asn Lys Asp Phe Ser Ala Tyr Ser Lys Gly Arg Pro
785                 790                 795                 800

Asn Leu His Thr Leu Tyr Trp Lys Ala Leu Phe Asp Glu Arg Asn Leu
                805                 810                 815

Gln Asp Val Val Tyr Lys Leu Asn Gly Glu Ala Glu Leu Phe Tyr Arg
            820                 825                 830

Lys Gln Ser Ile Pro Lys Lys Ile Thr His Pro Ala Lys Glu Ala Ile
        835                 840                 845

Ala Asn Lys Asn Lys Asp Asn Pro Lys Lys Glu Ser Val Phe Glu Tyr
    850                 855                 860

Asp Leu Ile Lys Asp Lys Arg Phe Thr Glu Asp Lys Phe Phe Phe His
865                 870                 875                 880

Cys Pro Ile Thr Ile Asn Phe Lys Ser Ser Gly Ala Asn Lys Phe Asn
                885                 890                 895

Asp Glu Ile Asn Leu Leu Leu Lys Glu Lys Ala Asn Asp Val His Ile
            900                 905                 910

Leu Ser Ile Asp Arg Gly Glu Arg His Leu Ala Tyr Tyr Thr Leu Val
        915                 920                 925

Asp Gly Lys Gly Asn Ile Ile Lys Gln Asp Thr Phe Asn Ile Ile Gly
    930                 935                 940

Asn Asp Arg Met Lys Thr Asn Tyr His Asp Lys Leu Ala Ala Ile Glu
945                 950                 955                 960
```

Lys Asp Arg Asp Ser Ala Arg Lys Asp Trp Lys Ile Asn Asn Ile
                965                 970                 975

Lys Glu Met Lys Glu Gly Tyr Leu Ser Gln Val Val His Glu Ile Ala
            980                 985                 990

Lys Leu Val Ile Glu Tyr Asn Ala Ile Val Val Phe Glu Asp Leu Asn
        995                 1000                1005

Phe Gly Phe Lys Arg Gly Arg Phe Lys Val Glu Lys Gln Val Tyr
    1010                1015                1020

Gln Lys Leu Glu Lys Met Leu Ile Glu Lys Leu Asn Tyr Leu Val
    1025                1030                1035

Phe Lys Asp Asn Glu Phe Asp Lys Thr Gly Gly Val Leu Arg Ala
    1040                1045                1050

Tyr Gln Leu Thr Ala Pro Phe Glu Thr Phe Lys Lys Met Gly Lys
    1055                1060                1065

Gln Thr Gly Ile Ile Tyr Tyr Val Pro Ala Gly Phe Thr Ser Lys
    1070                1075                1080

Ile Cys Pro Val Thr Gly Phe Val Asn Gln Leu Tyr Pro Lys Tyr
    1085                1090                1095

Glu Ser Val Ser Lys Ser Gln Glu Phe Phe Ser Lys Phe Asp Lys
    1100                1105                1110

Ile Cys Tyr Asn Leu Asp Lys Gly Tyr Phe Glu Phe Ser Phe Asp
    1115                1120                1125

Tyr Lys Asn Phe Gly Asp Lys Ala Ala Lys Gly Lys Trp Thr Ile
    1130                1135                1140

Ala Ser Phe Gly Ser Arg Leu Ile Asn Phe Arg Asn Ser Asp Lys
    1145                1150                1155

Asn His Asn Trp Asp Thr Arg Glu Val Tyr Pro Thr Lys Glu Leu
    1160                1165                1170

Glu Lys Leu Leu Lys Asp Tyr Ser Ile Glu Tyr Gly His Gly Glu
    1175                1180                1185

Cys Ile Lys Ala Ala Ile Cys Gly Glu Ser Asp Lys Lys Phe Phe
    1190                1195                1200

Ala Lys Leu Thr Ser Val Leu Asn Thr Ile Leu Gln Met Arg Asn
    1205                1210                1215

Ser Lys Thr Gly Thr Glu Leu Asp Tyr Leu Ile Ser Pro Val Ala
    1220                1225                1230

Asp Val Asn Gly Asn Phe Phe Asp Ser Arg Gln Ala Pro Lys Asn
    1235                1240                1245

Met Pro Gln Asp Ala Asp Ala Asn Gly Ala Tyr His Ile Gly Leu
    1250                1255                1260

Lys Gly Leu Met Leu Leu Gly Arg Ile Lys Asn Asn Gln Glu Gly
    1265                1270                1275

Lys Lys Leu Asn Leu Val Ile Lys Asn Glu Glu Tyr Phe Glu Phe
    1280                1285                1290

Val Gln Asn Arg Asn Asn
    1295

<210> SEQ ID NO 16
<211> LENGTH: 3897
<212> TYPE: DNA
<213> ORGANISM: Artificial Sequence
<220> FEATURE:
<223> OTHER INFORMATION: Synthetic sequence. FnCas12a

<400> SEQUENCE: 16

```
agtatctacc aggagttcgt gaacaaatac tccctgagca aaaccctgcg ctttgaactg    60
atcccgcagg gtaaaactct ggaaaacatc aaagctcgcg gcctgattct ggacgatgaa   120
aaacgcgcga agattacaa aaaagcgaaa cagatcatcg ataaatacca ccagttcttc   180
atcgaagaga tcctgtcttc tgtgtgcatc agcgaggacc tcctgcagaa ctatagcgat   240
gtctacttca aactgaaaaa gagcgatgac gacaacctcc agaaagattt caaaagcgcc   300
aaagacacca ttaagaagca gatctccgaa tacattaagg attctgagaa atttaaaaac   360
ctcttcaacc agaacctgat cgacgcgaaa aaaggccagg agagcgatct gattctgtgg   420
ctgaaacagt ccaaggataa cggtattgaa cttttttaagg ctaactctga catcactgac   480
atcgatgaag ccctggaaat catcaaatcc tttaaaggtt ggaccactta cttcaaaggt   540
ttccatgaaa atcgcaaaaa cgtttatagc tctaacgata ttccgacatc catcatctac   600
cgcatcgttg atgacaactt gccgaaattc ctggaaaaca aggctaaata tgaatccctg   660
aaagacaaag cgccggaagc aatcaattat gaacagatta aaaagacct ggctgaagaa   720 ctgaccttcg acatcgacta caaaaccagc gaggttaacc agcgcgtatt ctctctggac   780
gaagtcttcg agatcgctaa cttcaacaac tacctgaacc agtccggcat cacgaaattc   840
aacaccatta tcggcggcaa atttgtgaac ggcgaaaaca ctaaacgtaa aggcatcaat   900
gagtacatca atctgtactc ccagcagatt aatgataaaa cactgaagaa atataaaatg   960
agcgtgctgt tcaaacagat cctctctgat accgaaagca gagcttcgt tatcgataaa  1020 cttgaagacg atagcgatgt tgttactacc atgcagtcct tctatgagca gatcgcagct  1080
tttaaaaccg ttgaagaaaa atccatcaaa gaaaccttat ccctgctgtt cgatgatctg  1140
aaagcacaga aacttgacct gtccaaaatt tacttcaaaa acgacaaaag cctgaccgat  1200
ttaagccagc aggtgttcga tgattatagc gtgattggga cggcagtgct ggaatacatc  1260
acccaacaaa tcgcgccgaa aaacctggac aacccatcta aaaagagca ggagctgatt  1320 gcgaaaaaga ctgaaaaagc taaatatctg tccctggaga ccatcaaact ggcgctggag  1380
gagtttaaca agcatcgcga tattgataag cagtgccgtt ttgaagaaat cctggcgaac  1440
ttcgcagcga tcccaatgat ttttgacgaa atcgcacaga acaaagataa cctggcgcag  1500
atcagcatca ataccagaa ccagggtaag aaggacctgc tgcaggcatc ggccgaagat  1560
gatgttaaag caatcaaaga tctcttggat caaaccaata acctgctgca caaactgaaa  1620
atcttccaca tttcccagtc tgaagataag gcgaacattc tggataaaga tgaacacttc  1680
tatctcgtat ttgaggaatg ttatttcgag ctggcaaaca tcgttccgct gtacaacaaa  1740
atccgtaact acatcaccca gaaaccgtac agcgacgaaa aattcaagct gaatttcgaa  1800 aatagcaccct tagcgaatgg ttgggacaaa aataaagaac tgacaacac cgcgatcctg  1860 ttcatcaaag atgataaata ctacctgggc gtaatgaaca aaaagaacaa caaaatcttt  1920
gacgacaaag cgattaaaga aaacaaaggc gaaggctata aaaagatcgt gtataagctg  1980
ctgccgggtg cgaacaagat gctgccgaag gtattcttct ctgccaaaag catcaaattc  2040
tataacccgt cggaagacat tctgcgcatc cgtaaccact cgacacatac caaaaatggc  2100
tccccccaga aaggttacga aaaatttgag ttcaacattg aagattgtcg taaatttatc  2160
gacttttaca aacagagcat cagtaaacat ccggaatgga aagattttgg cttccgcttt  2220 tcggatacc agcgttacaa ctccatcgac gagttctacc gcgaagttga aaaccagggt  2280
tacaaactga ctttcgaaaa catctcgagg tcttacatcg attctgttgt taaccagggt  2340
aaactgtacc tgttccaaat ctacaacaag gacttctcag cctacagcaa aggccgcccg  2400
```

```
aatctgcata ccctgtattg gaaagcgctc ttcgatgaac gtaacctgca ggatgtggtt    2460
tacaaactga atggtgaagc tgaactcttt tatcgtaaac agtcaatccc gaagaaaatc    2520
acccacccgg caaaggaagc gattgccaac aaaaacaagg acaacccctaa gaaggaaagc   2580 gtgttcgaat acgatctgat taaagacaag cgcttcacgg aagacaaatt ctttttccac    2640
tgcccgatca ccattaactt taaatctagc ggggctaaca aattcaacga tgaaatcaac    2700
ttacttctga agaaaaaagc taacgacgtt catattctca gtattgaccg gggcgaacgt    2760
catctggcat actacacccct ggttgacggc aaaggcaaca tcattaagca ggacacattc    2820
aacatcatcg gcaacgatcg tatgaaaact aattaccacg ataaactggc ggcgatcgag    2880
aaagatcgtg atagcgctcg taaggactgg aaaaagatca acaacattaa agaaatgaag    2940
gaaggttacc tgagccaggt tgtgcatgaa atcgcaaaac tggtcatcga atataacgcg    3000
atcgtcgtct ttgaagacct gaacttcggt tttaaacgtg gtcgcttcaa agtcgaaaaa    3060
caggtgtacc agaagctgga gaaaatgctg atcgaaaaac tgaactatct ggtattcaaa    3120
gataacgaat ttgataaaac cggtggtgtc ctccgtgctt accaactgac cgctcctttc    3180
gaaaccttta gaaaatggg taagcagacc ggcattatct actatgtgcc agcaggcttc    3240
acctctaaaa tttgcccggt caccggcttt gtcaaccaac tgtacccaaa atacgaatct    3300
gtgagcaaat cccaggaatt tttcagcaaa ttcgataaaa tttgttacaa cctggataaa    3360 ggctatttg aatttagctt tgactacaaa actttggcg ataaagctgc aaaaggtaaa    3420
tggaccatcg cgagtttcgg ttctcgtctg atcaacttcc gcaacagcga taaaaaccat    3480
aactgggaca ctcgtgaagt ttacccgacc aaggaattag aaaaactgct caaagattac    3540
agtatcgaat acggccacgg tgaatgtatc aaagcagcaa tctgcggtga gtctgataaa    3600
aaatttttcg cgaaactgac gtctgtactg aacactattc tgcagatgcg taactccaaa    3660
accggtaccg aactggacta cctgatcagc ccggttgcgg acgttaatgg taactttttc    3720
gacagccgtc aggcaccgaa aaacatgcct caggatgcga acgccaacgg cgcgtaccac    3780
atcggcctga aaggcctgat gttgctgggt cgcatcaaaa ataaccagga aggcaaaaaa    3840
ctgaacctgg tgattaaaaa tgaagaatac tttgagttcg tgcagaaccg taataac     3897
```

<210> SEQ ID NO 17
<211> LENGTH: 4023
<212> TYPE: DNA
<213> ORGANISM: Artificial Sequence
<220> FEATURE:
<223> OTHER INFORMATION: Synthetic sequence. FBNYV:Linker:Cys-free LbCas12a

<400> SEQUENCE: 17

```
atggcgcgcc aggtgatttg ctggtgcttt accctgaaca acccgctgag cccgctgagc      60
ctgcatgata gcatgaaata tctggtgtat cagaccgaac agggcgaagc gggcaacatt     120
cattttcagg gctatattga aatgaaaaaa cgcaccagcc tggcgggcat gaaaaaactg     180
attccgggcg cgcatttga aaaacgccgc ggcacccagg gcgaagcgcg cgcgtatagc     240
atgaaagaag ataccccgcct ggaaggcccg tgggaatatg cgaatttgt gccgtctgct     300 tctgatactg gtggttcttc tgaaactggt actttagatt ctagcaaact ggaaaaattc     360
accaacctgt actcccctgag caaaacccctg cgcttcaaag cgatcccggt tggtaaaacc     420
caggaaaaca tcgataacaa cgccctcctg gtcgaagacg agaaacgcgc agaggactac     480
aaaggcgtca aaaagctgct cgatcgctac tacctgagct tcatcaacga tgtgttgcac     540
```

```
agcatcaaac tgaagaacct gaacaactac atcagcctgt tccgcaagaa aacccgtacc    600
gaaaaagaga acaaagaact ggaaaacctg gaaattaacc tgcgtaaaga aatcgctaaa    660
gcgttcaaag gtaacgaggg ctacaaatct ctgttcaaaa aggacatcat cgaaaccatc    720
ctgccggaat ttctggatga caaagatgaa atcgcgctgg tgaactcgtt caacggcttc    780
acgaccgcgt tcacgggttt cttcgacaac cgcgagaaca tgtttagcga ggaagcgaaa    840
agcaccagca tcgccttccg tatcatcaac gaaaacctga cccgctacat cagcaacatg    900
gacattttcg agaaggttga cgctatcttt gacaaacacg aggttcagga gatcaaggag    960
aaaatcctga cacgcgacta cgatgtggaa gacttcttcg aaggcgagtt cttcaacttc   1020
gttctgaccc aagagggcat cgacgtttac aacgccatca ttggcggctt cgtaaccgaa   1080
agcggtgaaa agatcaaagg gctgaacgag tatatcaacc tgtataacca gaaaaccaaa   1140
cagaaactgc cgaaattcaa gccgctgtac aagcaggttc tgtccgaccg cgagagcctg   1200
agcttctatg gcgagggcta cacgtccgac gaggaagtgc tcgaagtctt ccgcaacacc   1260
ctgaacaaga acagcgagat cttctcgtcc atcaaaaagc tggagaaact gttcaagaac   1320
ttcgacgagt actcttctgc gggcatcttc gtgaaaaacg gcccggccat cagcacgatt   1380
tccaaggata tctttggcga gtggaacgtg atccgcgaca aatggaacgc tgaatacgac   1440
gacatccatc tgaagaagaa ggcggtcgtt accgaaaaat acgaagatga ccgccgcaag   1500
tcttttaaaa agatcggctc gttcagcctg gagcagctgc aggaatacgc ggacgctgac   1560
ttgagcgtgg tcgagaaact gaaagagatc atcatccaga aggtcgacga aatctacaaa   1620
gtgtacggca gtagcgaaaa actgttcgac gctgatttcg tcctggaaaa gagcctgaaa   1680
aagaacgacg cggtggtggc gatcatgaag gacctgctgg acagcgttaa gtcgttcgaa   1740
aactacatta aagcgttttt cggggaaggc aaagaaacca ccgcgacga atcttttttac   1800 ggtgactttg tcctcgccta cgacatcctg ctcaaagtcg accacatcta tgacgctatc   1860
cgcaactacg tgacccagaa gccgtacagc aaagacaaat tcaagctgta cttccagaac   1920
ccccagttca tgggcggctg ggataaggac aaggaaaccg actaccgcgc caccatcctg   1980
cgctacggta gcaaatatta cctggcgatc atggacaaaa aatacgccaa atctttgcag   2040
aaaatcgaca aggacgacgt gaacggtaac tacgaaaaaa ttaactataa actgctgccg   2100
ggtccgaaca aaatgctgcc gaaagtgttc ttcagcaaaa aatggatggc atactacaac   2160
ccgtctgaag atattcagaa aatctacaaa aacggcacct tcaaaaaagg tgatatgttc   2220
aacctgaaca atctgcacaa actgattgat ttcttcaagg actcgatctc tcgttatccg   2280
aaatggtcta acgcgtacga cttcaacttc agcgaaaccg aaaaatacaa agatatcgcg   2340
ggtttctatc gtgaagttga agaacagggc tacaaagtgt cttttcgaatc cgcgtccaaa   2400 aaggaagtgg ataaactggt cgaagaaggt aaactgtaca tgttccagat ctataacaaa   2460
gacttcagcg ataaatccca tggcaccccg aacctgcaca ccatgtactt caaactgctg   2520
ttcgatgaaa acaaccacgg ccagatccgt ctgtccggcg gtgcagaact gtttatgcgc   2580
cgtgcgtccc tgaaaaaaga agagctggta gtacatccgg caaactctcc gatcgctaac   2640
aaaaacccgg acaacccgaa gaaaaccacc accctgagct atgatgtata taagataaa    2700 cgtttctccg aagatcagta cgaactgcac atcccgatcg caattaacaa agcgccgaaa   2760
aacatcttca aaatcaacac cgaagtgcgt gttctgctga acacgatga taacccgtac    2820 gttattggca tcgaccgtgg cgaacgtaac ctgctgtaca tcgttgtggt tgacggtaaa   2880
```

| | |
|---|---|
| ggtaacattg tggaacagta tagcctgaac gaaatcatta acaacttcaa cggtatccgt | 2940 |
| atcaaaaccg attatcacag cctgctggat aaaaagaaa aagaacgttt tgaagcgcgt | 3000 |
| cagaactgga ccagcatcga aacatcaaa gaactgaaag cgggctacat ctcgcaggtt | 3060 |
| gttcacaaaa tcgtggaact ggttgaaaaa tacgatgcag ttatcgcgct ggaagatctg | 3120 |
| aacagcggtt tcaaaaactc acgtgtaaaa gttgaaaaac aggtttacca gaaattcgaa | 3180 |
| aaaatgctga ttgataaact gaactatatg gtggataaaa aatctaaccc gagcgcgact | 3240 |
| ggtggcgcac tgaaaggcta tcagatcacc aacaagttcg agagcttcaa aagcatgagc | 3300 |
| acccagaacg gtttcatctt ctatatcccg gcctggctga cctctaaaat tgacccgagc | 3360 |
| actggcttcg tgaacctgct gaaaaccaaa tacactagca tcgctgacag caaaaaattc | 3420 |
| atctcctcct tgaccgtat catgtacgtg ccggaagaag acctgttcga atttgcactg | 3480 |
| gattacaaaa acttctcccg cactgacgcc gactatatta aaaaatggaa actgtactct | 3540 |
| tatggtaacc gtatccgtat cttccgtaac ccgaagaaaa acaacgtttt cgattgggaa | 3600 |
| gaagtgccgc tgaccagcgc gtataaagaa ctgttcaaca aatacggcat taactaccag | 3660 |
| cagggcgaca ttcgtgcgct gctgctggaa cagtccgata aagcgttcta cagctccttc | 3720 |
| atggcactga tgtccctgat gctgcagatg cgtaacagca ttactggccg taccgatgtg | 3780 |
| gatttcctga tcagcccggt taaaaactct gacggcatct tttacgacag ccgtaactac | 3840 |
| gaagcgcagg aaaacgcgat tctgccgaaa acgcggacg ctaacggcgc atacaacatc | 3900 |
| gcacgtaaag tgctgtgggc gatcggtcag ttcaaaaaag cggaagatga aaaactggat | 3960 |
| aaagtgaaaa tcgcgatcag caacaaagaa tggctggaat acgcgcagac cagcgttaaa | 4020 |
| cac | 4023 |

<210> SEQ ID NO 18
<211> LENGTH: 4239
<212> TYPE: DNA
<213> ORGANISM: Artificial Sequence
<220> FEATURE:
<223> OTHER INFORMATION: Synthetic sequence. FnCas12a:Linker:FBNYV

<400> SEQUENCE: 18

| | |
|---|---|
| agtatctacc aggagttcgt gaacaaatac tccctgagca aaaccctgcg ctttgaactg | 60 |
| atcccgcagg gtaaaactct ggaaaacatc aaagctcgcg gcctgattct ggacgatgaa | 120 |
| aaacgcgcga agattacaa aaaagcgaaa cagatcatcg ataaatacca ccagttcttc | 180 |
| atcgaagaga tcctgtcttc tgtgtgcatc agcgaggacc tcctgcagaa ctatagcgat | 240 |
| gtctacttca aactgaaaaa gagcgatgac gacaacctcc agaaagattt caaaagcgcc | 300 |
| aaagacacca ttaagaagca gatctccgaa tacattaagg attctgagaa atttaaaaac | 360 |
| ctcttcaacc agaacctgat cgacgcgaaa aaaggccagg agagcgatct gattctgtgg | 420 |
| ctgaaacagt ccaaggataa cggtattgaa ctttttaagg ctaactctga catcactgac | 480 |
| atcgatgaag ccctggaaat catcaaatcc tttaaaggtt ggaccactta cttcaaaggt | 540 |
| ttccatgaaa atcgcaaaaa cgtttatagc tctaacgata ttccgacatc catcatctac | 600 |
| cgcatcgttg atgacaactt gccgaaattc ctggaaaaca aggctaaaata tgaatccctg | 660 |
| aaagacaaag cgccggaagc aatcaattat gaacagatta aaaagaccct ggctgaagaa | 720 |
| ctgaccttcg acatcgacta caaaaccagc gaggttaacc agcgcgtatt ctctctggac | 780 |
| gaagtcttcg agatcgctaa cttcaacaac tacctgaacc agtccggcat cacgaaattc | 840 |
| aacaccatta tcggcggcaa atttgtgaac ggcgaaaaca ctaaacgtaa aggcatcaat | 900 |

```
gagtacatca atctgtactc ccagcagatt aatgataaaa cactgaagaa atataaaatg    960
agcgtgctgt tcaaacagat cctctctgat accgaaagca agagcttcgt tatcgataaa   1020
cttgaagacg atagcgatgt tgttactacc atgcagtcct tctatgagca gatcgcagct   1080
tttaaaaccg ttgaagaaaa atccatcaaa gaaaccttat ccctgctgtt cgatgatctg   1140
aaagcacaga aacttgacct gtccaaaatt tacttcaaaa acgacaaaag cctgaccgat   1200
ttaagccagc aggtgttcga tgattatagc gtgattggga cggcagtgct ggaatacatc   1260
acccaacaaa tcgcgccgaa aaacctggac aacccatcta aaaagagcag ggagctgatt   1320
gcgaaaaaga ctgaaaaagc taaatatctg tccctggaga ccatcaaact ggcgctggag   1380
gagtttaaca agcatcgcga tattgataag cagtgccgtt ttgaagaaat cctggcgaac   1440
ttcgcagcga tcccaatgat ttttgacgaa atcgcacaga acaaagataa cctggcgcag   1500
atcagcatca ataccagaa ccagggtaag aaggacctgc tgcaggcatc ggccgaagat   1560
gatgttaaag caatcaaaga tctcttggat caaaccaata acctgctgca caaactgaaa   1620
atcttccaca tttcccagtc tgaagataag gcgaacattc tggataaaga tgaacacttc   1680
tatctcgtat ttgaggaatg ttatttcgag ctggcaaaca tcgttccgct gtacaacaaa   1740
atccgtaact acatcaccca gaaaccgtac agcgacgaaa aattcaagct gaatttcgaa   1800
aatagcccct tagcgaatgg ttgggacaaa aataaagaac ctgacaacac cgcgatcctg   1860
ttcatcaaag atgataaata ctacctgggc gtaatgaaca aaagaacaa caaaatcttt   1920 gacgacaaag cgattaaaga aaacaaaggc gaaggctata aaaagatcgt gtataagctg   1980
ctgccgggtg cgaacaagat gctgccgaag gtattcttct ctgccaaaag catcaaattc   2040
tataacccgt cggaagacat tctgcgcatc cgtaaccact cgacacatac caaaaatggc   2100 tcccccccaga aaggttacga aaaatttgag ttcaacattg aagattgtcg taaatttatc   2160
gacttttaca aacagagcat cagtaaacat ccggaatgga agattttggg cttccgcttt   2220
tcggataccc agcgttacaa ctccatcgac gagttctacc gcgaagttga aaaccagggt   2280
tacaaactga ctttcgaaaa catctcggag tcttacatcg attctgttgt taaccagggt   2340
aaactgtacc tgttccaaat ctacaacaag gacttctcag cctacagcaa aggccgcccg   2400
aatctgcata ccctgtattg gaaagcgctc ttcgatgaac gtaacctgca ggatgtggtt   2460
tacaaactga atggtgaagc tgaactcttt tatcgtaaac agtcaatccc gaagaaaatc   2520
acccacccgg caaggaagc gattgccaac aaaaacaagg acaaccctaa gaaggaaagc   2580
gtgttcgaat acgatctgat taagacaag cgcttcacgg aagacaaatt ctttttccac   2640
tgcccgatca ccattaactt taaatctagc ggggctaaca aattcaacga tgaaatcaac   2700
ttacttctga agaaaaagc taacgacgtt catattctca gtattgaccg gggcgaacgt   2760
catctggcat actacaccct ggttgacggc aaaggcaaca tcattaagca ggacacattc   2820
aacatcatcg gcaacgatcg tatgaaaact aattaccacg ataaactggc ggcgatcgag   2880
aaagatcgtg atagcgctcg taaggactgg aaaaagatca acaacattaa agaaatgaag   2940
gaaggttacc tgagccaggt tgtgcatgaa atcgcaaaac tggtcatcga atataacgcg   3000
atcgtcgtct ttgaagacct gaacttcggt tttaaacgtg tcgcttcaa agtcgaaaaa   3060 caggtgtacc agaagctgga gaaaatgctg atcgaaaaac tgaactatct ggtattcaaa   3120
gataacgaat ttgataaaac cggtggtgtc ctccgtgctt accaactgac cgctccttc    3180 gaaacctta agaaaatggg taagcagacc ggcattatct actatgtgcc agcaggcttc   3240
```

| | |
|---|---|
| acctctaaaa tttgcccggt caccggcttt gtcaaccaac tgtacccaaa atacgaatct | 3300 |
| gtgagcaaat cccaggaatt tttcagcaaa ttcgataaaa tttgttacaa cctggataaa | 3360 |
| ggctattttg aatttagctt tgactacaaa aactttggcg ataaagctgc aaaaggtaaa | 3420 |
| tggaccatcg cgagtttcgg ttctcgtctg atcaacttcc gcaacagcga taaaaaccat | 3480 |
| aactgggaca ctcgtgaagt ttacccgacc aaggaattag aaaaactgct caaagattac | 3540 |
| agtatcgaat acggccacgg tgaatgtatc aaagcagcaa tctgcggtga gtctgataaa | 3600 |
| aaattttccg cgaaactgac gtctgtactg aacactattc tgcagatgcg taactccaaa | 3660 |
| accggtaccg aactggacta cctgatcagc ccggttgcgg acgttaatgg taacttttc | 3720 |
| gacagccgtc aggcaccgaa aaacatgcct caggatgcgg acgccaacgg cgcgtaccac | 3780 |
| atcggcctga aaggcctgat gttgctgggt cgcatcaaaa ataaccagga aggcaaaaaa | 3840 |
| ctgaacctgg tgattaaaaa tgaagaatac tttgagttcg tgcagaaccg taataactct | 3900 |
| gcttctgata ctggtggttc ttctgaaact ggtactttag attctatggc gcgccaggtg | 3960 |
| atttgctggt gctttacccct gaacaacccg ctgagcccgc tgagcctgca tgatagcatg | 4020 |
| aaatatctgg tgtatcagac cgaacagggc gaagcgggca acattcattt tcagggctat | 4080 |
| attgaaatga aaaacgcac cagcctggcg ggcatgaaaa aactgattcc gggcgcgcat | 4140 |
| tttgaaaaac gccgcggcac ccagggcgaa gcgcgcgcgt atagcatgaa agaagatacc | 4200 |
| cgcctggaag gcccgtggga atatggcgaa tttgtgccg | 4239 |

<210> SEQ ID NO 19
<211> LENGTH: 4242
<212> TYPE: DNA
<213> ORGANISM: Artificial Sequence
<220> FEATURE:
<223> OTHER INFORMATION: Synthetic sequence. FBNYV:Linker:FnCas12a

<400> SEQUENCE: 19

| | |
|---|---|
| atggcgcgcc aggtgatttg ctggtgcttt accctgaaca acccgctgag cccgctgagc | 60 |
| ctgcatgata gcatgaaata tctggtgtat cagaccgaac agggcgaagc gggcaacatt | 120 |
| cattttcagg gctatattga atgaaaaaa cgcaccagcc tggcgggcat gaaaaaactg | 180 |
| attccgggcg cgcattttga aaaacgccgc ggcacccagg gcgaagcgcg cgcgtatagc | 240 |
| atgaaagaag ataccgcct ggaaggcccg tgggaatatg gcgaatttgt gccgtctgct | 300 |
| tctgatactg gtggttcttc tgaaactggt actttagatt ctagtatcta ccaggagttc | 360 |
| gtgaacaaat actccctgag caaaccctg cgctttgaac tgatcccgca gggtaaaact | 420 |
| ctggaaaaca tcaaagctcg cggcctgatt ctggacgatg aaaaacgcgc gaaagattac | 480 |
| aaaaaagcga acagatcat cgataaatac caccagttct tcatcgaaga gatcctgtct | 540 |
| tctgtgtgca tcagcgagga cctcctgcag aactatagcg atgtctactt caaactgaaa | 600 |
| aagagcgatg acgacaacct ccagaaagat ttcaaaagcg ccaaagacac cattaagaag | 660 |
| cagatctccg aatacattaa ggattctgag aaatttaaaa acctcttcaa ccagaacctg | 720 |
| atcgacgcga aaaaggcca ggagagcgat ctgattctgt ggctgaaaca gtccaaggat | 780 |
| aacggtattg aacttttaa ggctaactct gacatcactg acatcgatga agccctggaa | 840 |
| atcatcaaat cctttaaagg ttggaccact tacttcaaag gtttccatga aaatcgcaaa | 900 |
| aacgttttata gctctaacga tattccgaca tccatcatct accgcatcgt tgatgacaac | 960 |
| ttgccgaaat tcctgaaaa caaggctaaa tatgaatccc tgaaagacaa agcgccgaaa | 1020 |
| gcaatcaatt atgaacagat taaaaaagac ctggctgaag aactgaccct cgacatcgac | 1080 |

```
tacaaaaccaa gcgaggttaa ccagcgcgta ttctctctgg acgaagtctt cgagatcgct   1140
aacttcaaca actacctgaa ccagtccggc atcacgaaat tcaacaccat tatcggcggc   1200
aaatttgtga acggcgaaaa cactaaacgt aaaggcatca atgagtacat caatctgtac   1260
tcccagcaga ttaatgataa acactgaaga aaatataaaa tgagcgtgct gttcaaacag   1320
atcctctctg ataccgaaag caagagcttc gttatcgata aacttgaaga cgatagcgat   1380
gttgttacta ccatgcagtc cttctatgag cagatcgcag cttttaaaac cgttgaagaa   1440
aaatccatca aagaaaccct atccctgctg ttcgatgatc tgaaagcaca gaaacttgac   1500
ctgtccaaaa tttacttcaa aaacgacaaa agcctgaccg atttaagcca gcaggtgttc   1560
gatgattata gcgtgattgg gacggcagtg ctggaataca tcacccaaca aatcgcgccg   1620
aaaaacctgg acaacccatc taaaaaagag caggagctga ttgcgaaaaa gactgaaaaa   1680
gctaaatatc tgtccctgga gaccatcaaa ctggcgctgg aggagtttaa caagcatcgc   1740
gatattgata agcagtgccg ttttgaagaa atcctggcga acttcgcagc gatcccaatg   1800 attttttgacg aaatcgcaca gaacaaagat aacctggcgc agatcagcat caaataccag   1860
aaccagggta agaaggacct gctgcaggca tcggccgaag atgatgttaa agcaatcaaa   1920
gatctcttgg atcaaaccaa taacctgctg cacaaactga aaatcttcca catttcccag   1980
tctgaagata aggcgaacat tctggataaa gatgaacact tctatctcgt atttgaggaa   2040
tgttatttcg agctggcaaa catcgttccg ctgtacaaca aaatccgtaa ctacatcacc   2100
cagaaaccgt acagcgacga aaaattcaag ctgaatttcg aaaatagcac cttagcgaat   2160
ggttgggaca aaaataaaga acctgacaac accgcgatcc tgttcatcaa agatgataaa   2220
tactacctgg gcgtaatgaa caaaaagaac aacaaaatct tgacgacaa agcgattaaa   2280 gaaacaaag gcgaaggcta taaaaagatc gtgtataagc tgctgccggg tgcgaacaag   2340
atgctgccga aggtattctt ctctgccaaa agcatcaaat tctataaccc gtcggaagac   2400
attctgcgca tccgtaacca ctcgacacat accaaaaatg gctccccca gaaaggttac   2460 gaaaaatttg agttcaacat tgaagattgt cgtaaattta tcgacttta caaacagagc   2520 atcagtaaac atccggaatg gaaagatttt ggcttccgct tttcggatac ccagcgttac   2580
aactccatcg acgagttcta ccgcgaagtt gaaaaccagg gttacaaaact gactttcgaa   2640 aacatctcgg agtcttacat cgattctgtt gttaaccagg gtaaactgta cctgttccaa   2700
atctacaaca aggacttctc agcctacagc aaaggccgcc cgaatctgca taccctgtat   2760
tggaaagcgc tcttcgatga acgtaacctg caggatgtgg tttacaaact gaatggtgaa   2820
gctgaactct tttatcgtaa acagtcaatc ccgaagaaaa tcacccaccc ggcaaaggaa   2880
gcgattgcca acaaaaacaa ggacaaccct aagaaggaaa gcgtgttcga atacgatctg   2940
attaaagaca agcgcttcac ggaagacaaa ttctttttcc actgcccgat caccattaac   3000
tttaaatcta gcggggctaa caaattcaac gatgaaatca acttacttct gaagaaaaa   3060 gctaacgacg ttcatattct cagtattgac cggggcgaac gtcatctggc atactacacc   3120
ctggttgacg gcaaaggcaa catcattaag caggacacat tcaacatcat cggcaacgat   3180
cgtatgaaaa ctaattacca cgataaactg gcggcgatcg agaaagatcg tgatagcgct   3240
cgtaaggact ggaaaaagat caacaacatt aagaaatga aggaaggtta cctgagccag   3300
gttgtgcatg aaatcgcaaa actggtcatc gaatataacg cgatcgtcgt ctttgaagac   3360
ctgaacttcg gttttaaacg tggtcgcttc aaagtcgaaa aacaggtgta ccagaagctg   3420
```

| | |
|---|---|
| gagaaaatgc tgatcgaaaa actgaactat ctggtattca agataacga atttgataaa | 3480 |
| accggtggtg tcctccgtgc ttaccaactg accgctcctt tcgaaaccct taagaaaatg | 3540 |
| ggtaagcaga ccggcattat ctactatgtg ccagcaggct tcacctctaa aatttgcccg | 3600 |
| gtcaccggct ttgtcaacca actgtaccca aaatacgaat ctgtgagcaa atcccaggaa | 3660 |
| tttttcagca aattcgataa aatttgttac aacctggata aaggctattt tgaatttagc | 3720 |
| tttgactaca aaactttggg cgataaagct gcaaaaggta atggaccat cgcgagtttc | 3780 |
| ggttctcgtc tgatcaactt ccgcaacagc gataaaaacc ataactggga cactcgtgaa | 3840 |
| gtttacccga ccaaggaatt agaaaaactg ctcaaagatt acagtatcga atacggccac | 3900 |
| ggtgaatgta tcaaagcagc aatctgcggt gagtctgata aaaaattttt cgcgaaactg | 3960 |
| acgtctgtac tgaacactat tctgcagatg cgtaactcca aaaccggtac cgaactggac | 4020 |
| tacctgatca gcccggttgc ggacgttaat ggtaacttttt tcgacagccg tcaggcaccg | 4080 |
| aaaaacatgc tcaggatgc ggacgccaac ggcgcgtacc acatcggcct gaaaggcctg | 4140 |
| atgttgctgg gtcgcatcaa aaataaccag gaaggcaaaa aactgaacct ggtgattaaa | 4200 |
| aatgaagaat actttgagtt cgtgcagaac cgtaataact ga | 4242 |

<210> SEQ ID NO 20
<211> LENGTH: 1341
<212> TYPE: PRT
<213> ORGANISM: Artificial Sequence
<220> FEATURE:
<223> OTHER INFORMATION: Synthetic sequence. Cys-free
    LbCas12a:Linker:FBNYV

<400> SEQUENCE: 20

```
Ser Lys Leu Glu Lys Phe Thr Asn Leu Tyr Ser Leu Ser Lys Thr Leu
1               5                   10                  15

Arg Phe Lys Ala Ile Pro Val Gly Lys Thr Gln Glu Asn Ile Asp Asn
            20                  25                  30

Lys Arg Leu Leu Val Glu Asp Glu Lys Arg Ala Glu Asp Tyr Lys Gly
        35                  40                  45

Val Lys Lys Leu Leu Asp Arg Tyr Tyr Leu Ser Phe Ile Asn Asp Val
    50                  55                  60

Leu His Ser Ile Lys Leu Lys Asn Leu Asn Asn Tyr Ile Ser Leu Phe
65                  70                  75                  80

Arg Lys Lys Thr Arg Thr Glu Lys Glu Asn Lys Glu Leu Glu Asn Leu
                85                  90                  95

Glu Ile Asn Leu Arg Lys Glu Ile Ala Lys Ala Phe Lys Gly Asn Glu
            100                 105                 110

Gly Tyr Lys Ser Leu Phe Lys Lys Asp Ile Ile Glu Thr Ile Leu Pro
        115                 120                 125

Glu Phe Leu Asp Asp Lys Asp Glu Ile Ala Leu Val Asn Ser Phe Asn
    130                 135                 140

Gly Phe Thr Thr Ala Phe Thr Gly Phe Phe Asp Asn Arg Glu Asn Met
145                 150                 155                 160

Phe Ser Glu Glu Ala Lys Ser Thr Ser Ile Ala Phe Arg Ile Ile Asn
                165                 170                 175

Glu Asn Leu Thr Arg Tyr Ile Ser Asn Met Asp Ile Phe Glu Lys Val
            180                 185                 190

Asp Ala Ile Phe Asp Lys His Glu Val Gln Glu Ile Lys Glu Lys Ile
        195                 200                 205

Leu Asn Ser Asp Tyr Asp Val Glu Asp Phe Phe Glu Gly Glu Phe Phe
```

```
            210                 215                 220
Asn Phe Val Leu Thr Gln Glu Gly Ile Asp Val Tyr Asn Ala Ile Ile
225                 230                 235                 240

Gly Gly Phe Val Thr Glu Ser Gly Glu Lys Ile Lys Gly Leu Asn Glu
                245                 250                 255

Tyr Ile Asn Leu Tyr Asn Gln Lys Thr Lys Gln Lys Leu Pro Lys Phe
                260                 265                 270

Lys Pro Leu Tyr Lys Gln Val Leu Ser Asp Arg Glu Ser Leu Ser Phe
                275                 280                 285

Tyr Gly Glu Gly Tyr Thr Ser Asp Glu Glu Val Leu Glu Val Phe Arg
290                 295                 300

Asn Thr Leu Asn Lys Asn Ser Glu Ile Phe Ser Ser Ile Lys Lys Leu
305                 310                 315                 320

Glu Lys Leu Phe Lys Asn Phe Asp Glu Tyr Ser Ser Ala Gly Ile Phe
                325                 330                 335

Val Lys Asn Gly Pro Ala Ile Ser Thr Ile Ser Lys Asp Ile Phe Gly
                340                 345                 350

Glu Trp Asn Val Ile Arg Asp Lys Trp Asn Ala Glu Tyr Asp Asp Ile
                355                 360                 365

His Leu Lys Lys Lys Ala Val Val Thr Glu Lys Tyr Glu Asp Asp Arg
370                 375                 380

Arg Lys Ser Phe Lys Lys Ile Gly Ser Phe Ser Leu Glu Gln Leu Gln
385                 390                 395                 400

Glu Tyr Ala Asp Ala Asp Leu Ser Val Val Glu Lys Leu Lys Glu Ile
                405                 410                 415

Ile Ile Gln Lys Val Asp Glu Ile Tyr Lys Val Tyr Gly Ser Ser Glu
                420                 425                 430

Lys Leu Phe Asp Ala Asp Phe Val Leu Glu Lys Ser Leu Lys Lys Asn
                435                 440                 445

Asp Ala Val Val Ala Ile Met Lys Asp Leu Leu Asp Ser Val Lys Ser
450                 455                 460

Phe Glu Asn Tyr Ile Lys Ala Phe Phe Gly Glu Gly Lys Glu Thr Asn
465                 470                 475                 480

Arg Asp Glu Ser Phe Tyr Gly Asp Phe Val Leu Ala Tyr Asp Ile Leu
                485                 490                 495

Leu Lys Val Asp His Ile Tyr Asp Ala Ile Arg Asn Tyr Val Thr Gln
                500                 505                 510

Lys Pro Tyr Ser Lys Asp Lys Phe Lys Leu Tyr Phe Gln Asn Pro Gln
                515                 520                 525

Phe Met Gly Gly Trp Asp Lys Asp Lys Glu Thr Asp Tyr Arg Ala Thr
530                 535                 540

Ile Leu Arg Tyr Gly Ser Lys Tyr Tyr Leu Ala Ile Met Asp Lys Lys
545                 550                 555                 560

Tyr Ala Lys Ser Leu Gln Lys Ile Asp Lys Asp Val Asn Gly Asn
                565                 570                 575

Tyr Glu Lys Ile Asn Tyr Lys Leu Leu Pro Gly Pro Asn Lys Met Leu
                580                 585                 590

Pro Lys Val Phe Phe Ser Lys Lys Trp Met Ala Tyr Tyr Asn Pro Ser
                595                 600                 605

Glu Asp Ile Gln Lys Ile Tyr Lys Asn Gly Thr Phe Lys Lys Gly Asp
                610                 615                 620

Met Phe Asn Leu Asn Asp Leu His Lys Leu Ile Asp Phe Phe Lys Asp
625                 630                 635                 640
```

```
Ser Ile Ser Arg Tyr Pro Lys Trp Ser Asn Ala Tyr Asp Phe Asn Phe
            645                 650                 655

Ser Glu Thr Glu Lys Tyr Lys Asp Ile Ala Gly Phe Tyr Arg Glu Val
            660                 665                 670

Glu Glu Gln Gly Tyr Lys Val Ser Phe Glu Ser Ala Ser Lys Lys Glu
            675                 680                 685

Val Asp Lys Leu Val Glu Gly Lys Leu Tyr Met Phe Gln Ile Tyr
690                 695                 700

Asn Lys Asp Phe Ser Asp Lys Ser His Gly Thr Pro Asn Leu His Thr
705                 710                 715                 720

Met Tyr Phe Lys Leu Leu Phe Asp Glu Asn Asn His Gly Gln Ile Arg
            725                 730                 735

Leu Ser Gly Gly Ala Glu Leu Phe Met Arg Arg Ala Ser Leu Lys Lys
            740                 745                 750

Glu Glu Leu Val Val His Pro Ala Asn Ser Pro Ile Ala Asn Lys Asn
            755                 760                 765

Pro Asp Asn Pro Lys Lys Thr Thr Leu Ser Tyr Asp Val Tyr Lys
770                 775                 780

Asp Lys Arg Phe Ser Glu Asp Gln Tyr Glu Leu His Ile Pro Ile Ala
785                 790                 795                 800

Ile Asn Lys Ala Pro Lys Asn Ile Phe Lys Ile Asn Thr Glu Val Arg
            805                 810                 815

Val Leu Leu Lys His Asp Asp Asn Pro Tyr Val Ile Gly Ile Asp Arg
            820                 825                 830

Gly Glu Arg Asn Leu Leu Tyr Ile Val Val Asp Gly Lys Gly Asn
            835                 840                 845

Ile Val Glu Gln Tyr Ser Leu Asn Glu Ile Ile Asn Asn Phe Asn Gly
            850                 855                 860

Ile Arg Ile Lys Thr Asp Tyr His Ser Leu Leu Asp Lys Lys Glu Lys
865                 870                 875                 880

Glu Arg Phe Glu Ala Arg Gln Asn Trp Thr Ser Ile Glu Asn Ile Lys
            885                 890                 895

Glu Leu Lys Ala Gly Tyr Ile Ser Gln Val Val His Lys Ile Val Glu
            900                 905                 910

Leu Val Glu Lys Tyr Asp Ala Val Ile Ala Leu Glu Asp Leu Asn Ser
            915                 920                 925

Gly Phe Lys Asn Ser Arg Val Lys Val Glu Lys Gln Val Tyr Gln Lys
            930                 935                 940

Phe Glu Lys Met Leu Ile Asp Lys Leu Asn Tyr Met Val Asp Lys Lys
945                 950                 955                 960

Ser Asn Pro Ser Ala Thr Gly Gly Ala Leu Lys Gly Tyr Gln Ile Thr
            965                 970                 975

Asn Lys Phe Glu Ser Phe Lys Ser Met Ser Thr Gln Asn Gly Phe Ile
            980                 985                 990

Phe Tyr Ile Pro Ala Trp Leu Thr Ser Lys Ile Asp Pro Ser Thr Gly
            995                 1000                1005

Phe Val Asn Leu Leu Lys Thr Lys Tyr Thr Ser Ile Ala Asp Ser
    1010                1015                1020

Lys Lys Phe Ile Ser Ser Phe Asp Arg Ile Met Tyr Val Pro Glu
    1025                1030                1035

Glu Asp Leu Phe Glu Phe Ala Leu Asp Tyr Lys Asn Phe Ser Arg
    1040                1045                1050
```

```
Thr Asp Ala Asp Tyr Ile Lys Lys Trp Lys Leu Tyr Ser Tyr Gly
    1055                1060                1065

Asn Arg Ile Arg Ile Phe Arg Asn Pro Lys Lys Asn Asn Val Phe
    1070                1075                1080

Asp Trp Glu Glu Val Pro Leu Thr Ser Ala Tyr Lys Glu Leu Phe
    1085                1090                1095

Asn Lys Tyr Gly Ile Asn Tyr Gln Gln Gly Asp Ile Arg Ala Leu
    1100                1105                1110

Leu Leu Glu Gln Ser Asp Lys Ala Phe Tyr Ser Ser Phe Met Ala
    1115                1120                1125

Leu Met Ser Leu Met Leu Gln Met Arg Asn Ser Ile Thr Gly Arg
    1130                1135                1140

Thr Asp Val Asp Phe Leu Ile Ser Pro Val Lys Asn Ser Asp Gly
    1145                1150                1155

Ile Phe Tyr Asp Ser Arg Asn Tyr Glu Ala Gln Glu Asn Ala Ile
    1160                1165                1170

Leu Pro Lys Asn Ala Asp Ala Asn Gly Ala Tyr Asn Ile Ala Arg
    1175                1180                1185

Lys Val Leu Trp Ala Ile Gly Gln Phe Lys Lys Ala Glu Asp Glu
    1190                1195                1200

Lys Leu Asp Lys Val Lys Ile Ala Ile Ser Asn Lys Glu Trp Leu
    1205                1210                1215

Glu Tyr Ala Gln Thr Ser Val Lys His Ser Ala Ser Asp Thr Gly
    1220                1225                1230

Gly Ser Ser Glu Thr Gly Thr Leu Asp Ser Met Ala Arg Gln Val
    1235                1240                1245

Ile Cys Trp Cys Phe Thr Leu Asn Asn Pro Leu Ser Pro Leu Ser
    1250                1255                1260

Leu His Asp Ser Met Lys Tyr Leu Val Tyr Gln Thr Glu Gln Gly
    1265                1270                1275

Glu Ala Gly Asn Ile His Phe Gln Gly Tyr Ile Glu Met Lys Lys
    1280                1285                1290

Arg Thr Ser Leu Ala Gly Met Lys Lys Leu Ile Pro Gly Ala His
    1295                1300                1305

Phe Glu Lys Arg Arg Gly Thr Gln Gly Glu Ala Arg Ala Tyr Ser
    1310                1315                1320

Met Lys Glu Asp Thr Arg Leu Glu Gly Pro Trp Glu Tyr Gly Glu
    1325                1330                1335

Phe Val Pro
    1340

<210> SEQ ID NO 21
<211> LENGTH: 1341
<212> TYPE: PRT
<213> ORGANISM: Artificial Sequence
<220> FEATURE:
<223> OTHER INFORMATION: Synthetic sequence. FBNYV:Linker:Cys-free
      LbCas12a

<400> SEQUENCE: 21

Met Ala Arg Gln Val Ile Cys Trp Cys Phe Thr Leu Asn Asn Pro Leu
1               5                   10                  15

Ser Pro Leu Ser Leu His Asp Ser Met Lys Tyr Leu Val Tyr Gln Thr
                20                  25                  30

Glu Gln Gly Glu Ala Gly Asn Ile His Phe Gln Gly Tyr Ile Glu Met
            35                  40                  45
```

```
Lys Lys Arg Thr Ser Leu Ala Gly Met Lys Lys Leu Ile Pro Gly Ala
        50                  55                  60

His Phe Glu Lys Arg Arg Gly Thr Gln Gly Glu Ala Arg Ala Tyr Ser
 65                  70                  75                  80

Met Lys Glu Asp Thr Arg Leu Glu Gly Pro Trp Glu Tyr Gly Glu Phe
                 85                  90                  95

Val Pro Ser Ala Ser Asp Thr Gly Ser Ser Glu Thr Gly Thr Leu
                100                 105                 110

Asp Ser Ser Lys Leu Glu Lys Phe Thr Asn Leu Tyr Ser Leu Ser Lys
        115                 120                 125

Thr Leu Arg Phe Lys Ala Ile Pro Val Gly Lys Thr Gln Glu Asn Ile
    130                 135                 140

Asp Asn Lys Arg Leu Leu Val Glu Asp Glu Lys Arg Ala Glu Asp Tyr
145                 150                 155                 160

Lys Gly Val Lys Lys Leu Leu Asp Arg Tyr Tyr Leu Ser Phe Ile Asn
                165                 170                 175

Asp Val Leu His Ser Ile Lys Leu Lys Asn Leu Asn Asn Tyr Ile Ser
            180                 185                 190

Leu Phe Arg Lys Lys Thr Arg Thr Glu Lys Glu Asn Lys Glu Leu Glu
        195                 200                 205

Asn Leu Glu Ile Asn Leu Arg Lys Glu Ile Ala Lys Ala Phe Lys Gly
    210                 215                 220

Asn Glu Gly Tyr Lys Ser Leu Phe Lys Lys Asp Ile Ile Glu Thr Ile
225                 230                 235                 240

Leu Pro Glu Phe Leu Asp Asp Lys Asp Glu Ile Ala Leu Val Asn Ser
                245                 250                 255

Phe Asn Gly Phe Thr Thr Ala Phe Thr Gly Phe Phe Asp Asn Arg Glu
            260                 265                 270

Asn Met Phe Ser Glu Glu Ala Lys Ser Thr Ser Ile Ala Phe Arg Ile
        275                 280                 285

Ile Asn Glu Asn Leu Thr Arg Tyr Ile Ser Asn Met Asp Ile Phe Glu
    290                 295                 300

Lys Val Asp Ala Ile Phe Asp Lys His Glu Val Gln Glu Ile Lys Glu
305                 310                 315                 320

Lys Ile Leu Asn Ser Asp Tyr Asp Val Glu Asp Phe Phe Glu Gly Glu
                325                 330                 335

Phe Phe Asn Phe Val Leu Thr Gln Glu Gly Ile Asp Val Tyr Asn Ala
            340                 345                 350

Ile Ile Gly Gly Phe Val Thr Glu Ser Gly Glu Lys Ile Lys Gly Leu
        355                 360                 365

Asn Glu Tyr Ile Asn Leu Tyr Asn Gln Lys Thr Lys Gln Lys Leu Pro
    370                 375                 380

Lys Phe Lys Pro Leu Tyr Lys Gln Val Leu Ser Asp Arg Glu Ser Leu
385                 390                 395                 400

Ser Phe Tyr Gly Glu Gly Tyr Thr Ser Asp Glu Val Leu Glu Val
                405                 410                 415

Phe Arg Asn Thr Leu Asn Lys Asn Ser Glu Ile Phe Ser Ser Ile Lys
            420                 425                 430

Lys Leu Glu Lys Leu Phe Lys Asn Phe Asp Glu Tyr Ser Ser Ala Gly
        435                 440                 445

Ile Phe Val Lys Asn Gly Pro Ala Ile Ser Thr Ile Ser Lys Asp Ile
    450                 455                 460
```

-continued

```
Phe Gly Glu Trp Asn Val Ile Arg Asp Lys Trp Asn Ala Glu Tyr Asp
465                 470                 475                 480

Asp Ile His Leu Lys Lys Lys Ala Val Val Thr Glu Lys Tyr Glu Asp
            485                 490                 495

Asp Arg Arg Lys Ser Phe Lys Lys Ile Gly Ser Phe Ser Leu Glu Gln
        500                 505                 510

Leu Gln Glu Tyr Ala Asp Ala Asp Leu Ser Val Val Glu Lys Leu Lys
    515                 520                 525

Glu Ile Ile Ile Gln Lys Val Asp Glu Ile Tyr Lys Val Tyr Gly Ser
530                 535                 540

Ser Glu Lys Leu Phe Asp Ala Asp Phe Val Leu Glu Lys Ser Leu Lys
545                 550                 555                 560

Lys Asn Asp Ala Val Val Ala Ile Met Lys Asp Leu Leu Asp Ser Val
                565                 570                 575

Lys Ser Phe Glu Asn Tyr Ile Lys Ala Phe Phe Gly Glu Gly Lys Glu
            580                 585                 590

Thr Asn Arg Asp Glu Ser Phe Tyr Gly Asp Phe Val Leu Ala Tyr Asp
        595                 600                 605

Ile Leu Leu Lys Val Asp His Ile Tyr Asp Ala Ile Arg Asn Tyr Val
    610                 615                 620

Thr Gln Lys Pro Tyr Ser Lys Asp Lys Phe Lys Leu Tyr Phe Gln Asn
625                 630                 635                 640

Pro Gln Phe Met Gly Trp Asp Lys Asp Lys Glu Thr Asp Tyr Arg
                645                 650                 655

Ala Thr Ile Leu Arg Tyr Gly Ser Lys Tyr Tyr Leu Ala Ile Met Asp
            660                 665                 670

Lys Lys Tyr Ala Lys Ser Leu Gln Lys Ile Asp Lys Asp Val Asn
        675                 680                 685

Gly Asn Tyr Glu Lys Ile Asn Tyr Lys Leu Leu Pro Gly Pro Asn Lys
    690                 695                 700

Met Leu Pro Lys Val Phe Phe Ser Lys Lys Trp Met Ala Tyr Asn
705                 710                 715                 720

Pro Ser Glu Asp Ile Gln Lys Ile Tyr Lys Asn Gly Thr Phe Lys Lys
                725                 730                 735

Gly Asp Met Phe Asn Leu Asn Asp Leu His Lys Leu Ile Asp Phe Phe
            740                 745                 750

Lys Asp Ser Ile Ser Arg Tyr Pro Lys Trp Ser Asn Ala Tyr Asp Phe
        755                 760                 765

Asn Phe Ser Glu Thr Glu Lys Tyr Lys Asp Ile Ala Gly Phe Tyr Arg
    770                 775                 780

Glu Val Glu Glu Gln Gly Tyr Lys Val Ser Phe Glu Ser Ala Ser Lys
785                 790                 795                 800

Lys Glu Val Asp Lys Leu Val Glu Glu Gly Lys Leu Tyr Met Phe Gln
                805                 810                 815

Ile Tyr Asn Lys Asp Phe Ser Lys Ser His Gly Thr Pro Asn Leu
            820                 825                 830

His Thr Met Tyr Phe Lys Leu Leu Phe Asp Glu Asn Asn His Gly Gln
        835                 840                 845

Ile Arg Leu Ser Gly Gly Ala Glu Leu Phe Met Arg Arg Ala Ser Leu
    850                 855                 860

Lys Lys Glu Glu Leu Val Val His Pro Ala Asn Ser Pro Ile Ala Asn
865                 870                 875                 880

Lys Asn Pro Asp Asn Pro Lys Lys Thr Thr Thr Leu Ser Tyr Asp Val
```

```
                885                 890                 895
Tyr Lys Asp Lys Arg Phe Ser Glu Asp Gln Tyr Glu Leu His Ile Pro
                900                 905                 910
Ile Ala Ile Asn Lys Ala Pro Lys Asn Ile Phe Lys Ile Asn Thr Glu
                915                 920                 925
Val Arg Val Leu Leu Lys His Asp Asp Asn Pro Tyr Val Ile Gly Ile
                930                 935                 940
Asp Arg Gly Glu Arg Asn Leu Leu Tyr Ile Val Val Val Asp Gly Lys
945                 950                 955                 960
Gly Asn Ile Val Glu Gln Tyr Ser Leu Asn Glu Ile Ile Asn Asn Phe
                965                 970                 975
Asn Gly Ile Arg Ile Lys Thr Asp Tyr His Ser Leu Leu Asp Lys Lys
                980                 985                 990
Glu Lys Glu Arg Phe Glu Ala Arg Gln Asn Trp Thr Ser Ile Glu Asn
                995                 1000                1005
Ile Lys Glu Leu Lys Ala Gly Tyr Ile Ser Gln Val Val His Lys
                1010                1015                1020
Ile Val Glu Leu Val Glu Lys Tyr Asp Ala Val Ile Ala Leu Glu
                1025                1030                1035
Asp Leu Asn Ser Gly Phe Lys Asn Ser Arg Val Lys Val Glu Lys
                1040                1045                1050
Gln Val Tyr Gln Lys Phe Glu Lys Met Leu Ile Asp Lys Leu Asn
                1055                1060                1065
Tyr Met Val Asp Lys Lys Ser Asn Pro Ser Ala Thr Gly Gly Ala
                1070                1075                1080
Leu Lys Gly Tyr Gln Ile Thr Asn Lys Phe Glu Ser Phe Lys Ser
                1085                1090                1095
Met Ser Thr Gln Asn Gly Phe Ile Phe Tyr Ile Pro Ala Trp Leu
                1100                1105                1110
Thr Ser Lys Ile Asp Pro Ser Thr Gly Phe Val Asn Leu Leu Lys
                1115                1120                1125
Thr Lys Tyr Thr Ser Ile Ala Asp Ser Lys Lys Phe Ile Ser Ser
                1130                1135                1140
Phe Asp Arg Ile Met Tyr Val Pro Glu Glu Asp Leu Phe Glu Phe
                1145                1150                1155
Ala Leu Asp Tyr Lys Asn Phe Ser Arg Thr Asp Ala Asp Tyr Ile
                1160                1165                1170
Lys Lys Trp Lys Leu Tyr Ser Tyr Gly Asn Arg Ile Arg Ile Phe
                1175                1180                1185
Arg Asn Pro Lys Lys Asn Asn Val Phe Asp Trp Glu Glu Val Pro
                1190                1195                1200
Leu Thr Ser Ala Tyr Lys Glu Leu Phe Asn Lys Tyr Gly Ile Asn
                1205                1210                1215
Tyr Gln Gln Gly Asp Ile Arg Ala Leu Leu Leu Glu Gln Ser Asp
                1220                1225                1230
Lys Ala Phe Tyr Ser Ser Phe Met Ala Leu Met Ser Leu Met Leu
                1235                1240                1245
Gln Met Arg Asn Ser Ile Thr Gly Arg Thr Asp Val Asp Phe Leu
                1250                1255                1260
Ile Ser Pro Val Lys Asn Ser Asp Gly Ile Phe Tyr Asp Ser Arg
                1265                1270                1275
Asn Tyr Glu Ala Gln Glu Asn Ala Ile Leu Pro Lys Asn Ala Asp
                1280                1285                1290
```

```
Ala Asn Gly Ala Tyr Asn Ile Ala Arg Lys Val Leu Trp Ala Ile
    1295                1300                1305

Gly Gln Phe Lys Lys Ala Glu Asp Glu Lys Leu Asp Lys Val Lys
    1310                1315                1320

Ile Ala Ile Ser Asn Lys Glu Trp Leu Glu Tyr Ala Gln Thr Ser
    1325                1330                1335

Val Lys His
    1340

<210> SEQ ID NO 22
<211> LENGTH: 1413
<212> TYPE: PRT
<213> ORGANISM: Artificial Sequence
<220> FEATURE:
<223> OTHER INFORMATION: Synthetic sequence. FnCas12a:Linker:FBNYV

<400> SEQUENCE: 22

Ser Ile Tyr Gln Glu Phe Val Asn Lys Tyr Ser Leu Ser Lys Thr Leu
1               5                   10                  15

Arg Phe Glu Leu Ile Pro Gln Gly Lys Thr Leu Glu Asn Ile Lys Ala
                20                  25                  30

Arg Gly Leu Ile Leu Asp Asp Glu Lys Arg Ala Lys Asp Tyr Lys Lys
            35                  40                  45

Ala Lys Gln Ile Ile Asp Lys Tyr His Gln Phe Phe Ile Glu Glu Ile
        50                  55                  60

Leu Ser Ser Val Cys Ile Ser Glu Asp Leu Leu Gln Asn Tyr Ser Asp
65                  70                  75                  80

Val Tyr Phe Lys Leu Lys Lys Ser Asp Asp Asp Asn Leu Gln Lys Asp
                85                  90                  95

Phe Lys Ser Ala Lys Asp Thr Ile Lys Lys Gln Ile Ser Glu Tyr Ile
            100                 105                 110

Lys Asp Ser Glu Lys Phe Lys Asn Leu Phe Asn Gln Asn Leu Ile Asp
        115                 120                 125

Ala Lys Lys Gly Gln Glu Ser Asp Leu Ile Leu Trp Leu Lys Gln Ser
    130                 135                 140

Lys Asp Asn Gly Ile Glu Leu Phe Lys Ala Asn Ser Asp Ile Thr Asp
145                 150                 155                 160

Ile Asp Glu Ala Leu Glu Ile Ile Lys Ser Phe Lys Gly Trp Thr Thr
                165                 170                 175

Tyr Phe Lys Gly Phe His Glu Asn Arg Lys Asn Val Tyr Ser Ser Asn
            180                 185                 190

Asp Ile Pro Thr Ser Ile Ile Tyr Arg Ile Val Asp Asp Asn Leu Pro
        195                 200                 205

Lys Phe Leu Glu Asn Lys Ala Lys Tyr Glu Ser Leu Lys Asp Lys Ala
    210                 215                 220

Pro Glu Ala Ile Asn Tyr Glu Gln Ile Lys Lys Asp Leu Ala Glu Glu
225                 230                 235                 240

Leu Thr Phe Asp Ile Asp Tyr Lys Thr Ser Glu Val Asn Gln Arg Val
                245                 250                 255

Phe Ser Leu Asp Glu Val Phe Glu Ile Ala Asn Phe Asn Asn Tyr Leu
            260                 265                 270

Asn Gln Ser Gly Ile Thr Lys Phe Asn Thr Ile Ile Gly Gly Lys Phe
        275                 280                 285

Val Asn Gly Glu Asn Thr Lys Arg Lys Gly Ile Asn Glu Tyr Ile Asn
    290                 295                 300
```

```
Leu Tyr Ser Gln Gln Ile Asn Asp Lys Thr Leu Lys Lys Tyr Lys Met
305                 310                 315                 320

Ser Val Leu Phe Lys Gln Ile Leu Ser Asp Thr Glu Ser Lys Ser Phe
                325                 330                 335

Val Ile Asp Lys Leu Glu Asp Asp Ser Asp Val Val Thr Thr Met Gln
            340                 345                 350

Ser Phe Tyr Glu Gln Ile Ala Ala Phe Lys Thr Val Glu Glu Lys Ser
        355                 360                 365

Ile Lys Glu Thr Leu Ser Leu Leu Phe Asp Asp Leu Lys Ala Gln Lys
    370                 375                 380

Leu Asp Leu Ser Lys Ile Tyr Phe Lys Asn Asp Lys Ser Leu Thr Asp
385                 390                 395                 400

Leu Ser Gln Gln Val Phe Asp Asp Tyr Ser Val Ile Gly Thr Ala Val
                405                 410                 415

Leu Glu Tyr Ile Thr Gln Gln Ile Ala Pro Lys Asn Leu Asp Asn Pro
            420                 425                 430

Ser Lys Lys Glu Gln Glu Leu Ile Ala Lys Lys Thr Glu Lys Ala Lys
        435                 440                 445

Tyr Leu Ser Leu Glu Thr Ile Lys Leu Ala Leu Glu Glu Phe Asn Lys
    450                 455                 460

His Arg Asp Ile Asp Lys Gln Cys Arg Phe Glu Glu Ile Leu Ala Asn
465                 470                 475                 480

Phe Ala Ala Ile Pro Met Ile Phe Asp Glu Ile Ala Gln Asn Lys Asp
                485                 490                 495

Asn Leu Ala Gln Ile Ser Ile Lys Tyr Gln Asn Gln Gly Lys Lys Asp
            500                 505                 510

Leu Leu Gln Ala Ser Ala Glu Asp Val Lys Ala Ile Lys Asp Leu
        515                 520                 525

Leu Asp Gln Thr Asn Asn Leu Leu His Lys Leu Lys Ile Phe His Ile
    530                 535                 540

Ser Gln Ser Glu Asp Lys Ala Asn Ile Leu Asp Lys Asp Glu His Phe
545                 550                 555                 560

Tyr Leu Val Phe Glu Glu Cys Tyr Phe Glu Leu Ala Asn Ile Val Pro
                565                 570                 575

Leu Tyr Asn Lys Ile Arg Asn Tyr Ile Thr Gln Lys Pro Tyr Ser Asp
            580                 585                 590

Glu Lys Phe Lys Leu Asn Phe Glu Asn Ser Thr Leu Ala Asn Gly Trp
        595                 600                 605

Asp Lys Asn Lys Glu Pro Asp Asn Thr Ala Ile Leu Phe Ile Lys Asp
    610                 615                 620

Asp Lys Tyr Tyr Leu Gly Val Met Asn Lys Lys Asn Asn Lys Ile Phe
625                 630                 635                 640

Asp Asp Lys Ala Ile Lys Glu Asn Lys Gly Glu Gly Tyr Lys Lys Ile
                645                 650                 655

Val Tyr Lys Leu Leu Pro Gly Ala Asn Lys Met Leu Pro Lys Val Phe
            660                 665                 670

Phe Ser Ala Lys Ser Ile Lys Phe Tyr Asn Pro Ser Glu Asp Ile Leu
        675                 680                 685

Arg Ile Arg Asn His Ser Thr His Thr Lys Asn Gly Ser Pro Gln Lys
    690                 695                 700

Gly Tyr Glu Lys Phe Glu Phe Asn Ile Glu Asp Cys Arg Lys Phe Ile
705                 710                 715                 720
```

```
Asp Phe Tyr Lys Gln Ser Ile Ser Lys His Pro Glu Trp Lys Asp Phe
            725                 730                 735
Gly Phe Arg Phe Ser Asp Thr Gln Arg Tyr Asn Ser Ile Asp Glu Phe
            740                 745                 750
Tyr Arg Glu Val Glu Asn Gln Gly Tyr Lys Leu Thr Phe Glu Asn Ile
            755                 760                 765
Ser Glu Ser Tyr Ile Asp Ser Val Val Asn Gln Gly Lys Leu Tyr Leu
            770                 775                 780
Phe Gln Ile Tyr Asn Lys Asp Phe Ser Ala Tyr Ser Lys Gly Arg Pro
785                 790                 795                 800
Asn Leu His Thr Leu Tyr Trp Lys Ala Leu Phe Asp Glu Arg Asn Leu
            805                 810                 815
Gln Asp Val Val Tyr Lys Leu Asn Gly Glu Ala Glu Leu Phe Tyr Arg
            820                 825                 830
Lys Gln Ser Ile Pro Lys Lys Ile Thr His Pro Ala Lys Glu Ala Ile
            835                 840                 845
Ala Asn Lys Asn Lys Asp Asn Pro Lys Lys Glu Ser Val Phe Glu Tyr
            850                 855                 860
Asp Leu Ile Lys Asp Lys Arg Phe Thr Glu Asp Lys Phe Phe Phe His
865                 870                 875                 880
Cys Pro Ile Thr Ile Asn Phe Lys Ser Ser Gly Ala Asn Lys Phe Asn
            885                 890                 895
Asp Glu Ile Asn Leu Leu Leu Lys Glu Lys Ala Asn Asp Val His Ile
            900                 905                 910
Leu Ser Ile Asp Arg Gly Glu Arg His Leu Ala Tyr Tyr Thr Leu Val
            915                 920                 925
Asp Gly Lys Gly Asn Ile Ile Lys Gln Asp Thr Phe Asn Ile Ile Gly
            930                 935                 940
Asn Asp Arg Met Lys Thr Asn Tyr His Asp Lys Leu Ala Ala Ile Glu
945                 950                 955                 960
Lys Asp Arg Asp Ser Ala Arg Lys Asp Trp Lys Lys Ile Asn Asn Ile
            965                 970                 975
Lys Glu Met Lys Glu Gly Tyr Leu Ser Gln Val Val His Glu Ile Ala
            980                 985                 990
Lys Leu Val Ile Glu Tyr Asn Ala Ile Val Val Phe Glu Asp Leu Asn
            995                 1000                1005
Phe Gly Phe Lys Arg Gly Arg Phe Lys Val Glu Lys Gln Val Tyr
            1010                1015                1020
Gln Lys Leu Glu Lys Met Leu Ile Glu Lys Leu Asn Tyr Leu Val
            1025                1030                1035
Phe Lys Asp Asn Glu Phe Asp Lys Thr Gly Gly Val Leu Arg Ala
            1040                1045                1050
Tyr Gln Leu Thr Ala Pro Phe Glu Thr Phe Lys Lys Met Gly Lys
            1055                1060                1065
Gln Thr Gly Ile Ile Tyr Tyr Val Pro Ala Gly Phe Thr Ser Lys
            1070                1075                1080
Ile Cys Pro Val Thr Gly Phe Val Asn Gln Leu Tyr Pro Lys Tyr
            1085                1090                1095
Glu Ser Val Ser Lys Ser Gln Glu Phe Phe Ser Lys Phe Asp Lys
            1100                1105                1110
Ile Cys Tyr Asn Leu Asp Lys Gly Tyr Phe Glu Phe Ser Phe Asp
            1115                1120                1125
Tyr Lys Asn Phe Gly Asp Lys Ala Ala Lys Gly Lys Trp Thr Ile
```

```
                1130                1135                1140
Ala Ser Phe Gly Ser Arg Leu Ile Asn Phe Arg Asn Ser Asp Lys
        1145                1150                1155

Asn His Asn Trp Asp Thr Arg Glu Val Tyr Pro Thr Lys Glu Leu
    1160                1165                1170

Glu Lys Leu Leu Lys Asp Tyr Ser Ile Glu Tyr Gly His Gly Glu
1175                1180                1185

Cys Ile Lys Ala Ala Ile Cys Gly Glu Ser Asp Lys Lys Phe Phe
    1190                1195                1200

Ala Lys Leu Thr Ser Val Leu Asn Thr Ile Leu Gln Met Arg Asn
1205                1210                1215

Ser Lys Thr Gly Thr Glu Leu Asp Tyr Leu Ile Ser Pro Val Ala
    1220                1225                1230

Asp Val Asn Gly Asn Phe Phe Asp Ser Arg Gln Ala Pro Lys Asn
    1235                1240                1245

Met Pro Gln Asp Ala Asp Ala Asn Gly Ala Tyr His Ile Gly Leu
    1250                1255                1260

Lys Gly Leu Met Leu Leu Gly Arg Ile Lys Asn Asn Gln Glu Gly
1265                1270                1275

Lys Lys Leu Asn Leu Val Ile Lys Asn Glu Glu Tyr Phe Glu Phe
1280                1285                1290

Val Gln Asn Arg Asn Asn Ser Ala Ser Asp Thr Gly Gly Ser Ser
    1295                1300                1305

Glu Thr Gly Thr Leu Asp Ser Met Ala Arg Gln Val Ile Cys Trp
    1310                1315                1320

Cys Phe Thr Leu Asn Asn Pro Leu Ser Pro Leu Ser Leu His Asp
    1325                1330                1335

Ser Met Lys Tyr Leu Val Tyr Gln Thr Glu Gln Gly Glu Ala Gly
    1340                1345                1350

Asn Ile His Phe Gln Gly Tyr Ile Glu Met Lys Lys Arg Thr Ser
    1355                1360                1365

Leu Ala Gly Met Lys Lys Leu Ile Pro Gly Ala His Phe Glu Lys
1370                1375                1380

Arg Arg Gly Thr Gln Gly Glu Ala Arg Ala Tyr Ser Met Lys Glu
    1385                1390                1395

Asp Thr Arg Leu Glu Gly Pro Trp Glu Tyr Gly Glu Phe Val Pro
    1400                1405                1410

<210> SEQ ID NO 23
<211> LENGTH: 1413
<212> TYPE: PRT
<213> ORGANISM: Artificial Sequence
<220> FEATURE:
<223> OTHER INFORMATION: Synthetic sequence. FBNYV:Linker:FnCas12a

<400> SEQUENCE: 23

Met Ala Arg Gln Val Ile Cys Trp Cys Phe Thr Leu Asn Asn Pro Leu
1               5                   10                  15

Ser Pro Leu Ser Leu His Asp Ser Met Lys Tyr Leu Val Tyr Gln Thr
            20                  25                  30

Glu Gln Gly Glu Ala Gly Asn Ile His Phe Gln Gly Tyr Ile Glu Met
        35                  40                  45

Lys Lys Arg Thr Ser Leu Ala Gly Met Lys Lys Leu Ile Pro Gly Ala
    50                  55                  60

His Phe Glu Lys Arg Arg Gly Thr Gln Gly Glu Ala Arg Ala Tyr Ser
```

-continued

```
                65                  70                  75                  80
Met Lys Glu Asp Thr Arg Leu Glu Gly Pro Trp Glu Tyr Gly Glu Phe
                    85                  90                  95
Val Pro Ser Ala Ser Asp Thr Gly Gly Ser Ser Glu Thr Gly Thr Leu
                    100                 105                 110
Asp Ser Ser Ile Tyr Gln Glu Phe Val Asn Lys Tyr Ser Leu Ser Lys
                    115                 120                 125
Thr Leu Arg Phe Glu Leu Ile Pro Gln Gly Lys Thr Leu Glu Asn Ile
                    130                 135                 140
Lys Ala Arg Gly Leu Ile Leu Asp Asp Glu Lys Arg Ala Lys Asp Tyr
145                 150                 155                 160
Lys Lys Ala Lys Gln Ile Ile Asp Lys Tyr His Gln Phe Phe Ile Glu
                    165                 170                 175
Glu Ile Leu Ser Ser Val Cys Ile Ser Glu Asp Leu Leu Gln Asn Tyr
                    180                 185                 190
Ser Asp Val Tyr Phe Lys Leu Lys Lys Ser Asp Asp Asn Leu Gln
                    195                 200                 205
Lys Asp Phe Lys Ser Ala Lys Asp Thr Ile Lys Lys Gln Ile Ser Glu
                    210                 215                 220
Tyr Ile Lys Asp Ser Glu Lys Phe Lys Asn Leu Phe Asn Gln Asn Leu
225                 230                 235                 240
Ile Asp Ala Lys Lys Gly Gln Glu Ser Asp Leu Ile Leu Trp Leu Lys
                    245                 250                 255
Gln Ser Lys Asp Asn Gly Ile Glu Leu Phe Lys Ala Asn Ser Asp Ile
                    260                 265                 270
Thr Asp Ile Asp Glu Ala Leu Glu Ile Ile Lys Ser Phe Lys Gly Trp
                    275                 280                 285
Thr Thr Tyr Phe Lys Gly Phe His Glu Asn Arg Lys Asn Val Tyr Ser
                    290                 295                 300
Ser Asn Asp Ile Pro Thr Ser Ile Ile Tyr Arg Ile Val Asp Asp Asn
305                 310                 315                 320
Leu Pro Lys Phe Leu Glu Asn Lys Ala Lys Tyr Glu Ser Leu Lys Asp
                    325                 330                 335
Lys Ala Pro Glu Ala Ile Asn Tyr Glu Gln Ile Lys Lys Asp Leu Ala
                    340                 345                 350
Glu Glu Leu Thr Phe Asp Ile Asp Tyr Lys Thr Ser Glu Val Asn Gln
                    355                 360                 365
Arg Val Phe Ser Leu Asp Glu Val Phe Glu Ile Ala Asn Phe Asn Asn
                    370                 375                 380
Tyr Leu Asn Gln Ser Gly Ile Thr Lys Phe Asn Thr Ile Ile Gly Gly
385                 390                 395                 400
Lys Phe Val Asn Gly Glu Asn Thr Lys Arg Lys Gly Ile Asn Glu Tyr
                    405                 410                 415
Ile Asn Leu Tyr Ser Gln Gln Ile Asn Asp Lys Thr Leu Lys Lys Tyr
                    420                 425                 430
Lys Met Ser Val Leu Phe Lys Gln Ile Leu Ser Asp Thr Glu Ser Lys
                    435                 440                 445
Ser Phe Val Ile Asp Lys Leu Glu Asp Asp Ser Asp Val Val Thr Thr
                    450                 455                 460
Met Gln Ser Phe Tyr Glu Gln Ile Ala Ala Phe Lys Thr Val Glu Glu
465                 470                 475                 480
Lys Ser Ile Lys Glu Thr Leu Ser Leu Leu Phe Asp Asp Leu Lys Ala
                    485                 490                 495
```

```
Gln Lys Leu Asp Leu Ser Lys Ile Tyr Phe Lys Asn Asp Lys Ser Leu
            500                 505                 510

Thr Asp Leu Ser Gln Gln Val Phe Asp Asp Tyr Ser Val Ile Gly Thr
            515                 520                 525

Ala Val Leu Glu Tyr Ile Thr Gln Gln Ile Ala Pro Lys Asn Leu Asp
            530                 535                 540

Asn Pro Ser Lys Lys Glu Gln Glu Leu Ile Ala Lys Lys Thr Glu Lys
545                 550                 555                 560

Ala Lys Tyr Leu Ser Leu Glu Thr Ile Lys Leu Ala Leu Glu Glu Phe
            565                 570                 575

Asn Lys His Arg Asp Ile Asp Lys Gln Cys Arg Phe Glu Glu Ile Leu
            580                 585                 590

Ala Asn Phe Ala Ala Ile Pro Met Ile Phe Asp Glu Ile Ala Gln Asn
            595                 600                 605

Lys Asp Asn Leu Ala Gln Ile Ser Ile Lys Tyr Gln Asn Gln Gly Lys
            610                 615                 620

Lys Asp Leu Leu Gln Ala Ser Ala Glu Asp Asp Val Lys Ala Ile Lys
625                 630                 635                 640

Asp Leu Leu Asp Gln Thr Asn Asn Leu Leu His Lys Leu Lys Ile Phe
            645                 650                 655

His Ile Ser Gln Ser Glu Asp Lys Ala Asn Ile Leu Asp Lys Asp Glu
            660                 665                 670

His Phe Tyr Leu Val Phe Glu Glu Cys Tyr Phe Glu Leu Ala Asn Ile
            675                 680                 685

Val Pro Leu Tyr Asn Lys Ile Arg Asn Tyr Ile Thr Gln Lys Pro Tyr
            690                 695                 700

Ser Asp Glu Lys Phe Lys Leu Asn Phe Glu Asn Ser Thr Leu Ala Asn
705                 710                 715                 720

Gly Trp Asp Lys Asn Lys Glu Pro Asp Asn Thr Ala Ile Leu Phe Ile
            725                 730                 735

Lys Asp Asp Lys Tyr Tyr Leu Gly Val Met Asn Lys Lys Asn Asn Lys
            740                 745                 750

Ile Phe Asp Asp Lys Ala Ile Lys Glu Asn Lys Gly Glu Gly Tyr Lys
            755                 760                 765

Lys Ile Val Tyr Lys Leu Leu Pro Gly Ala Asn Lys Met Leu Pro Lys
            770                 775                 780

Val Phe Phe Ser Ala Lys Ser Ile Lys Phe Tyr Asn Pro Ser Glu Asp
785                 790                 795                 800

Ile Leu Arg Ile Arg Asn His Ser Thr His Thr Lys Asn Gly Ser Pro
            805                 810                 815

Gln Lys Gly Tyr Glu Lys Phe Glu Phe Asn Ile Glu Asp Cys Arg Lys
            820                 825                 830

Phe Ile Asp Phe Tyr Lys Gln Ser Ile Ser Lys His Pro Glu Trp Lys
            835                 840                 845

Asp Phe Gly Phe Arg Phe Ser Asp Thr Gln Arg Tyr Asn Ser Ile Asp
            850                 855                 860

Glu Phe Tyr Arg Glu Val Glu Asn Gln Gly Tyr Lys Leu Thr Phe Glu
865                 870                 875                 880

Asn Ile Ser Glu Ser Tyr Ile Asp Ser Val Val Asn Gln Gly Lys Leu
            885                 890                 895

Tyr Leu Phe Gln Ile Tyr Asn Lys Asp Phe Ser Ala Tyr Ser Lys Gly
            900                 905                 910
```

```
Arg Pro Asn Leu His Thr Leu Tyr Trp Lys Ala Leu Phe Asp Glu Arg
            915                 920                 925

Asn Leu Gln Asp Val Val Tyr Lys Leu Asn Gly Glu Ala Glu Leu Phe
        930                 935                 940

Tyr Arg Lys Gln Ser Ile Pro Lys Lys Ile Thr His Pro Ala Lys Glu
945                 950                 955                 960

Ala Ile Ala Asn Lys Asn Lys Asp Asn Pro Lys Lys Glu Ser Val Phe
                965                 970                 975

Glu Tyr Asp Leu Ile Lys Asp Lys Arg Phe Thr Glu Asp Lys Phe Phe
            980                 985                 990

Phe His Cys Pro Ile Thr Ile Asn Phe Lys Ser Ser Gly Ala Asn Lys
        995                 1000                1005

Phe Asn Asp Glu Ile Asn Leu Leu Leu Lys Glu Lys Ala Asn Asp
    1010                1015                1020

Val His Ile Leu Ser Ile Asp Arg Gly Glu Arg His Leu Ala Tyr
    1025                1030                1035

Tyr Thr Leu Val Asp Gly Lys Gly Asn Ile Ile Lys Gln Asp Thr
    1040                1045                1050

Phe Asn Ile Ile Gly Asn Asp Arg Met Lys Thr Asn Tyr His Asp
    1055                1060                1065

Lys Leu Ala Ala Ile Glu Lys Asp Arg Asp Ser Ala Arg Lys Asp
    1070                1075                1080

Trp Lys Lys Ile Asn Asn Ile Lys Glu Met Lys Glu Gly Tyr Leu
    1085                1090                1095

Ser Gln Val Val His Glu Ile Ala Lys Leu Val Ile Glu Tyr Asn
    1100                1105                1110

Ala Ile Val Val Phe Glu Asp Leu Asn Phe Gly Phe Lys Arg Gly
    1115                1120                1125

Arg Phe Lys Val Glu Lys Gln Val Tyr Gln Lys Leu Glu Lys Met
    1130                1135                1140

Leu Ile Glu Lys Leu Asn Tyr Leu Val Phe Lys Asp Asn Glu Phe
    1145                1150                1155

Asp Lys Thr Gly Gly Val Leu Arg Ala Tyr Gln Leu Thr Ala Pro
    1160                1165                1170

Phe Glu Thr Phe Lys Lys Met Gly Lys Gln Thr Gly Ile Ile Tyr
    1175                1180                1185

Tyr Val Pro Ala Gly Phe Thr Ser Lys Ile Cys Pro Val Thr Gly
    1190                1195                1200

Phe Val Asn Gln Leu Tyr Pro Lys Tyr Glu Ser Val Ser Lys Ser
    1205                1210                1215

Gln Glu Phe Phe Ser Lys Phe Asp Lys Ile Cys Tyr Asn Leu Asp
    1220                1225                1230

Lys Gly Tyr Phe Glu Phe Ser Phe Asp Tyr Lys Asn Phe Gly Asp
    1235                1240                1245

Lys Ala Ala Lys Gly Lys Trp Thr Ile Ala Ser Phe Gly Ser Arg
    1250                1255                1260

Leu Ile Asn Phe Arg Asn Ser Asp Lys Asn His Asn Trp Asp Thr
    1265                1270                1275

Arg Glu Val Tyr Pro Thr Lys Glu Leu Glu Lys Leu Leu Lys Asp
    1280                1285                1290

Tyr Ser Ile Glu Tyr Gly His Gly Glu Cys Ile Lys Ala Ala Ile
    1295                1300                1305

Cys Gly Glu Ser Asp Lys Lys Phe Phe Ala Lys Leu Thr Ser Val
```

| | | | | | | | | | | |
|---|---|---|---|---|---|---|---|---|---|---|
| | | 1310 | | | 1315 | | | | 1320 | |
| Leu | Asn | Thr | Ile | Leu | Gln | Met | Arg | Asn | Ser | Lys | Thr | Gly | Thr | Glu |
| | 1325 | | | | 1330 | | | | 1335 | |

Leu Asp Tyr Leu Ile Ser Pro Val Ala Asp Val Asn Gly Asn Phe
    1340                1345                1350

Phe Asp Ser Arg Gln Ala Pro Lys Asn Met Pro Gln Asp Ala Asp
    1355                1360                1365

Ala Asn Gly Ala Tyr His Ile Gly Leu Lys Gly Leu Met Leu Leu
    1370                1375                1380

Gly Arg Ile Lys Asn Asn Gln Glu Gly Lys Lys Leu Asn Leu Val
    1385                1390                1395

Ile Lys Asn Glu Glu Tyr Phe Glu Phe Val Gln Asn Arg Asn Asn
    1400                1405                1410

<210> SEQ ID NO 24
<211> LENGTH: 4293
<212> TYPE: DNA
<213> ORGANISM: Artificial Sequence
<220> FEATURE:
<223> OTHER INFORMATION: Synthetic sequence. FnCas12a:Linker:PCV

<400> SEQUENCE: 24

```
agtatctacc aggagttcgt gaacaaatac tccctgagca aaaccctgcg ctttgaactg      60
atcccgcagg gtaaaactct ggaaaacatc aaagctcgcg gcctgattct ggacgatgaa     120
aaacgcgcga agattacaa aaaagcgaaa cagatcatcg ataaatacca ccagttcttc     180
atcgaagaga tcctgtcttc tgtgtgcatc agcgaggacc tcctgcagaa ctatagcgat     240
gtctacttca aactgaaaaa gagcgatgac gacaacctcc agaaagattt caaaagcgcc     300
aaagacacca ttaagaagca gatctccgaa tacattaagg attctgagaa atttaaaaac     360
ctcttcaacc agaacctgat cgacgcgaaa aaaggccagg agagcgatct gattctgtgg     420
ctgaaacagt ccaaggataa cggtattgaa cttttttaagg ctaactctga catcactgac     480
atcgatgaag ccctggaaat catcaaatcc tttaaaggtt ggaccactta cttcaaaggt     540
ttccatgaaa tcgcaaaaaa cgtttatagc tctaacgata ttccgacatc catcatctac     600
cgcatcgttg atgacaactt gccgaaattc ctggaaaaca aggctaaata tgaatccctg     660
aaagacaaag cgccggaagc aatcaattat gaacagatta aaaagacct ggctgaagaa     720
ctgaccttcg acatcgacta caaaaccagc gaggttaacc agcgcgtatt ctctctggac     780
gaagtcttcg agatcgctaa cttcaacaac tacctgaacc agtccggcat cacgaaattc     840
aacaccatta tcggcggcaa atttgtgaac ggcgaaaaca ctaaacgtaa aggcatcaat     900
gagtacatca atctgtactc ccagcagatt aatgataaaa cactgaagaa atataaaatg     960
agcgtgctgt tcaaacagat cctctctgat accgaaagca gagcttcgt tatcgataaa    1020
cttgaagacg atagcgatgt tgttactacc atgcagtcct tctatgagca gatcgcagct    1080
tttaaaaccg ttgaagaaaa atccatcaaa gaaaccttat ccctgctgtt cgatgatctg    1140
aaagcacaga aacttgacct gtccaaaatt tacttcaaaa acgacaaaag cctgaccgat    1200
ttaagccagc aggtgttcga tgattatagc gtgattggga cggcagtgct ggaatacatc    1260
acccaacaaa tcgcgccgaa aaacctggac aacccatcta aaaagagcca ggagctgatt    1320
gcgaaaaaga ctgaaaaagc taaatatctg tccctggaga ccatcaaact ggcgctggag    1380
gagtttaaca gcatcgcga tattgataag cagtgccgtt tgaagaaat cctggcgaac    1440
ttcgcagcga tcccaatgat ttttgacgaa atcgcacaga acaaagataa cctggcgcag    1500
```

```
atcagcatca aataccagaa ccagggtaag aaggacctgc tgcaggcatc ggccgaagat    1560
gatgttaaag caatcaaaga tctcttggat caaaccaata acctgctgca caaactgaaa    1620
atcttccaca tttcccagtc tgaagataag gcgaacattc tggataaaga tgaacacttc    1680
tatctcgtat ttgaggaatg ttatttcgag ctggcaaaca tcgttccgct gtacaacaaa    1740
atccgtaact acatcaccca gaaaccgtac agcgacgaaa aattcaagct gaatttcgaa    1800
aatagcacct tagcgaatgg ttgggacaaa aataaagaac ctgacaacac cgcgatcctg    1860
ttcatcaaag atgataaata ctacctgggc gtaatgaaca aaagaacaa caaaatcttt    1920 gacgacaaag cgattaaaga aaacaaaggc gaaggctata aaaagatcgt gtataagctg    1980
ctgccgggtg cgaacaagat gctgccgaag gtattcttct ctgccaaaag catcaaattc    2040
tataacccgt cggaagacat tctgcgcatc cgtaaccact cgacacatac caaaaatggc    2100
tccccccaga aaggttacga aaaatttgag ttcaacattg aagattgtcg taaatttatc    2160
gacttttaca aacagagcat cagtaaacat ccggaatgga aagattttgg cttccgcttt    2220
tcggataccc agcgttacaa ctccatcgac gagttctacc gcgaagttga aaaccagggt    2280
tacaaactga ctttcgaaaa catctcggag tcttacatcg attctgttgt taaccagggt    2340
aaactgtacc tgttccaaat ctacaacaag gacttctcag cctacagcaa aggccgcccg    2400
aatctgcata ccctgtattg gaaagcgctc ttcgatgaac gtaacctgca ggatgtggtt    2460
tacaaactga atggtgaagc tgaactcttt tatcgtaaac agtcaatccc gaagaaaatc    2520
acccacccgg caaaggaagc gattgccaac aaaaacaagg acaaccctaa gaaggaaagc    2580
gtgttcgaat acgatctgat taaagacaag cgcttcacgg aagacaaatt cttttttccac    2640 tgcccgatca ccattaactt taaatctagc ggggctaaca aattcaacga tgaaatcaac    2700
ttacttctga agaaaaagc taacgacgtt catattctca gtattgaccg gggcgaacgt    2760
catctggcat actacaccct ggttgacggc aaaggcaaca tcattaagca ggacacattc    2820
aacatcatcg gcaacgatcg tatgaaaact aattaccacg ataaactggc ggcgatcgag    2880
aaagatcgtg atagcgctcg taaggactgg aaaaagatca acaacattaa agaaatgaag    2940
gaaggttacc tgagccaggt tgtgcatgaa atcgcaaaac tggtcatcga atataacgcg    3000
atcgtcgtct ttgaagacct gaacttcggt tttaaacgtg gtcgcttcaa agtcgaaaaa    3060
caggtgtacc agaagctgga gaaaatgctg atcgaaaaac tgaactatct ggtattcaaa    3120
gataacgaat ttgataaaac cggtggtgtc ctccgtgctt accaactgac cgctccttc    3180 gaaaccttta agaaaatggg taagcagacc ggcattatct actatgtgcc agcaggcttc    3240
acctctaaaa tttgcccggt caccggcttt gtcaaccaac tgtacccaaa atacgaatct    3300
gtgagcaaat cccaggaatt tttcagcaaa ttcgataaaa tttgttacaa cctggataaa    3360
ggctattttg aatttagctt tgactacaaa aactttggcg ataaagctgc aaaaggtaaa    3420
tggaccatcg cgagtttcgg ttctcgtctg atcaacttcc gcaacagcga taaaaccat    3480 aactgggaca ctcgtgaagt ttacccgacc aaggaattag aaaaactgct caaagattac    3540
agtatcgaat acggccacgg tgaatgtatc aaagcagcaa tctgcggtga gtctgataaa    3600 aaattttcg cgaaactgac gtctgtactg aacactattc tgcagatgcg taactccaaa    3660
accggtaccg aactggacta cctgatcagc ccggttgcgg acgttaatgg taacttttc    3720 gacagccgtc aggcaccgaa aaacatgcct caggatgcgg acgccaacgg cgcgtaccac    3780
atcggcctga aaggcctgat gttgctgggt cgcatcaaaa ataaccagga aggcaaaaaa    3840
```

-continued

```
ctgaacctgg tgattaaaaa tgaagaatac tttgagttcg tgcagaaccg taataactct   3900
gcttctgata ctggtggttc ttctgaaact ggtactttag attctagccc gagcaaaaaa   3960
aacggccgca gcggcccgca gccgcataaa cgctgggtgt ttaccctgaa caacccgagc   4020
gaagatgaac gcaaaaaaat tcgcgatctg ccgattagcc tgtttgatta ttttattgtg   4080
ggcgaagaag caacgaaga aggccgcacc ccgcatctgc agggctttgc gaactttgtg   4140
aaaaaacaga cctttaacaa agtgaaatgg tatctgggcg cgcgctgcca tattgaaaaa   4200
gcgaaaggca ccgatcagca gaacaaagaa tattgcagca aagaaggcaa cctgctgatg   4260
gaatgcggcg cgccgcgcag ccagggccag cgc                                4293
```

```
<210> SEQ ID NO 25
<211> LENGTH: 1431
<212> TYPE: PRT
<213> ORGANISM: Artificial Sequence
<220> FEATURE:
<223> OTHER INFORMATION: Synthetic sequence. FnCas12a:Linker:PCV

<400> SEQUENCE: 25

Ser Ile Tyr Gln Glu Phe Val Asn Lys Tyr Ser Leu Ser Lys Thr Leu
1               5                   10                  15

Arg Phe Glu Leu Ile Pro Gln Gly Lys Thr Leu Glu Asn Ile Lys Ala
            20                  25                  30

Arg Gly Leu Ile Leu Asp Asp Glu Lys Arg Ala Lys Asp Tyr Lys Lys
        35                  40                  45

Ala Lys Gln Ile Ile Asp Lys Tyr His Gln Phe Phe Ile Glu Glu Ile
    50                  55                  60

Leu Ser Ser Val Cys Ile Ser Glu Asp Leu Leu Gln Asn Tyr Ser Asp
65                  70                  75                  80

Val Tyr Phe Lys Leu Lys Lys Ser Asp Asp Asn Leu Gln Lys Asp
                85                  90                  95

Phe Lys Ser Ala Lys Asp Thr Ile Lys Lys Gln Ile Ser Glu Tyr Ile
            100                 105                 110

Lys Asp Ser Glu Lys Phe Lys Asn Leu Phe Asn Gln Asn Leu Ile Asp
        115                 120                 125

Ala Lys Lys Gly Gln Glu Ser Asp Leu Ile Leu Trp Leu Lys Gln Ser
    130                 135                 140

Lys Asp Asn Gly Ile Glu Leu Phe Lys Ala Asn Ser Asp Ile Thr Asp
145                 150                 155                 160

Ile Asp Glu Ala Leu Glu Ile Ile Lys Ser Phe Lys Gly Trp Thr Thr
                165                 170                 175

Tyr Phe Lys Gly Phe His Glu Asn Arg Lys Asn Val Tyr Ser Ser Asn
            180                 185                 190

Asp Ile Pro Thr Ser Ile Ile Tyr Arg Ile Val Asp Asp Asn Leu Pro
        195                 200                 205

Lys Phe Leu Glu Asn Lys Ala Lys Tyr Glu Ser Leu Lys Asp Lys Ala
    210                 215                 220

Pro Glu Ala Ile Asn Tyr Glu Gln Ile Lys Lys Asp Leu Ala Glu Glu
225                 230                 235                 240

Leu Thr Phe Asp Ile Asp Tyr Lys Thr Ser Glu Val Asn Gln Arg Val
                245                 250                 255

Phe Ser Leu Asp Glu Val Phe Glu Ile Ala Asn Phe Asn Asn Tyr Leu
            260                 265                 270

Asn Gln Ser Gly Ile Thr Lys Phe Asn Thr Ile Ile Gly Gly Lys Phe
        275                 280                 285
```

```
Val Asn Gly Glu Asn Thr Lys Arg Lys Gly Ile Asn Glu Tyr Ile Asn
        290                 295                 300

Leu Tyr Ser Gln Gln Ile Asn Asp Lys Thr Leu Lys Lys Tyr Lys Met
305                 310                 315                 320

Ser Val Leu Phe Lys Gln Ile Leu Ser Asp Thr Glu Ser Lys Ser Phe
                325                 330                 335

Val Ile Asp Lys Leu Glu Asp Asp Ser Asp Val Val Thr Thr Met Gln
                340                 345                 350

Ser Phe Tyr Glu Gln Ile Ala Ala Phe Lys Thr Val Glu Glu Lys Ser
                355                 360                 365

Ile Lys Glu Thr Leu Ser Leu Phe Asp Asp Leu Lys Ala Gln Lys
        370                 375                 380

Leu Asp Leu Ser Lys Ile Tyr Phe Lys Asn Asp Lys Ser Leu Thr Asp
385                 390                 395                 400

Leu Ser Gln Gln Val Phe Asp Asp Tyr Ser Val Ile Gly Thr Ala Val
                405                 410                 415

Leu Glu Tyr Ile Thr Gln Gln Ile Ala Pro Lys Asn Leu Asp Asn Pro
                420                 425                 430

Ser Lys Lys Glu Gln Glu Leu Ile Ala Lys Lys Thr Glu Lys Ala Lys
                435                 440                 445

Tyr Leu Ser Leu Glu Thr Ile Lys Leu Ala Leu Glu Glu Phe Asn Lys
450                 455                 460

His Arg Asp Ile Asp Lys Gln Cys Arg Phe Glu Glu Ile Leu Ala Asn
465                 470                 475                 480

Phe Ala Ala Ile Pro Met Ile Phe Asp Glu Ile Ala Gln Asn Lys Asp
                485                 490                 495

Asn Leu Ala Gln Ile Ser Ile Lys Tyr Gln Asn Gln Gly Lys Lys Asp
                500                 505                 510

Leu Leu Gln Ala Ser Ala Glu Asp Asp Val Lys Ala Ile Lys Asp Leu
                515                 520                 525

Leu Asp Gln Thr Asn Asn Leu Leu His Lys Leu Lys Ile Phe His Ile
        530                 535                 540

Ser Gln Ser Glu Asp Lys Ala Asn Ile Leu Asp Lys Asp Glu His Phe
545                 550                 555                 560

Tyr Leu Val Phe Glu Glu Cys Tyr Phe Glu Leu Ala Asn Ile Val Pro
                565                 570                 575

Leu Tyr Asn Lys Ile Arg Asn Tyr Ile Thr Gln Lys Pro Tyr Ser Asp
                580                 585                 590

Glu Lys Phe Lys Leu Asn Phe Glu Asn Ser Thr Leu Ala Asn Gly Trp
        595                 600                 605

Asp Lys Asn Lys Glu Pro Asp Asn Thr Ala Ile Leu Phe Ile Lys Asp
610                 615                 620

Asp Lys Tyr Tyr Leu Gly Val Met Asn Lys Lys Asn Asn Lys Ile Phe
625                 630                 635                 640

Asp Asp Lys Ala Ile Lys Glu Asn Lys Gly Glu Gly Tyr Lys Lys Ile
                645                 650                 655

Val Tyr Lys Leu Leu Pro Gly Ala Asn Lys Met Leu Pro Lys Val Phe
                660                 665                 670

Phe Ser Ala Lys Ser Ile Lys Phe Tyr Asn Pro Ser Glu Asp Ile Leu
        675                 680                 685

Arg Ile Arg Asn His Ser Thr His Thr Lys Asn Gly Ser Pro Gln Lys
        690                 695                 700
```

Gly Tyr Glu Lys Phe Glu Phe Asn Ile Glu Asp Cys Arg Lys Phe Ile
705                 710                 715                 720

Asp Phe Tyr Lys Gln Ser Ile Ser Lys His Pro Glu Trp Lys Asp Phe
            725                 730                 735

Gly Phe Arg Phe Ser Asp Thr Gln Arg Tyr Asn Ser Ile Asp Glu Phe
        740                 745                 750

Tyr Arg Glu Val Glu Asn Gln Gly Tyr Lys Leu Thr Phe Glu Asn Ile
    755                 760                 765

Ser Glu Ser Tyr Ile Asp Ser Val Val Asn Gln Gly Lys Leu Tyr Leu
770                 775                 780

Phe Gln Ile Tyr Asn Lys Asp Phe Ser Ala Tyr Ser Lys Gly Arg Pro
785                 790                 795                 800

Asn Leu His Thr Leu Tyr Trp Lys Ala Leu Phe Asp Glu Arg Asn Leu
            805                 810                 815

Gln Asp Val Val Tyr Lys Leu Asn Gly Glu Ala Glu Leu Phe Tyr Arg
        820                 825                 830

Lys Gln Ser Ile Pro Lys Ile Thr His Pro Ala Lys Glu Ala Ile
    835                 840                 845

Ala Asn Lys Asn Lys Asp Asn Pro Lys Lys Glu Ser Val Phe Glu Tyr
850                 855                 860

Asp Leu Ile Lys Asp Lys Arg Phe Thr Glu Asp Lys Phe Phe Phe His
865                 870                 875                 880

Cys Pro Ile Thr Ile Asn Phe Lys Ser Ser Gly Ala Asn Lys Phe Asn
            885                 890                 895

Asp Glu Ile Asn Leu Leu Leu Lys Glu Lys Ala Asn Asp Val His Ile
        900                 905                 910

Leu Ser Ile Asp Arg Gly Glu Arg His Leu Ala Tyr Tyr Thr Leu Val
    915                 920                 925

Asp Gly Lys Gly Asn Ile Ile Lys Gln Asp Thr Phe Asn Ile Ile Gly
930                 935                 940

Asn Asp Arg Met Lys Thr Asn Tyr His Asp Lys Leu Ala Ala Ile Glu
945                 950                 955                 960

Lys Asp Arg Asp Ser Ala Arg Lys Asp Trp Lys Lys Ile Asn Asn Ile
            965                 970                 975

Lys Glu Met Lys Glu Gly Tyr Leu Ser Gln Val Val His Glu Ile Ala
        980                 985                 990

Lys Leu Val Ile Glu Tyr Asn Ala Ile Val Val Phe Glu Asp Leu Asn
    995                 1000                1005

Phe Gly Phe Lys Arg Gly Arg Phe Lys Val Glu Lys Gln Val Tyr
    1010                1015                1020

Gln Lys Leu Glu Lys Met Leu Ile Glu Lys Leu Asn Tyr Leu Val
    1025                1030                1035

Phe Lys Asp Asn Glu Phe Asp Lys Thr Gly Gly Val Leu Arg Ala
    1040                1045                1050

Tyr Gln Leu Thr Ala Pro Phe Glu Thr Phe Lys Lys Met Gly Lys
    1055                1060                1065

Gln Thr Gly Ile Ile Tyr Tyr Val Pro Ala Gly Phe Thr Ser Lys
    1070                1075                1080

Ile Cys Pro Val Thr Gly Phe Val Asn Gln Leu Tyr Pro Lys Tyr
    1085                1090                1095

Glu Ser Val Ser Lys Ser Gln Glu Phe Phe Ser Lys Phe Asp Lys
    1100                1105                1110

Ile Cys Tyr Asn Leu Asp Lys Gly Tyr Phe Glu Phe Ser Phe Asp

| | | | | | | | | | | | | | |
|---|---|---|---|---|---|---|---|---|---|---|---|---|---|
| | | 1115 | | | | 1120 | | | | 1125 | | | |
| Tyr | Lys | Asn | Phe | Gly | Asp | Lys | Ala | Ala | Lys | Gly | Lys | Trp | Thr | Ile |
| | | 1130 | | | | 1135 | | | | 1140 | | | |
| Ala | Ser | Phe | Gly | Ser | Arg | Leu | Ile | Asn | Phe | Arg | Asn | Ser | Asp | Lys |
| | | 1145 | | | | 1150 | | | | 1155 | | | |
| Asn | His | Asn | Trp | Asp | Thr | Arg | Glu | Val | Tyr | Pro | Thr | Lys | Glu | Leu |
| | | 1160 | | | | 1165 | | | | 1170 | | | |
| Glu | Lys | Leu | Leu | Lys | Asp | Tyr | Ser | Ile | Glu | Tyr | Gly | His | Gly | Glu |
| | | 1175 | | | | 1180 | | | | 1185 | | | |
| Cys | Ile | Lys | Ala | Ala | Ile | Cys | Gly | Glu | Ser | Asp | Lys | Lys | Phe | Phe |
| | | 1190 | | | | 1195 | | | | 1200 | | | |
| Ala | Lys | Leu | Thr | Ser | Val | Leu | Asn | Thr | Ile | Leu | Gln | Met | Arg | Asn |
| | | 1205 | | | | 1210 | | | | 1215 | | | |
| Ser | Lys | Thr | Gly | Thr | Glu | Leu | Asp | Tyr | Leu | Ile | Ser | Pro | Val | Ala |
| | | 1220 | | | | 1225 | | | | 1230 | | | |
| Asp | Val | Asn | Gly | Asn | Phe | Phe | Asp | Ser | Arg | Gln | Ala | Pro | Lys | Asn |
| | | 1235 | | | | 1240 | | | | 1245 | | | |
| Met | Pro | Gln | Asp | Ala | Asp | Ala | Asn | Gly | Ala | Tyr | His | Ile | Gly | Leu |
| | | 1250 | | | | 1255 | | | | 1260 | | | |
| Lys | Gly | Leu | Met | Leu | Leu | Gly | Arg | Ile | Lys | Asn | Asn | Gln | Glu | Gly |
| | | 1265 | | | | 1270 | | | | 1275 | | | |
| Lys | Lys | Leu | Asn | Leu | Val | Ile | Lys | Asn | Glu | Glu | Tyr | Phe | Glu | Phe |
| | | 1280 | | | | 1285 | | | | 1290 | | | |
| Val | Gln | Asn | Arg | Asn | Asn | Ser | Ala | Ser | Asp | Thr | Gly | Gly | Ser | Ser |
| | | 1295 | | | | 1300 | | | | 1305 | | | |
| Glu | Thr | Gly | Thr | Leu | Asp | Ser | Ser | Pro | Ser | Lys | Lys | Asn | Gly | Arg |
| | | 1310 | | | | 1315 | | | | 1320 | | | |
| Ser | Gly | Pro | Gln | Pro | His | Lys | Arg | Trp | Val | Phe | Thr | Leu | Asn | Asn |
| | | 1325 | | | | 1330 | | | | 1335 | | | |
| Pro | Ser | Glu | Asp | Glu | Arg | Lys | Lys | Ile | Arg | Asp | Leu | Pro | Ile | Ser |
| | | 1340 | | | | 1345 | | | | 1350 | | | |
| Leu | Phe | Asp | Tyr | Phe | Ile | Val | Gly | Glu | Glu | Gly | Asn | Glu | Glu | Gly |
| | | 1355 | | | | 1360 | | | | 1365 | | | |
| Arg | Thr | Pro | His | Leu | Gln | Gly | Phe | Ala | Asn | Phe | Val | Lys | Lys | Gln |
| | | 1370 | | | | 1375 | | | | 1380 | | | |
| Thr | Phe | Asn | Lys | Val | Lys | Trp | Tyr | Leu | Gly | Ala | Arg | Cys | His | Ile |
| | | 1385 | | | | 1390 | | | | 1395 | | | |
| Glu | Lys | Ala | Lys | Gly | Thr | Asp | Gln | Gln | Asn | Lys | Glu | Tyr | Cys | Ser |
| | | 1400 | | | | 1405 | | | | 1410 | | | |
| Lys | Glu | Gly | Asn | Leu | Leu | Met | Glu | Cys | Gly | Ala | Pro | Arg | Ser | Gln |
| | | 1415 | | | | 1420 | | | | 1425 | | | |
| Gly | Gln | Arg | | | | | | | | | | | | |
| | | 1430 | | | | | | | | | | | | |

<210> SEQ ID NO 26
<211> LENGTH: 1228
<212> TYPE: PRT
<213> ORGANISM: Lachnospiraceae bacterium ND2006
<220> FEATURE:
<223> OTHER INFORMATION: LbCas12a

<400> SEQUENCE: 26

| | | | | | | | | | | | | | | |
|---|---|---|---|---|---|---|---|---|---|---|---|---|---|---|
| Met | Ser | Lys | Leu | Glu | Lys | Phe | Thr | Asn | Cys | Tyr | Ser | Leu | Ser | Lys |
| 1 | | | | 5 | | | | | 10 | | | | | 15 |
| Leu | Arg | Phe | Lys | Ala | Ile | Pro | Val | Gly | Lys | Thr | Gln | Glu | Asn | Ile | Asp |

```
            20                  25                  30
Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
        210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
        290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
        370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445
```

```
Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
            485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
            530                 535                 540

Thr Ile Leu Arg Tyr Gly Ser Lys Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
            835                 840                 845

Asn Ile Val Glu Gln Tyr Ser Leu Asn Glu Ile Ile Asn Asn Phe Asn
850                 855                 860
```

```
Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
            885                 890                 895

Lys Glu Leu Lys Ala Gly Tyr Ile Ser Gln Val Val His Lys Ile Cys
        900                 905                 910

Glu Leu Val Glu Lys Tyr Asp Ala Val Ile Ala Leu Glu Asp Leu Asn
            915                 920                 925

Ser Gly Phe Lys Asn Ser Arg Val Lys Val Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 27
<211> LENGTH: 12
<212> TYPE: DNA
<213> ORGANISM: Faba bean necrotic yellow virus
<220> FEATURE:
<223> OTHER INFORMATION: FBNYV HUH ori polynucleotide
```

```
<400> SEQUENCE: 27
tagtattacc cc                                                              12

<210> SEQ ID NO 28
<211> LENGTH: 22
<212> TYPE: DNA
<213> ORGANISM: Escherichia coli
<220> FEATURE:
<223> OTHER INFORMATION: TraI HUH Ori polynucleotide

<400> SEQUENCE: 28
tttgcgtggg gtgtggtgct tt                                                   22
```

METHODS AND COMPOSITIONS TO PROMOTE TARGETED GENOME MODIFICATIONS USING HUH ENDONUCLEASES

CROSS REFERENCE TO RELATED APPLICATIONS

This application is a national stage application under 35 U.S.C. § 371 of International Application No. PCT/US2020/044501, filed internationally on Jul. 31, 2020, which claims priority to U.S. Provisional Application No. 62/882,266, filed Aug. 2, 2019, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052059100SEQLIST.TXT, date recorded: Feb. 1, 2022, size: 136,769 bytes).

FIELD

The present disclosure relates to compositions and methods related to using RNA-guided nucleases linked to HUH endonucleases to improve targeted integrations of desired sequences into genomes.

INCORPORATION OF SEQUENCE LISTING

A sequence listing contained in the file named 46-21-63706_US0001_SEQ, which is 133 kilobytes (measured in MS-Windows®) and created on Jul. 17, 2020, and comprises 28 sequences, is filed electronically herewith and incorporated by reference in its entirety.

BACKGROUND

CRISPR (Clustered Regularly Interspaced Short Palindromic Repeats) nucleases (e.g., Cas12a, CasX, Cas9) are proteins guided by guide RNAs to a target nucleic acid molecule, where the nuclease can cleave one or two strands of a target nucleic acid molecule. HUH endonucleases are nucleases comprising a HUH (histidine-hydrophobic amino acid-histidine) tag that can form covalent bonds with specific single-stranded DNA sequences.

This disclosure demonstrates that Cas12a nucleases can be tethered to a HUH endonuclease using a novel linker amino acid to improve site-directed integration of a template sequence into a target DNA molecule.

BRIEF DESCRIPTION OF DRAWINGS

FIG. 1A depicts a graphical representation of an RNA-guided nuclease (Cas12a; equivalent to Cas12a) and a histidine-hydrophobic-histidine endonuclease (HUH EN) tethered to a single-stranded DNA (ssDNA) template comprising an HUH recognition sequence (ori) to increase cleavage (scissors) of double-stranded (ds) chromosomal DNA. FIG. 1B depicts a graphical representation of a C-terminal cys-free LbCas12a:HUH fusion expression construct and an N-terminal HUH:cys-free LbCas12a fusion expression construct.

SUMMARY

Figure 1:
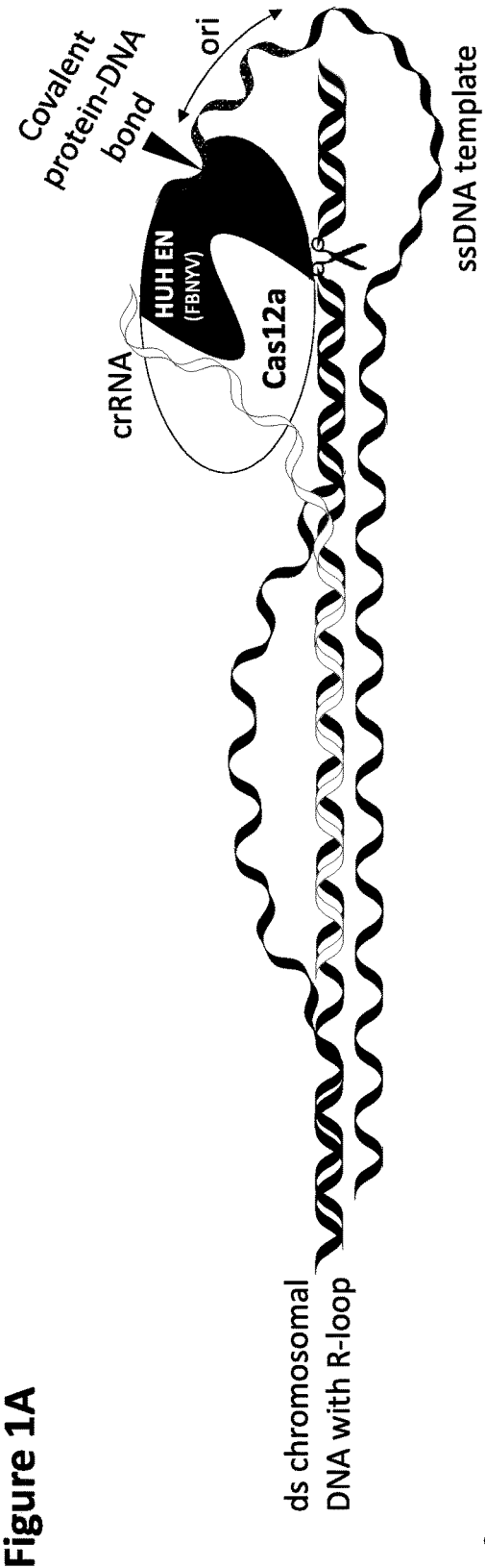
FIG. 1 comprises panels 1A and 1B.
Figure 1:
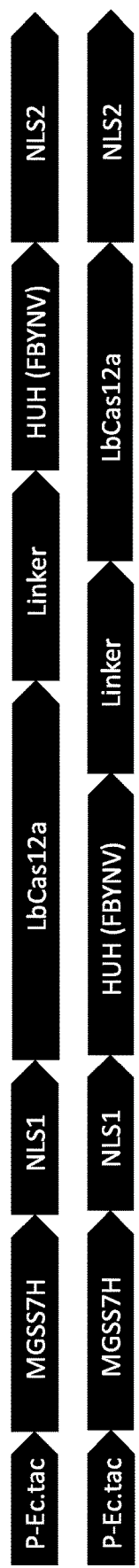

In one aspect, this disclosure provides a ribonucleoprotein comprising: (a) a recombinant polypeptide comprising: (i) an amino acid sequence encoding a Cas12a nuclease; (ii) an amino acid sequence encoding a linker; and (iii) an amino acid sequence encoding a HUH nuclease; and (b) at least one guide nucleic acid.

In one aspect, this disclosure provides a recombinant nucleic acid comprising: (a) a first nucleic acid sequence encoding a Cas12a nuclease; (b) a second nucleic acid sequence encoding a linker; and (c) a third nucleic acid sequence encoding a HUH nuclease.

In one aspect, this disclosure provides a method of generating an edit in a target DNA molecule comprising contacting the target DNA molecule with a ribonucleoprotein, where the ribonucleoprotein comprises: (a) a recombinant polypeptide comprising: (i) an amino acid sequence encoding a Cas12a nuclease; (ii) an amino acid sequence encoding a linker; and (iii) an amino acid sequence encoding a HUH nuclease; (b) at least one guide nucleic acid; and (c) at least one template nucleic acid molecule, where the ribonucleoprotein generates at least one edit in the target DNA molecule.

In one aspect, this disclosure provides a method of generating an edit in a target DNA molecule comprising providing to a cell: (a) a recombinant polypeptide comprising: (i) an amino acid sequence encoding a Cas12a nuclease; (ii) an amino acid sequence encoding a linker; and (iii) an amino acid sequence encoding a HUH nuclease, or one or more nucleic acid molecules encoding the recombinant polypeptide; (b) at least one guide nucleic acid, or at least one nucleic acid molecule encoding the at least one guide nucleic acid; and (c) at least one template nucleic acid molecule, or at least one nucleic acid molecule encoding the at least one template nucleic acid molecule, where the recombinant polypeptide, at least one guide nucleic acid, and at least one template nucleic acid molecule form a ribonucleoprotein, and where the ribonucleoprotein generates at least one edit in the target DNA molecule within the cell.

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of this disclosure includes, unless otherwise indicated, conventional techniques of biochemistry, chemistry, molecular biology, microbiology, cell biology, plant biology, genomics, biotechnology, and genetics, which are within the skill of the art. See, for example, Green and Sambrook, Molecular Cloning: A Laboratory Manual, 4th edition (2012); Current Protocols In Molecular Biology (F. M. Ausubel, et al. eds., (1987)); Plant Breeding Methodology (N. F. Jensen, Wiley-Interscience (1988)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc.

As used herein, terms in the singular and the singular forms "a," "an," and "the," for example, include plural referents unless the content clearly dictates otherwise.

Any composition, nucleic acid molecule, polypeptide, cell, plant, etc. provided herein is specifically envisioned for use with any method provided herein.

In an aspect, this disclosure provides a ribonucleoprotein comprising (a) a recombinant polypeptide comprising: (i) an amino acid sequence encoding a Cas12a nuclease; (ii) an amino acid sequence encoding a linker; and (iii) an amino acid sequence encoding a HUH endonuclease; and (b) at least one guide nucleic acid. In an aspect, a ribonucleoprotein further comprises at least one template nucleic acid molecule.

In an aspect, this disclosure provides a ribonucleoprotein comprising (a) a recombinant polypeptide comprising: (i) an amino acid sequence encoding a CasX nuclease; (ii) an amino acid sequence encoding a linker; and (iii) an amino acid sequence encoding a HUH endonuclease; and (b) at least one guide nucleic acid. In an aspect, a ribonucleoprotein further comprises at least one template nucleic acid molecule.

In an aspect, this disclosure provides a recombinant nucleic acid comprising: (a) a first nucleic acid sequence encoding a Cas12a nuclease; (b) a second nucleic acid sequence encoding a linker; and (c) a third nucleic acid sequence encoding a HUH endonuclease. In an aspect, this disclosure provides a recombinant nucleic acid comprising: (a) a first nucleic acid sequence encoding a CasX nuclease; (b) a second nucleic acid sequence encoding a linker; and (c) a third nucleic acid sequence encoding a HUH endonuclease. In an aspect, a recombinant nucleic acid further comprises (d) a fourth nucleic acid sequence encoding at least one guide nucleic acid. In an aspect, a recombinant nucleic acid further comprises (d) a fourth nucleic acid sequence encoding at least one template nucleic acid molecule. In another aspect, a recombinant nucleic acid further comprises (d) a fourth nucleic acid sequence encoding at least one guide nucleic acid; and (e) a fifth nucleic acid sequence encoding at least one template nucleic acid molecule.

CRISPR (Clustered Regularly Interspaced Short Palindromic Repeats) nucleases (e.g., Cas9, CasX, Cas12a (also referred to as Cpf1), CasY) are proteins found in bacteria that are guided by guide RNAs ("gRNAs") to a target nucleic acid molecule, where the endonuclease can then cleave one or two strands the target nucleic acid molecule. Although the origins of CRISPR nucleases are bacterial, many CRISPR nucleases have been shown to function in eukaryotic cells.

While not being limited by any particular scientific theory, a CRISPR nuclease forms a complex with a guide RNA (gRNA), which hybridizes with a complementary target site, thereby guiding the CRISPR nuclease to the target site. In class II CRISPR-Cas systems, CRISPR arrays, including spacers, are transcribed during encounters with recognized invasive DNA and are processed into small interfering CRISPR RNAs (crRNAs). The crRNA comprises a repeat sequence and a spacer sequence which is complementary to a specific protospacer sequence in an invading pathogen. The spacer sequence can be designed to be complementary to target sequences in a eukaryotic genome.

CRISPR nucleases associate with their respective crRNAs in their active forms. CasX, similar to the class II endonuclease Cas9, requires another non-coding RNA component, referred to as a trans-activating crRNA (tracrRNA), to have functional activity. Nucleic acid molecules provided herein can combine a crRNA and a tracrRNA into one nucleic acid molecule in what is herein referred to as a "single guide RNA" (sgRNA). Cas12a does not require a tracrRNA to be guided to a target site; a crRNA alone is sufficient for Cas12a. The gRNA guides the active CRISPR nuclease complex to a target site, where the CRISPR nuclease can cleave the target site.

When an RNA-guided CRISPR nuclease and a guide RNA form a complex, the whole system is called a "ribonucleoprotein." Ribonucleoproteins provided herein can also comprise additional nucleic acids, such as, without being limiting, template nucleic acid molecules. Ribonucleoproteins provided herein can also comprise additional proteins, such as linkers and HUH endonucleases.

A prerequisite for cleavage of the target site by a CRISPR ribonucleoprotein is the presence of a conserved Protospacer Adjacent Motif (PAM) near the target site. Depending on the CRISPR nuclease, cleavage can occur within a certain number of nucleotides (e.g., between 18-23 nucleotides for Cas12a) from the PAM site. PAM sites are only required for type I and type II CRISPR associated proteins, and different CRISPR endonucleases recognize different PAM sites. Without being limiting, Cas12a can recognize at least the following PAM sites: TTTN, and YTN; and CasX can recognize at least the following PAM sites: TTCN, TTCA, and TTC (where T is thymine; C is cytosine; A is adenine; Y is thymine or cytosine; and N is thymine, cytosine, guanine, or adenine).

Cas12a is an RNA-guided nuclease of a class II, type V CRISPR/Cas system. Cas12a nucleases generate staggered cuts when cleaving a target nucleic acid molecule.

In an aspect, a Cas nuclease provided herein is a *Lachnospiraceae bacterium* Cas12a (LbCas12a) nuclease. In another aspect, a Cas12a nuclease provided herein is a *Francisella novicida* Cas12a (FnCas12a) nuclease. In some embodiments, the amino acid sequence of the Cas12a nuclease has been engineered to remove cysteines.

In an aspect, a Cas12a nuclease, or a nucleic acid encoding a Cas12a nuclease, is derived from a bacteria genus selected from the group consisting of *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium, Acidaminococcus, Peregrinibacteria, Butyrivibrio, Parcubacteria, Smithella, Candidatus, Moraxella,* and *Leptospira*.

In one embodiment, a Cas12a nuclease provided herein comprises an amino acid sequence at least 80% identical or similar to amino acid sequence disclosed in SEQ ID NO: 1 encoding a cys-free LbCas12a. As used herein, a "cys-free LbCas12a" refers to an LbCas12a protein variant wherein the 9 cysteines present in the native LbCas12a sequence (WO2016205711-1150) are all mutated. In an aspect the cys-free LbCas12a comprises the following 9 amino acid substitutions when compared to a wt LbCas12a protein sequence: C1OL, C175L, C565S, C632L, C805A, C912V, C965S, C1090P, C1116L. Cysteine residues in a protein are able to form disulfide bridges providing a strong reversible attachment between cysteines. To control and direct the attachment of Cas12a in a targeted manner the native cysteines are removed to control the formation of these bridges. Not wishing to be bound by a particular theory, removal of the cysteines from the protein backbone would enable targeted insertion of new cysteine residues to control the placement of these reversible connections by a disulfide linkage. This could be between protein domains or to a particle such as a gold particle for biolistic delivery. A tag comprising several residues of cysteine could be added to the cys-free LbCas12a that would allow it to specifically attach to metal beads (specifically gold) in a uniform way.

In an aspect, a Cas12a nuclease provided herein comprises an amino acid sequence at least 80% identical or similar to an amino acid sequence selected from the group consisting of SEQ ID NOs: 1, 15 and 26. In another aspect, a Cas12a nuclease provided herein comprises an amino acid sequence at least 85% identical or similar to an amino acid sequence selected from the group consisting of SEQ ID NOs: 1,15 and 26. In another aspect, a Cas12a nuclease provided herein comprises an amino acid sequence at least 90% identical or similar to an amino acid sequence selected from the group consisting of SEQ ID NOs: 1,15 and 26. In another aspect, a Cas12a nuclease provided herein comprises an amino acid sequence at least 95% identical or similar to an amino acid sequence selected from the group consisting of SEQ ID NOs: 1,15 and 26. In another aspect, a Cas12a nuclease provided herein comprises an amino acid sequence at least 96% identical or similar to an amino acid sequence selected from the group consisting of SEQ ID NOs: 1,15 and 26. In another aspect, a Cas12a nuclease provided herein comprises an amino acid sequence at least 97% identical or similar to an amino acid sequence selected from the group consisting of SEQ ID NOs: 1,15 and 26. In another aspect, a Cas12a nuclease provided herein comprises an amino acid sequence at least 98% identical or similar to an amino acid sequence selected from the group consisting of SEQ ID NOs: 1,15 and 26. In another aspect, a Cas12a nuclease provided herein comprises an amino acid sequence at least 99% identical or similar to an amino acid sequence selected from the group consisting of SEQ ID NOs: 1,15 and 26. In another aspect, a Cas12a nuclease provided herein comprises an amino acid sequence 100% identical or similar to an amino acid sequence selected from the group consisting of SEQ ID NOs: 1,15 and 26.

In an aspect, a Cas12a nuclease is encoded by a polynucleotide comprising a sequence at least 80% identical to a polynucleotide selected from the group consisting of SEQ ID NOs: 4 and 16.

In another aspect, a Cas nuclease is encoded by a polynucleotide comprising a sequence at least 85% identical to a polynucleotide selected from the group consisting of SEQ ID NOs: 4 and 16. In another aspect, a Cas12a nuclease is encoded by a polynucleotide comprising a sequence at least 90% identical to a polynucleotide selected from the group consisting of SEQ ID NOs: 4 and 16. In another aspect, a Cas nuclease is encoded by a polynucleotide comprising a sequence at least 95% identical to a polynucleotide selected from the group consisting of SEQ ID NOs: 4 and 16. In another aspect, a Cas12a nuclease is encoded by a polynucleotide comprising a sequence at least 96% identical to a polynucleotide selected from the group consisting of SEQ ID NOs: 4 and 16. In another aspect, a Cas12a nuclease is encoded by a polynucleotide comprising a sequence at least 97% identical to a polynucleotide selected from the group consisting of SEQ ID NOs: 4 and 16. In another aspect, a Cas12a nuclease is encoded by a polynucleotide comprising a sequence at least 98% identical to a polynucleotide selected from the group consisting of SEQ ID NOs: 4 and 16. In another aspect, a Cas12a nuclease is encoded by a polynucleotide comprising a sequence at least 99% identical to a polynucleotide selected from the group consisting of SEQ ID NOs: 4 and 16. In another aspect, a Cas nuclease is encoded by a polynucleotide comprising a sequence 100% identical to a polynucleotide selected from the group consisting of SEQ ID NOs: 4 and 16.

CasX is a type of class II CRISPR-Cas nuclease that has been identified in the bacterial phyla Deltaproteobacteria and Planctomycetes. Similar to Cas12a, CasX nucleases generate staggered cuts when cleaving a target nucleic acid molecule. However, unlike Cas12a, CasX nucleases require a crRNA and a tracrRNA, or a single-guide RNA, in order to target and cleave a target nucleic acid.

In an aspect, a CasX nuclease provided herein is a CasX nuclease from the phylum Deltaproteobacteria. In another aspect, a CasX nuclease provided herein is a CasX nuclease from the phylum Planctomycetes. Additional suitable CasX nucleases are those set forth in WO 2019/084148, which is incorporated by reference herein in its entirety.

In an aspect, a Cas12a nuclease or CasX nuclease provided herein can be expressed from a recombinant vector in vivo. In an aspect, a Cas12a nuclease or CasX nuclease provided herein can be expressed from a recombinant vector in vitro. In an aspect, a Cas12a nuclease or CasX nuclease provided herein can be expressed from a recombinant vector ex vivo. In an aspect, a Cas12a nuclease or CasX nuclease provided herein can be expressed from a nucleic acid molecule in vivo. In an aspect, a Cas12a nuclease or CasX nuclease provided herein can be expressed from a nucleic acid molecule in vitro. In an aspect, a Cas12a nuclease or CasX nuclease provided herein can be expressed from a nucleic acid molecule ex vivo.

As used herein, a "guide nucleic acid" refers to a nucleic acid that forms a complex with a CRISPR nuclease (e.g., without being limiting, Cas12a, CasX) and then guides the complex to a specific sequence in a target nucleic acid molecule, where the guide nucleic acid and the target nucleic acid molecule share complementary sequences. In an aspect, a ribonucleoprotein provided herein comprises at least one guide nucleic acid.

In an aspect, a guide nucleic acid comprises DNA. In another aspect, a guide nucleic acid comprises RNA. In an aspect, a guide nucleic acid comprises DNA, RNA, or a combination thereof. In an aspect, a guide nucleic acid is single-stranded. In another aspect, a guide nucleic acid is at least partially double-stranded.

When a guide nucleic acid comprises RNA, it can be referred to as a "guide RNA." In another aspect, a guide nucleic acid comprises DNA and RNA. In another aspect, a guide nucleic acid is single-stranded. In another aspect, a guide nucleic acid is double-stranded. In a further aspect, a guide nucleic acid is partially double-stranded.

In another aspect, a guide nucleic acid comprises at least 10 nucleotides. In another aspect, a guide nucleic acid comprises at least 11 nucleotides. In another aspect, a guide nucleic acid comprises at least 12 nucleotides. In another aspect, a guide nucleic acid comprises at least 13 nucleotides. In another aspect, a guide nucleic acid comprises at least 14 nucleotides. In another aspect, a guide nucleic acid comprises at least 15 nucleotides. In another aspect, a guide nucleic acid comprises at least 16 nucleotides. In another aspect, a guide nucleic acid comprises at least 17 nucleotides. In another aspect, a guide nucleic acid comprises at least 18 nucleotides. In another aspect, a guide nucleic acid comprises at least 19 nucleotides. In another aspect, a guide nucleic acid comprises at least 20 nucleotides. In another aspect, a guide nucleic acid comprises at least 21 nucleotides. In another aspect, a guide nucleic acid comprises at least 22 nucleotides. In another aspect, a guide nucleic acid comprises at least 23 nucleotides. In another aspect, a guide nucleic acid comprises at least 24 nucleotides. In another aspect, a guide nucleic acid comprises at least 25 nucleotides. In another aspect, a guide nucleic acid comprises at least 26 nucleotides. In another aspect, a guide nucleic acid comprises at least 27 nucleotides. In another aspect, a guide nucleic acid comprises at least 28 nucleotides. In another aspect, a guide nucleic acid comprises at least 30 nucleotides. In another aspect, a guide nucleic acid comprises at least 35 nucleotides. In another aspect, a guide nucleic acid comprises at least 40 nucleotides. In another aspect, a guide nucleic acid comprises at least 45 nucleotides. In another aspect, a guide nucleic acid comprises at least 50 nucleotides.

In another aspect, a guide nucleic acid comprises between 10 nucleotides and 50 nucleotides. In another aspect, a guide nucleic acid comprises between 10 nucleotides and 40 nucleotides. In another aspect, a guide nucleic acid comprises between 10 nucleotides and 30 nucleotides. In another aspect, a guide nucleic acid comprises between 10 nucleotides and 20 nucleotides. In another aspect, a guide nucleic acid comprises between 16 nucleotides and 28 nucleotides. In another aspect, a guide nucleic acid comprises between 16 nucleotides and 25 nucleotides. In another aspect, a guide nucleic acid comprises between 16 nucleotides and 20 nucleotides.

In an aspect, a guide nucleic acid comprises at least 70% sequence complementarity to a target site. In an aspect, a guide nucleic acid comprises at least 75% sequence complementarity to a target site. In an aspect, a guide nucleic acid comprises at least 80% sequence complementarity to a target site. In an aspect, a guide nucleic acid comprises at least 85% sequence complementarity to a target site. In an aspect, a guide nucleic acid comprises at least 90% sequence complementarity to a target site. In an aspect, a guide nucleic acid comprises at least 91% sequence complementarity to a target site. In an aspect, a guide nucleic acid comprises at least 92% sequence complementarity to a target site. In an aspect, a guide nucleic acid comprises at least 93% sequence complementarity to a target site. In an aspect, a guide nucleic acid comprises at least 94% sequence complementarity to a target site. In an aspect, a guide nucleic acid comprises at least 95% sequence complementarity to a target site. In an aspect, a guide nucleic acid comprises at least 96% sequence complementarity to a target site. In an aspect, a guide nucleic acid comprises at least 97% sequence complementarity to a target site. In an aspect, a guide nucleic acid comprises at least 98% sequence complementarity to a target site. In an aspect, a guide nucleic acid comprises at least 99% sequence complementarity to a target site. In an aspect, a guide nucleic acid comprises 100% sequence complementarity to a target site. In another aspect, a guide nucleic acid comprises between 70% and 100% sequence complementarity to a target site. In another aspect, a guide nucleic acid comprises between 80% and 100% sequence complementarity to a target site. In another aspect, a guide nucleic acid comprises between 90% and 100% sequence complementarity to a target site.

In an aspect, a guide nucleic acid is capable of hybridizing to a target site.

As noted above, some RNA-guided CRISPR nucleases, such as CasX and Cas9, require another non-coding RNA component, referred to as a trans-activating crRNA (tracrRNA), to have functional activity. Guide nucleic acid molecules provided herein can combine a crRNA and a tracrRNA into one nucleic acid molecule in what is herein referred to as a "single guide RNA" (sgRNA). The gRNA guides the active CasX complex to a target site, where CasX can cleave the target site. In other embodiments, the crRNA and tracrRNA are provided as separate nucleic acid molecules.

In an aspect, a guide nucleic acid comprises a crRNA. In another aspect, a guide nucleic acid comprises a tracrRNA. In a further aspect, a guide nucleic acid comprises an sgRNA.

In an aspect, a guide nucleic acid provided herein can be expressed from a recombinant vector in vivo. In an aspect, a guide nucleic acid provided herein can be expressed from a recombinant vector in vitro. In an aspect, a guide nucleic acid provided herein can be expressed from a recombinant vector ex vivo. In an aspect, a guide nucleic acid provided herein can be expressed from a nucleic acid molecule in vivo. In an aspect, a guide nucleic acid provided herein can be expressed from a nucleic acid molecule in vitro. In an aspect, a guide nucleic acid provided herein can be expressed from a nucleic acid molecule ex vivo. In another aspect, a guide nucleic acid provided herein can be synthetically synthesized.

Linkers are short amino acid sequences used to join two or more proteins or protein domains into one larger protein complex. Linkers do not interfere with the native function of any protein, or protein domain, to which they are attached.

In an aspect, a linker is positioned between an amino acid sequence encoding a first nuclease and an amino acid sequence encoding a second nuclease. In an aspect, a first nuclease is selected from the group consisting of a Cas12a nuclease, a CasX nuclease, a Cas9 nuclease, a meganuclease, a zinc-finger nuclease, a transcription activator-like nuclease, and a HUH endonuclease. In an aspect, a second nuclease is selected from the group consisting of a Cas nuclease, a CasX nuclease, a Cas9 nuclease, a meganuclease, a zinc-finger nuclease, a transcription activator-like nuclease, and a HUH endonuclease.

In an aspect, a linker is positioned between an amino acid sequence encoding a nuclease and an amino acid sequence encoding a functional domain. In an aspect, the nuclease is selected from the group consisting of a meganuclease, a zinc-finger nuclease (ZFN), a transcription activator-like effector nucleases (TALEN), an Argonaute (non-limiting examples of Argonaute proteins include Thermus thermophilus Argonaute (TtAgo), Pyrococcus furiosus Argonaute (PfAgo), Natronobacterium gregoryi Argonaute (NgAgo), an RNA-guided nuclease, such as a CRISPR associated nuclease (non-limiting examples of CRISPR associated nucleases include Cas1, Cas1B, Cas2, Cas3, Cas4, Cas5, Cas6, Cas7, Cas8, Cas9 (also known as Csn1 and Csx12), Cas10, Cas12a (also known as Cpf1), Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, CasX, CasY, homologs thereof, or modified versions thereof). In an aspect, the functional domain is selected from the group consisting of a deaminase, a uracil DNA glycosylase (UGI), a transcriptional activator, a recombinase, a transposase, a helicase and a methylase. In some embodiments, the deaminase is a cytidine deaminase. In some embodiments, the deaminase is an adenine deaminase. In some embodiments, the deaminase is an APOPEC deaminase. In some embodiments, the deaminase is an activation-induced cytidine deaminase (AID). Non-limiting examples of recombinases include a tyrosine recombinase attached to a linker provided herein is selected from the group consisting of a Cre recombinase, a Gin recombinase, a Flp recombinase, and a Tnpl recombinase. In another aspect, a serine recombinase attached to a linker provided herein is selected from the group consisting of a PhiC31 integrase, an R4 integrase, and a TP-901 integrase. In another aspect, a DNA transposase attached to a linker provided herein is selected from the group consisting of a TALE-piggyBac and TALE-Mutator.

In an aspect, a linker is positioned between a first amino acid sequence encoding a Cas12a nuclease and a second amino acid sequence encoding a HUH endonuclease. In another aspect, a linker is positioned between a first amino acid sequence encoding a CasX nuclease and a second amino acid sequence encoding a HUH endonuclease.

In an aspect, a linker is positioned on the 5' end of a Cas12a nuclease. In another aspect, a linker is positioned on the 3' end of a Cas12a nuclease. In another aspect, a linker is positioned on the 5' end of a CasX nuclease. In another aspect, a linker is positioned on the 3' end of a CasX nuclease. In another aspect, a linker is positioned on the 5' end of a HUH endonuclease. In another aspect, a linker is positioned on the 3' end of a HUH endonuclease.

In an aspect, a linker comprises at least 5 amino acids. In another aspect, a linker comprises at least 10 amino acids. In another aspect, a linker comprises at least 15 amino acids. In another aspect, a linker comprises at least 20 amino acids. In another aspect, a linker comprises at least 25 amino acids. In another aspect, a linker comprises at least 30 amino acids. In another aspect, a linker comprises at least 40 amino acids. In another aspect, a linker comprises at least 50 amino acids.

In an aspect, a linker comprises between 5 amino acids and 50 amino acids. In another aspect, a linker comprises between 5 amino acids and 40 amino acids. In another aspect, a linker comprises between 5 amino acids and 30 amino acids. In another aspect, a linker comprises between 5 amino acids and 20 amino acids. In another, a linker comprises between 10 amino acids and 50 amino acids. In another aspect, a linker comprises between 10 amino acids and 40 amino acids. In another aspect, a linker comprises between 10 amino acids and 30 amino acids. In another aspect, a linker comprises between 10 amino acids and 20 amino acids.

In an aspect, a linker comprises 1 amino acid. In another aspect, a linker comprises 2 amino acids. In another aspect, a linker comprises 3 amino acids. In another aspect, a linker comprises 4 amino acids. In an aspect, a linker comprises 5 amino acids. In another aspect, a linker comprises 6 amino acids. In another aspect, a linker comprises 7 amino acids. In another aspect, a linker comprises 8 amino acids. In another aspect, a linker comprises 9 amino acids. In another aspect, a linker comprises 10 amino acids. In another aspect, a linker comprises 11 amino acids. In another aspect, a linker comprises 12 amino acids. In another aspect, a linker comprises 13 amino acids. In another aspect, a linker comprises 14 amino acids. In another aspect, a linker comprises 15 amino acids. In another aspect, a linker comprises 16 amino acids. In another aspect, a linker comprises 17 amino acids. In another aspect, a linker comprises 18 amino acids. In another aspect, a linker comprises 19 amino acids. In another aspect, a linker comprises 20 amino acids. In another aspect, a linker comprises 21 amino acids. In another aspect, a linker comprises 22 amino acids. In another aspect, a linker comprises 23 amino acids. In another aspect, a linker comprises 24 amino acids. In another aspect, a linker comprises 25 amino acids. In another aspect, a linker comprises 26 amino acids. In another aspect, a linker comprises 27 amino acids. In another aspect, a linker comprises 28 amino acids. In another aspect, a linker comprises 29 amino acids. In another aspect, a linker comprises 30 amino acids.

In an aspect, this disclosure provides an isolated polypeptide comprising an amino acid sequence at least 70% identical or similar to SEQ ID NO: 3. In an aspect, this disclosure provides an isolated polypeptide comprising an amino acid sequence at least 75% identical or similar to SEQ ID NO: 3. In an aspect, this disclosure provides an isolated polypeptide comprising an amino acid sequence at least 80% identical or similar to SEQ ID NO: 3. In an aspect, this disclosure provides an isolated polypeptide comprising an amino acid sequence at least 85% identical or similar to SEQ ID NO: 3. In an aspect, this disclosure provides an isolated polypeptide comprising an amino acid sequence at least 90% identical or similar to SEQ ID NO: 3. In an aspect, this disclosure provides an isolated polypeptide comprising an amino acid sequence at least 91% identical or similar to SEQ ID NO: 3. In an aspect, this disclosure provides an isolated polypeptide comprising an amino acid sequence at least 92% identical or similar to SEQ ID NO: 3. In an aspect, this disclosure provides an isolated polypeptide comprising an amino acid sequence at least 93% identical or similar to SEQ ID NO: 3. In an aspect, this disclosure provides an isolated polypeptide comprising an amino acid sequence at least 94% identical or similar to SEQ ID NO: 3. In an aspect, this disclosure provides an isolated polypeptide comprising an amino acid sequence at least 95% identical or similar to SEQ ID NO: 3. In an aspect, this disclosure provides an isolated polypeptide comprising an amino acid sequence at least 96% identical or similar to SEQ ID NO: 3. In an aspect, this disclosure provides an isolated polypeptide comprising an amino acid sequence at least 97% identical or similar to SEQ ID NO: 3. In an aspect, this disclosure provides an isolated polypeptide comprising an amino acid sequence at least 98% identical or similar to SEQ ID NO: 3. In an aspect, this disclosure provides an isolated polypeptide comprising an amino acid sequence at least 99% identical or similar to SEQ ID NO: 3. In an aspect, this disclosure provides an isolated polypeptide comprising an amino acid sequence 100% identical or similar to SEQ ID NO: 3.

In an aspect, a linker comprises an amino acid sequence at least 70% identical or similar to SEQ ID NO: 3. In another aspect, a linker comprises an amino acid sequence at least 75% identical or similar to SEQ ID NO: 3. In an aspect, a linker comprises an amino acid sequence at least 80% identical or similar to SEQ ID NO: 3. In another aspect, a linker comprises an amino acid sequence at least 85% identical or similar to SEQ ID NO: 3. In another aspect, a linker comprises an amino acid sequence at least 90% identical or similar to SEQ ID NO: 3. In another aspect, a linker comprises an amino acid sequence at least 91% identical or similar to SEQ ID NO: 3. In another aspect, a linker comprises an amino acid sequence at least 92% identical or similar to SEQ ID NO: 3. In another aspect, a linker comprises an amino acid sequence at least 93% identical or similar to SEQ ID NO: 3. In another aspect, a linker comprises an amino acid sequence at least 94% identical or similar to SEQ ID NO: 3. In another aspect, a linker comprises an amino acid sequence at least 95% identical or similar to SEQ ID NO: 3. In another aspect, a linker comprises an amino acid sequence at least 96% identical or similar to SEQ ID NO: 3. In another aspect, a linker comprises an amino acid sequence at least 97% identical or similar to SEQ ID NO: 3. In another aspect, a linker comprises an amino acid sequence at least 98% identical or similar to SEQ ID NO: 3. In another aspect, a linker comprises an amino acid sequence at least 99% identical or similar to SEQ ID NO: 3. In another aspect, a linker comprises an amino acid sequence 100% identical or similar to SEQ ID NO: 3.

In an aspect, a linker provided herein comprises SEQ ID NO: 3.

In an aspect, a polynucleotide encoding a linker comprises a polynucleotide sequence at least 70% identical to SEQ ID NO: 6. In another aspect, a polynucleotide encoding a linker comprises a polynucleotide sequence at least 75% identical to SEQ ID NO: 6. In another aspect, a polynucleotide encoding a linker comprises a polynucleotide sequence at least 80% identical to SEQ ID NO: 6. In another aspect, a polynucleotide encoding a linker comprises a polynucleotide sequence at least 85% identical to SEQ ID NO: 6. In another aspect, a polynucleotide encoding a linker comprises a polynucleotide sequence at least 90% identical to SEQ ID NO: 6. In another aspect, a polynucleotide encoding a linker comprises a polynucleotide sequence at least 91% identical to SEQ ID NO: 6. In another aspect, a polynucleotide encoding a linker comprises a polynucleotide sequence at least 92% identical to SEQ ID NO: 6. In another aspect, a polynucleotide encoding a linker comprises a polynucleotide sequence at least 93% identical to SEQ ID NO: 6. In another aspect, a polynucleotide encoding a linker comprises a polynucleotide sequence at least 94% identical to SEQ ID NO: 6. In another aspect, a polynucleotide encoding a linker comprises a polynucleotide sequence at least 95% identical to SEQ ID NO: 6. In another aspect, a polynucleotide encoding a linker comprises a polynucleotide sequence at least 96% identical to SEQ ID NO: 6. In another aspect, a polynucleotide encoding a linker comprises a polynucleotide sequence at least 97% identical to SEQ ID NO: 6. In another aspect, a polynucleotide encoding a linker comprises a polynucleotide sequence at least 98% identical to SEQ ID NO: 6. In another aspect, a polynucleotide encoding a linker comprises a polynucleotide sequence at least 99% identical to SEQ ID NO: 6. In another aspect, a polynucleotide encoding a linker comprises a polynucleotide sequence 100% identical to SEQ ID NO: 6.

Amino acids comprise a carboxylic acid (COOH) group and an amino group ($NH_2$) bound to a carbon atom, and each amino acid further comprises a variable R group. Based on the properties of the R group, amino acids can be characterized into groups of hydrophobic (non-polar) and hydrophilic (polar) amino acids.

Hydrophobic amino acids include glycine, alanine, valine, leucine, isoleucine, methionine, proline, phenylalanine, and tryptophan. Hydrophilic amino acids include tyrosine, serine, threonine, cysteine, glutamine, asparagine, glutamic acid, aspartic acid, lysine, histidine, and arginine.

In an aspect, the amino acid sequence of a linker comprises at least 5% hydrophobic amino acid residues. In another aspect, the amino acid sequence of a linker comprises at least 10% hydrophobic amino acid residues. In another aspect, the amino acid sequence of a linker comprises at least 15% hydrophobic amino acid residues. In another aspect, the amino acid sequence of a linker comprises at least 20% hydrophobic amino acid residues. In another aspect, the amino acid sequence of a linker comprises at least 25% hydrophobic amino acid residues. In another aspect, the amino acid sequence of a linker comprises at least 30% hydrophobic amino acid residues. In another aspect, the amino acid sequence of a linker comprises at least 35% hydrophobic amino acid residues. In another aspect, the amino acid sequence of a linker comprises at least 40% hydrophobic amino acid residues. In another aspect, the amino acid sequence of a linker comprises at least 45% hydrophobic amino acid residues. In another aspect, the amino acid sequence of a linker comprises at least 50% hydrophobic amino acid residues. In another aspect, the amino acid sequence of a linker comprises at least 55% hydrophobic amino acid residues. In another aspect, the amino acid sequence of a linker comprises at least 60% hydrophobic amino acid residues. In another aspect, the amino acid sequence of a linker comprises at least 65% hydrophobic amino acid residues. In another aspect, the amino acid sequence of a linker comprises at least 70% hydrophobic amino acid residues. In another aspect, the amino acid sequence of a linker comprises at least 75% hydrophobic amino acid residues. In another aspect, the amino acid sequence of a linker comprises at least 80% hydrophobic amino acid residues. In another aspect, the amino acid sequence of a linker comprises at least 85% hydrophobic amino acid residues. In another aspect, the amino acid sequence of a linker comprises at least 90% hydrophobic amino acid residues. In another aspect, the amino acid sequence of a linker comprises at least 95% hydrophobic amino acid residues.

In an aspect, the amino acid sequence of a linker comprises between 5% and 90% hydrophobic amino acid residues. In another aspect, the amino acid sequence of a linker comprises between 5% and 75% hydrophobic amino acid residues. In another aspect, the amino acid sequence of a linker comprises between 5% and 50% hydrophobic amino acid residues. In another aspect, the amino acid sequence of a linker comprises between 5% and 25% hydrophobic amino acid residues. In another aspect, the amino acid sequence of a linker comprises between 25% and 75% hydrophobic amino acid residues. In another aspect, the amino acid sequence of a linker comprises between 50% and 75% hydrophobic amino acid residues. In another aspect, the amino acid sequence of a linker comprises between 10% and 75% hydrophobic amino acid residues. In another aspect, the amino acid sequence of a linker comprises between 10% and 90% hydrophobic amino acid residues.

In an aspect, at least 10% of the amino acid sequence of a linker is comprised of any combination of glycine, threonine, and serine. In another aspect, at least 15% of the amino acid sequence of a linker is comprised of any combination of glycine, threonine, and serine. In another aspect, at least 20% of the amino acid sequence of a linker is comprised of any combination of glycine, threonine, and serine. In another aspect, at least 25% of the amino acid sequence of a linker is comprised of any combination of glycine, threonine, and serine. In another aspect, at least 30% of the amino acid sequence of a linker is comprised of any combination of glycine, threonine, and serine. In another aspect, at least 35% of the amino acid sequence of a linker is comprised of any combination of glycine, threonine, and serine. In another aspect, at least 40% of the amino acid sequence of a linker is comprised of any combination of glycine, threonine, and serine. In another aspect, at least 45% of the amino acid sequence of a linker is comprised of any combination of glycine, threonine, and serine. In another aspect, at least 50% of the amino acid sequence of a linker is comprised of any combination of glycine, threonine, and serine. In another aspect, at least 55% of the amino acid sequence of a linker is comprised of any combination of glycine, threonine, and serine. In another aspect, at least 60% of the amino acid sequence of a linker is comprised of any combination of glycine, threonine, and serine. In another aspect, at least 65% of the amino acid sequence of a linker is comprised of any combination of glycine, threonine, and serine. In another aspect, at least 70% of the amino acid sequence of a linker is comprised of any combination of glycine, threonine, and serine. In another aspect, at least 75% of the amino acid sequence of a linker is comprised of any combination of glycine, threonine, and serine. In another aspect, at least 80% of the amino acid sequence of a linker is comprised of any combination of glycine, threonine, and serine. In another aspect, at least 85% of the amino acid sequence of a linker is comprised of any combination of glycine, threonine, and serine. In another aspect, at least 90% of the amino acid sequence of a linker is comprised of any combination of glycine, threonine, and serine. In another aspect, at least 95% of the amino acid sequence of a linker is comprised of any combination of glycine, threonine, and serine.

In an aspect, between 10% and 95% of the amino acid sequence of a linker is comprised of any combination of glycine, threonine and serine. In another aspect, between 10% and 75% of the amino acid sequence of a linker is comprised of any combination of glycine, threonine and serine. In another aspect, between 10% and 50% of the amino acid sequence of a linker is comprised of any combination of glycine, threonine and serine. In another aspect, between 10% and 25% of the amino acid sequence of a linker is comprised of any combination of glycine, threonine and serine. In another aspect, between 25% and 75% of the amino acid sequence of a linker is comprised of any combination of glycine, threonine and serine. In another aspect, between 50% and 75% of the amino acid sequence of a linker is comprised of any combination of glycine, threonine and serine.

At physiological pH (e.g., 7.4), some amino acids have electrically charged R groups. For example, arginine, histidine, and lysine are positively charged amino acids; serine, threonine, asparagine, and glutamine are uncharged amino acids; and aspartic acid and glutamic acid are negatively charged amino acids.

In an aspect, the amino acid sequence of a linker comprises at least 5% negatively charged amino acid residues. In another aspect, the amino acid sequence of a linker comprises at least 10% negatively charged amino acid residues. In another aspect, the amino acid sequence of a linker comprises at least 15% negatively charged amino acid residues. In another aspect, the amino acid sequence of a linker comprises at least 20% negatively charged amino acid residues. In another aspect, the amino acid sequence of a linker comprises at least 25% negatively charged amino acid residues. In another aspect, the amino acid sequence of a linker comprises at least 30% negatively charged amino acid residues. In another aspect, the amino acid sequence of a linker comprises at least 35% negatively charged amino acid residues. In another aspect, the amino acid sequence of a linker comprises at least 40% negatively charged amino acid residues. In another aspect, the amino acid sequence of a linker comprises at least 45% negatively charged amino acid residues. In another aspect, the amino acid sequence of a linker comprises at least 50% negatively charged amino acid residues. In another aspect, the amino acid sequence of a linker comprises at least 55% negatively charged amino acid residues. In another aspect, the amino acid sequence of a linker comprises at least 60% negatively charged amino acid residues. In another aspect, the amino acid sequence of a linker comprises at least 65% negatively charged amino acid residues. In another aspect, the amino acid sequence of a linker comprises at least 70% negatively charged amino acid residues. In another aspect, the amino acid sequence of a linker comprises at least 75% negatively charged amino acid residues. In another aspect, the amino acid sequence of a linker comprises at least 80% negatively charged amino acid residues. In another aspect, the amino acid sequence of a linker comprises at least 85% negatively charged amino acid residues. In another aspect, the amino acid sequence of a linker comprises at least 90% negatively charged amino acid residues. In another aspect, the amino acid sequence of a linker comprises at least 95% negatively charged amino acid residues.

In an aspect, the amino acid sequence of a linker comprises between 5% and 90% negatively charged amino acid residues. In another aspect, the amino acid sequence of a linker comprises between 5% and 75% negatively charged amino acid residues. In another aspect, the amino acid sequence of a linker comprises between 5% and 50% negatively charged amino acid residues. In another aspect, the amino acid sequence of a linker comprises between 5% and 25% negatively charged amino acid residues. In another aspect, the amino acid sequence of a linker comprises between 25% and 75% negatively charged amino acid residues. In another aspect, the amino acid sequence of a linker comprises between 50% and 75% negatively charged amino acid residues. In another aspect, the amino acid sequence of a linker comprises between 10% and 75% negatively charged amino acid residues. In another aspect, the amino acid sequence of a linker comprises between 10% and 90% negatively charged amino acid residues.

In an aspect, a linker provided herein can be expressed from a recombinant vector in vivo. In an aspect, a linker provided herein can be expressed from a recombinant vector in vitro. In an aspect, a linker provided herein can be expressed from a recombinant vector ex vivo. In an aspect, a linker provided herein can be expressed from a nucleic acid molecule in vivo. In an aspect, a linker provided herein can be expressed from a nucleic acid molecule in vitro. In an aspect, a linker provided herein can be expressed from a nucleic acid molecule ex vivo.

HUH endonucleases contain a characteristic motif comprising a first histidine residue (H), a hydrophobic amino acid residue (U), and a second histidine residue (H). HUH endonucleases are known from archaeans, bacteria, and eukaryotes. Endogenous HUH endonucleases participate in cellular processes involving a transition from double-stranded to single-stranded DNA, such as rolling-circle replication in viruses and bacterial plasmid conjugation. The HUH endonuclease first nicks single-stranded DNA at a specific sequence at the origin of replication (ori) followed by formation of a covalent phosphotyrosine intermediate, whereby the 5' end of the DNA strand becomes linked to a specific tyrosine in the HUH-protein. While the phosphotyrosine linkage is an intermediate in vivo, purified HUH-proteins are able to form stable covalent bonds in vitro with synthetic oligonucleotides bearing their ori sequence.

In an aspect, a HUH endonuclease hybridizes to an origin of replication (ori) sequence.

In an aspect, a HUH endonuclease is porcine circovirus2 (PCV) HUH endonuclease. In another aspect, a HUH endonuclease is a duck circovirus (DCV) HUH endonuclease. In another aspect, a HUH endonuclease is a faba bean necrosis yellow virus (FBNYV) HUH endonuclease. In another aspect, a HUH endonuclease is a *Streptococcus agalactiae* replication protein RepB (RepB). In another aspect, a HUH endonuclease is a *Fructobacillus tropaeoli* RepB (RepBm). In another aspect, a HUH endonuclease is an *Escherichia coli* conjugation protein TraI (TraI). In another aspect, a HUH endonuclease is an *E. coli* mobilization protein A (mMobA). In another aspect, a HUH endonuclease is a *Staphylococcus aureus* nicking enzyme (NES).

In an aspect, a HUH endonuclease is selected from the group consisting of a FBNYV HUH endonuclease, a PCV HUH endonuclease, a DCV HUH endonuclease, a RepB, a RepBm, a TraI, a mMobA, and a NES.

In an aspect, a FBNYV HUH endonuclease comprises an amino acid sequence at least 80% identical or similar to the amino acid sequence of SEQ ID NO: 2. In another aspect, a FBNYV HUH endonuclease comprises an amino acid sequence at least 85% identical or similar to the amino acid sequence of SEQ ID NO: 2. In another aspect, a FBNYV HUH endonuclease comprises an amino acid sequence at least 90% identical or similar to the amino acid sequence of SEQ ID NO: 2. In another aspect, a FBNYV HUH endonuclease comprises an amino acid sequence at least 95% identical or similar to the amino acid sequence of SEQ ID NO: 2. In another aspect, a FBNYV HUH endonuclease comprises an amino acid sequence at least 96% identical or similar to the amino acid sequence of SEQ ID NO: 2. In another aspect, a FBNYV HUH endonuclease comprises an amino acid sequence at least 97% identical or similar to the amino acid sequence of SEQ ID NO: 2. In another aspect, a FBNYV HUH endonuclease comprises an amino acid sequence at least 98% identical or similar to the amino acid sequence of SEQ ID NO: 2. In another aspect, a FBNYV HUH endonuclease comprises an amino acid sequence at least 99% identical or similar to the amino acid sequence of SEQ ID NO: 2. In another aspect, a FBNYV HUH endonuclease comprises an amino acid sequence 100% identical or similar to the amino acid sequence of SEQ ID NO: 2.

In an aspect, a PCV HUH endonuclease comprises an amino acid sequence at least 80% identical or similar to the amino acid sequence of SEQ ID NO: 14. In another aspect, a PCV HUH endonuclease comprises an amino acid sequence at least 85% identical or similar to the amino acid sequence of SEQ ID NO: 14. In another aspect, a PCV HUH endonuclease comprises an amino acid sequence at least 90% identical or similar to the amino acid sequence of SEQ ID NO: 14. In another aspect, a PCV HUH endonuclease comprises an amino acid sequence at least 95% identical or similar to the amino acid sequence of SEQ ID NO: 14. In another aspect, a PCV HUH endonuclease comprises an amino acid sequence at least 96% identical or similar to the amino acid sequence of SEQ ID NO: 14. In another aspect, a PCV HUH endonuclease comprises an amino acid sequence at least 97% identical or similar to the amino acid sequence of SEQ ID NO: 14. In another aspect, a PCV HUH endonuclease comprises an amino acid sequence at least 98% identical or similar to the amino acid sequence of SEQ ID NO: 14. In another aspect, a PCV HUH endonuclease comprises an amino acid sequence at least 99% identical or similar to the amino acid sequence of SEQ ID NO: 14. In another aspect, a PCV HUH endonuclease comprises an amino acid sequence 100% identical or similar to the amino acid sequence of SEQ ID NO: 14.

In an aspect, a HUH endonuclease comprises an amino acid sequence at least 80% identical or similar to an amino acid sequence selected from the group consisting of SEQ ID NOs: 2 and 14. In an aspect, a HUH endonuclease comprises an amino acid sequence at least 85% identical or similar to an amino acid sequence selected from the group consisting of SEQ ID NOs: 2 and 14. In an aspect, a HUH endonuclease comprises an amino acid sequence at least 90% identical or similar to an amino acid sequence selected from the group consisting of SEQ ID NOs: 2 and 14. In an aspect, a HUH endonuclease comprises an amino acid sequence at least 95% identical or similar to an amino acid sequence selected from the group consisting of SEQ ID NOs: 2 and 14. In an aspect, a HUH endonuclease comprises an amino acid sequence at least 96% identical or similar to an amino acid sequence selected from the group consisting of SEQ ID NOs: 2 and 14. In an aspect, a HUH endonuclease comprises an amino acid sequence at least 97% identical or similar to an amino acid sequence selected from the group consisting of SEQ ID NOs: 2 and 14. In an aspect, a HUH endonuclease comprises an amino acid sequence at least 98% identical or similar to an amino acid sequence selected from the group consisting of SEQ ID NOs: 2 and 14. In an aspect, a HUH endonuclease comprises an amino acid sequence at least 99% identical or similar to an amino acid sequence selected from the group consisting of SEQ ID NOs: 2 and 14. In an aspect, a HUH endonuclease comprises an amino acid sequence 100% identical or similar to an amino acid sequence selected from the group consisting of SEQ ID NOs: 2 and 14.

In an aspect, a FBNYV HUH endonuclease is encoded by a nucleic acid sequence at least 80% identical to the nucleic acid sequence of SEQ ID NO: 5. In another aspect, a FBNYV HUH endonuclease is encoded by a nucleic acid sequence at least 85% identical to the nucleic acid sequence of SEQ ID NO: 5. In another aspect, a FBNYV HUH endonuclease is encoded by a nucleic acid sequence at least 90% identical to the nucleic acid sequence of SEQ ID NO: 5. In another aspect, a FBNYV HUH endonuclease is encoded by a nucleic acid sequence at least 95% identical to the nucleic acid sequence of SEQ ID NO: 5. In another aspect, a FBNYV HUH endonuclease is encoded by a nucleic acid sequence at least 96% identical to the nucleic acid sequence of SEQ ID NO: 5. In another aspect, a FBNYV HUH endonuclease is encoded by a nucleic acid sequence at least 97% identical to the nucleic acid sequence of SEQ ID NO: 5. In another aspect, a FBNYV HUH endonuclease is encoded by a nucleic acid sequence at least 98% identical to the nucleic acid sequence of SEQ ID NO: 5. In another aspect, a FBNYV HUH endonuclease is encoded by a nucleic acid sequence at least 99% identical to the nucleic acid sequence of SEQ ID NO: 5. In another aspect, a FBNYV HUH endonuclease is encoded by a nucleic acid sequence 100% identical to the nucleic acid sequence of SEQ ID NO: 5.

In an aspect, a PCV HUH endonuclease is encoded by a nucleic acid sequence at least 80% identical to the nucleic acid sequence of SEQ ID NO: 13. In another aspect, a PCV HUH endonuclease is encoded by a nucleic acid sequence at least 85% identical to the nucleic acid sequence of SEQ ID NO: 13. In another aspect, a PCV HUH endonuclease is encoded by a nucleic acid sequence at least 90% identical to the nucleic acid sequence of SEQ ID NO: 13. In another aspect, a PCV HUH endonuclease is encoded by a nucleic acid sequence at least 95% identical to the nucleic acid sequence of SEQ ID NO: 13. In another aspect, a PCV HUH endonuclease is encoded by a nucleic acid sequence at least 96% identical to the nucleic acid sequence of SEQ ID NO: 13. In another aspect, a PCV HUH endonuclease is encoded by a nucleic acid sequence at least 97% identical to the nucleic acid sequence of SEQ ID NO: 13. In another aspect, a PCV HUH endonuclease is encoded by a nucleic acid sequence at least 98% identical to the nucleic acid sequence of SEQ ID NO: 13. In another aspect, a PCV HUH endonuclease is encoded by a nucleic acid sequence at least 99% identical to the nucleic acid sequence of SEQ ID NO: 13. In another aspect, a PCV HUH endonuclease is encoded by a nucleic acid sequence 100% identical to the nucleic acid sequence of SEQ ID NO: 13.

In an aspect, a HUH endonuclease is encoded by a nucleic acid sequence at least 80% identical to a nucleic acid sequence selected from the group consisting of SEQ ID NOs: 5 and 13. In an aspect, a HUH endonuclease is encoded by a nucleic acid sequence at least 85% identical to a nucleic acid sequence selected from the group consisting of SEQ ID NOs: 5 and 13. In an aspect, a HUH endonuclease is encoded by a nucleic acid sequence at least 90% identical to a nucleic acid sequence selected from the group consisting of SEQ ID NOs: 5 and 13. In an aspect, a HUH endonuclease is encoded by a nucleic acid sequence at least 95% identical to a nucleic acid sequence selected from the group consisting of SEQ ID NOs: 5 and 13. In an aspect, a HUH endonuclease is encoded by a nucleic acid sequence at least 96% identical to a nucleic acid sequence selected from the group consisting of SEQ ID NOs: 5 and 13. In an aspect, a HUH endonuclease is encoded by a nucleic acid sequence at least 97% identical to a nucleic acid sequence selected from the group consisting of SEQ ID NOs: 5 and 13. In an aspect, a HUH endonuclease is encoded by a nucleic acid sequence at least 98% identical to a nucleic acid sequence selected from the group consisting of SEQ ID NOs: 5 and 13. In an aspect, a HUH endonuclease is encoded by a nucleic acid sequence at least 99% identical to a nucleic acid sequence selected from the group consisting of SEQ ID NOs: 5 and 13. In an aspect, a HUH endonuclease is encoded by a nucleic acid sequence 100% identical to a nucleic acid sequence selected from the group consisting of SEQ ID NOs: 5 and 13.

In an aspect, a HUH endonuclease provided herein can be expressed from a recombinant vector in vivo. In an aspect, a HUH endonuclease provided herein can be expressed from a recombinant vector in vitro. In an aspect, a HUH endonuclease provided herein can be expressed from a recombinant vector ex vivo. In an aspect, a HUH endonuclease provided herein can be expressed from a nucleic acid molecule in vivo. In an aspect, a HUH endonuclease provided herein can be expressed from a nucleic acid molecule in vitro. In an aspect, a HUH endonuclease provided herein can be expressed from a nucleic acid molecule ex vivo.

In an aspect, a ribonucleoprotein comprises an amino acid sequence at least 80% identical or similar to an amino acid selected from the group consisting of SEQ ID NOs: 20-23 and 25. In an aspect, a ribonucleoprotein comprises an amino acid sequence at least 85% identical or similar to an amino acid selected from the group consisting of SEQ ID NOs: 20-23 and 25. In an aspect, a ribonucleoprotein comprises an amino acid sequence at least 90% identical or similar to an amino acid selected from the group consisting of SEQ ID NOs: 20-23 and 25. In an aspect, a ribonucleoprotein comprises an amino acid sequence at least 95% identical or similar to an amino acid selected from the group consisting of SEQ ID NOs: 20-23 and 25. In an aspect, a ribonucleoprotein comprises an amino acid sequence at least 96% identical or similar to an amino acid selected from the group consisting of SEQ ID NOs: 20-23 and 25. In an aspect, a ribonucleoprotein comprises an amino acid sequence at least 97% identical or similar to an amino acid selected from the group consisting of SEQ ID NOs: 20-23 and 25. In an aspect, a ribonucleoprotein comprises an amino acid sequence at least 98% identical or similar to an amino acid selected from the group consisting of SEQ ID NOs: 20-23 and 25. In an aspect, a ribonucleoprotein comprises an amino acid sequence at least 99% identical or similar to an amino acid selected from the group consisting of SEQ ID NOs: 20-23 and 25. In an aspect, a ribonucleoprotein comprises an amino acid sequence 100% identical or similar to an amino acid selected from the group consisting of SEQ ID NOs: 20-23 and 25.

In an aspect, a recombinant nucleic acid encodes an amino acid sequence at least 80% identical or similar to an amino acid selected from the group consisting of SEQ ID NOs: 20-23 and 25. In an aspect, a recombinant nucleic acid encodes an amino acid sequence at least 85% identical or similar to an amino acid selected from the group consisting of SEQ ID NOs: 20-23 and 25. In an aspect, a recombinant nucleic acid encodes an amino acid sequence at least 90% identical or similar to an amino acid selected from the group consisting of SEQ ID NOs: 20-23 and 25. In an aspect, a recombinant nucleic acid encodes an amino acid sequence at least 95% identical or similar to an amino acid selected from the group consisting of SEQ ID NOs: 20-23 and 25. In an aspect, a recombinant nucleic acid encodes an amino acid sequence at least 96% identical or similar to an amino acid selected from the group consisting of SEQ ID NOs: 20-23 and 25. In an aspect, a recombinant nucleic acid encodes an amino acid sequence at least 97% identical or similar to an amino acid selected from the group consisting of SEQ ID NOs: 20-23 and 25. In an aspect, a recombinant nucleic acid encodes an amino acid sequence at least 98% identical or similar to an amino acid selected from the group consisting of SEQ ID NOs: 20-23 and 25. In an aspect, a recombinant nucleic acid encodes an amino acid sequence at least 99% identical or similar to an amino acid selected from the group consisting of SEQ ID NOs: 20-23 and 25. In an aspect, a recombinant nucleic acid encodes an amino acid sequence 100% identical or similar to an amino acid selected from the group consisting of SEQ ID NOs: 20-23 and 25.

In aspect, a recombinant nucleic acid comprises a polynucleotide sequence at least 80% identical to a sequence selected from the group consisting of SEQ ID Nos: 7, 17-19, and 24. In aspect, a recombinant nucleic acid comprises a polynucleotide sequence at least 85% identical to a sequence selected from the group consisting of SEQ ID Nos: 7, 17-19, and 24. In aspect, a recombinant nucleic acid comprises a polynucleotide sequence at least 90% identical to a sequence selected from the group consisting of SEQ ID Nos: 7, 17-19, and 24. In aspect, a recombinant nucleic acid comprises a polynucleotide sequence at least 95% identical to a sequence selected from the group consisting of SEQ ID Nos: 7, 17-19, and 24. In aspect, a recombinant nucleic acid comprises a polynucleotide sequence at least 96% identical to a sequence selected from the group consisting of SEQ ID Nos: 7, 17-19, and 24. In aspect, a recombinant nucleic acid comprises a polynucleotide sequence at least 97% identical to a sequence selected from the group consisting of SEQ ID Nos: 7, 17-19, and 24. In aspect, a recombinant nucleic acid comprises a polynucleotide sequence at least 98% identical to a sequence selected from the group consisting of SEQ ID Nos: 7, 17-19, and 24. In aspect, a recombinant nucleic acid comprises a polynucleotide sequence at least 99% identical to a sequence selected from the group consisting of SEQ ID Nos: 7, 17-19, and 24. In aspect, a recombinant nucleic acid comprises a polynucleotide sequence at least 100% identical to a sequence selected from the group consisting of SEQ ID Nos: 7, 17-19, and 24.

As used herein, a "template nucleic acid molecule" refers to a nucleic acid molecule that comprises a nucleic acid sequence that is to be inserted into a target DNA molecule. In an aspect, a template nucleic acid molecule comprises single-stranded DNA. In another aspect, a template nucleic acid molecule comprises double-stranded DNA. In a further aspect, a template nucleic acid molecule comprises single-stranded RNA. In yet another aspect, a template nucleic acid molecule comprises double-stranded RNA. In another aspect, a template nucleic acid molecule comprises DNA and RNA.

In an aspect, a ribonucleoprotein comprises at least one template nucleic acid molecule. In another aspect, a ribonucleoprotein comprises at least two template nucleic acid molecules.

In an aspect, a template nucleic acid molecule comprises at least 10 nucleotides. In another aspect, a template nucleic acid molecule comprises at least 25 nucleotides. In another aspect, a template nucleic acid molecule comprises at least 50 nucleotides. In another aspect, a template nucleic acid molecule comprises at least 75 nucleotides. In another aspect, a template nucleic acid molecule comprises at least 100 nucleotides. In another aspect, a template nucleic acid molecule comprises at least 250 nucleotides. In another aspect, a template nucleic acid molecule comprises at least 500 nucleotides. In another aspect, a template nucleic acid molecule comprises at least 750 nucleotides. In another aspect, a template nucleic acid molecule comprises at least 1000 nucleotides. In another aspect, a template nucleic acid molecule comprises at least 2500 nucleotides.

In an aspect, a template nucleic acid molecule comprises between 10 nucleotides and 2500 nucleotides. In another aspect, a template nucleic acid molecule comprises between 25 nucleotides and 2500 nucleotides. In another aspect, a template nucleic acid molecule comprises between 50 nucleotides and 2500 nucleotides. In another aspect, a template nucleic acid molecule comprises between 75 nucleotides and 2500 nucleotides. In another aspect, a template nucleic acid molecule comprises between 100 nucleotides and 2500 nucleotides. In another aspect, a template nucleic acid molecule comprises between 250 nucleotides and 2500 nucleotides. In another aspect, a template nucleic acid molecule comprises between 500 nucleotides and 2500 nucleotides. In another aspect, a template nucleic acid molecule comprises between 25 nucleotides and 1000 nucleotides. In another aspect, a template nucleic acid molecule comprises between 25 nucleotides and 500 nucleotides. In another aspect, a template nucleic acid molecule comprises between 25 nucleotides and 250 nucleotides.

As noted above, a HUH endonuclease first nicks single-stranded DNA at a specific sequence at the origin of replication (ori) followed by formation of a covalent phosphotyrosine intermediate, whereby the 5' end of the DNA strand becomes linked to a specific tyrosine in the HUH-protein. While the phosphotyrosine linkage is an intermediate in vivo, purified HUH-proteins are able to form stable covalent bonds in vitro with synthetic oligonucleotides bearing their ori sequence.

In aspect, a template nucleic acid molecule comprises a nucleic acid sequence encoding an origin of replication (ori). In an aspect, an ori provided herein is capable of hybridizing to a HUH endonuclease. In an aspect, an ori comprises a nucleic acid sequence at least 80% identical to SEQ ID NO: 12. In another aspect, an ori comprises a nucleic acid sequence at least 85% identical to SEQ ID NO: 12. In another aspect, an ori comprises a nucleic acid sequence at least 90% identical to SEQ ID NO: 12. In another aspect, an ori comprises a nucleic acid sequence at least 95% identical to SEQ ID NO: 12. In another aspect, an ori comprises a nucleic acid sequence at least 96% identical to SEQ ID NO: 12. In another aspect, an ori comprises a nucleic acid sequence at least 97% identical to SEQ ID NO: 12. In another aspect, an ori comprises a nucleic acid sequence at least 98% identical to SEQ ID NO: 12. In another aspect, an ori comprises a nucleic acid sequence at least 99% identical to SEQ ID NO: 12. In another aspect, an ori comprises a nucleic acid sequence 100% identical to SEQ ID NO: 12. In an aspect, an ori comprises a nucleic acid sequence at least 80% identical to SEQ ID NO: 27. In another aspect, an ori comprises a nucleic acid sequence at least 85% identical to SEQ ID NO: 27. In another aspect, an ori comprises a nucleic acid sequence at least 90% identical to SEQ ID NO: 27. In another aspect, an ori comprises a nucleic acid sequence at least 95% identical to SEQ ID NO: 27. In another aspect, an ori comprises a nucleic acid sequence at least 96% identical to SEQ ID NO: 27. In another aspect, an ori comprises a nucleic acid sequence at least 97% identical to SEQ ID NO: 27. In another aspect, an ori comprises a nucleic acid sequence at least 98% identical to SEQ ID NO: 27. In another aspect, an ori comprises a nucleic acid sequence at least 99% identical to SEQ ID NO: 27. In another aspect, an ori comprises a nucleic acid sequence 100% identical to SEQ ID NO: 27. In an aspect, an ori comprises a nucleic acid sequence at least 80% identical to SEQ ID NO: 28. In another aspect, an ori comprises a nucleic acid sequence at least 85% identical to SEQ ID NO: 28. In another aspect, an ori comprises a nucleic acid sequence at least 90% identical to SEQ ID NO: 28. In another aspect, an ori comprises a nucleic acid sequence at least 95% identical to SEQ ID NO: 28. In another aspect, an ori comprises a nucleic acid sequence at least 96% identical to SEQ ID NO: 28. In another aspect, an ori comprises a nucleic acid sequence at least 97% identical to SEQ ID NO: 28. In another aspect, an ori comprises a nucleic acid sequence at least 98% identical to SEQ ID NO: 28. In another aspect, an ori comprises a nucleic acid sequence at least 99% identical to SEQ ID NO: 28. In another aspect, an ori comprises a nucleic acid sequence 100% identical to SEQ ID NO: 28.

In an aspect, an ori comprises at least 10 nucleotides. In an aspect, an ori comprises at least 15 nucleotides. In an aspect, an ori comprises at least 20 nucleotides. In an aspect, an ori comprises at least 25 nucleotides. In an aspect, an ori comprises at least 30 nucleotides. In an aspect, an ori comprises at least 40 nucleotides.

In an aspect, an ori is positioned on the 5'-end of a template nucleic acid molecule. In another aspect, an ori is positioned on the 3'-end of a template nucleic acid molecule.

In an aspect, a template nucleic acid molecule comprises a nucleic acid sequence encoding a gene of interest. As used herein, a "gene of interest" refers to a polynucleotide sequence encoding a protein or a non-protein-coding RNA molecule that is to be inserted into a target DNA molecule. In an aspect, a gene of interest encodes a protein. In another aspect, a gene of interest encodes a non-protein-coding RNA molecule.

Non-limiting examples of a non-protein-coding RNA molecule include a microRNA (miRNA), a miRNA precursor (pre-miRNA), a small interfering RNA (siRNA), a small RNA (18 to 26 nucleotides in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single guide RNA (sgRNA). In an aspect, a non-protein-coding RNA molecule comprises a miRNA. In an aspect, a non-protein-coding RNA molecule comprises a siRNA. In an aspect, a non-protein-coding RNA molecule comprises a ta-siRNA. In an aspect, a non-protein-coding RNA molecule is selected from the group consisting of a miRNA, a siRNA, and a ta-siRNA.

In an aspect, a gene of interest is exogenous to a target DNA molecule. In an aspect, a gene of interest replaces an endogenous gene in a target DNA molecule.

As used herein, a "target DNA molecule" refers to a selected DNA molecule or a selected sequence or region of a DNA molecule in which a modification (e.g., cleavage, site-directed integration) is desired.

As used herein, a "target region" refers to the portion of a target DNA molecule that is cleaved by a CRISPR nuclease. In contrast to a non-target nucleic acid (e.g., non-target ssDNA) or non-target region, a target site comprises significant complementarity to a guide nucleic acid or a guide RNA.

In an aspect, a target site is 100% complementary to a guide nucleic acid. In another aspect, a target site is 99% complementary to a guide nucleic acid. In another aspect, a target site is 98% complementary to a guide nucleic acid. In another aspect, a target site is 97% complementary to a guide nucleic acid. In another aspect, a target site is 96% complementary to a guide nucleic acid. In another aspect, a target site is 95% complementary to a guide nucleic acid. In another aspect, a target site is 94% complementary to a guide nucleic acid. In another aspect, a target site is 93% complementary to a guide nucleic acid. In another aspect, a target site is 92% complementary to a guide nucleic acid. In another aspect, a target site is 91% complementary to a guide nucleic acid. In another aspect, a target site is 90% complementary to a guide nucleic acid. In another aspect, a target site is 85% complementary to a guide nucleic acid. In another aspect, a target site is 80% complementary to a guide nucleic acid.

In an aspect, a target site comprises at least one PAM site. In an aspect, a target site is adjacent to a nucleic acid sequence that comprises at least one PAM site. In another aspect, a target site is within 5 nucleotides of at least one PAM site. In a further aspect, a target site is within 10 nucleotides of at least one PAM site. In another aspect, a target site is within 15 nucleotides of at least one PAM site. In another aspect, a target site is within 20 nucleotides of at least one PAM site. In another aspect, a target site is within 25 nucleotides of at least one PAM site. In another aspect, a target site is within 30 nucleotides of at least one PAM site.

In an aspect, a target DNA molecule is single-stranded. In another aspect, a target DNA molecule is double-stranded.

In an aspect, a target DNA molecule comprises genomic DNA. In an aspect, a target DNA molecule is positioned within a nuclear genome. In an aspect, a target DNA molecule comprises chromosomal DNA. In an aspect, a target DNA molecule comprises plasmid DNA. In an aspect, a target DNA molecule is positioned within a plasmid. In an aspect, a target DNA molecule comprises mitochondrial DNA. In an aspect, a target DNA molecule is positioned within a mitochondrial genome. In an aspect, a target DNA molecule comprises plastid DNA. In an aspect, a target DNA molecule is positioned within a plastid genome. In an aspect, a target DNA molecule comprises chloroplast DNA. In an aspect, a target DNA molecule is positioned within a chloroplast genome. In an aspect, a target DNA molecule is positioned within a genome selected from the group consisting of a nuclear genome, a mitochondrial genome, and a plastid genome.

In an aspect, a target DNA molecule comprises genic DNA. As used herein, "genic DNA" refers to DNA that encodes one or more genes. In another aspect, a target DNA molecule comprises intergenic DNA. In contrast to genic DNA, "intergenic DNA" comprises noncoding DNA, and lacks DNA encoding a gene. In an aspect, intergenic DNA is positioned between two genes.

In an aspect, a target nucleic acid encodes a gene. As used herein, a "gene" refers to a polynucleotide that can produce a functional unit (e.g., without being limiting, for example, a protein, or a non-coding RNA molecule). A gene can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof. A "gene sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a non-protein-coding RNA molecule or a precursor thereof. In another aspect, a gene encodes a protein. In some embodiments, the target DNA molecule is selected from the group consisting of: a promoter, an enhancer sequence, a leader sequence, a transcriptional start site, a transcriptional stop site, a polyadenylation site, an exon, intron, a splice site, a 5'-UTR, a 3'-UTR, a protein coding sequence, a non-protein-coding sequence, a miRNA, a pre-miRNA and a miRNA binding site.

In an aspect, this disclosure provides a method of generating an edit in a target DNA molecule comprising contacting the target DNA molecule with a ribonucleoprotein, where the ribonucleoprotein comprises (a) a recombinant polypeptide comprising: (i) an amino acid sequence encoding a Cas12a nuclease; (ii) an amino acid sequence encoding a linker; and (iii) an amino acid sequence encoding a HUH endonuclease; (b) at least one guide nucleic acid; and (c) at least one template nucleic acid molecule, where the ribonucleoprotein edits the target DNA molecule. In an aspect, this disclosure provides a method of generating an edit in a target DNA molecule comprising contacting the target DNA molecule with a ribonucleoprotein, where the ribonucleoprotein comprises (a) a recombinant polypeptide comprising: (i) an amino acid sequence encoding a CasX nuclease; (ii) an amino acid sequence encoding a linker; and (iii) an amino acid sequence encoding a HUH endonuclease; (b) at least one guide nucleic acid; and (c) at least one template nucleic acid molecule, where the ribonucleoprotein edits the target DNA molecule. In an aspect, a method provided herein further comprises: (d) detecting the at least one edit in the target DNA molecule.

In an aspect, this disclosure provides a method of generating an edit in a target DNA molecule comprising providing to a cell: (a) a recombinant polypeptide comprising: (i) an amino acid sequence encoding a Cas12a nuclease; (ii) an amino acid sequence encoding a linker; and (iii) an amino acid sequence encoding a HUH endonuclease, or one or more nucleic acid molecules encoding the recombinant polypeptide; (b) at least one guide nucleic acid, or at least one nucleic acid molecule encoding the at least one guide nucleic acid; and (c) at least one template nucleic acid molecule, or at least one nucleic acid molecule encoding the at least one template nucleic acid molecule, where the recombinant polypeptide, the at least one guide nucleic acid, and the at least one template nucleic acid form a ribonucleoprotein, and where the ribonucleoprotein generates at least one edit in the target DNA molecule within the cell. In an aspect, this disclosure provides a method of generating an edit in a target DNA molecule comprising providing to a cell: (a) a recombinant polypeptide comprising: (i) an amino acid sequence encoding a CasX nuclease; (ii) an amino acid sequence encoding a linker; and (iii) an amino acid sequence encoding a HUH endonuclease, or one or more nucleic acid molecules encoding the recombinant polypeptide; (b) at least one guide nucleic acid, or at least one nucleic acid molecule encoding the at least one guide nucleic acid; and (c) at least one template nucleic acid molecule, or at least one nucleic acid molecule encoding the at least one template nucleic acid molecule, where the recombinant polypeptide, the at least one guide nucleic acid, and the at least one template nucleic acid form a ribonucleoprotein, and where the ribonucleoprotein generates at least one edit in the target DNA molecule within the cell. In an aspect, a method provided herein further comprises: (d) detecting the at least one edit in the target DNA molecule. In an aspect, the ribonucleoprotein forms within the cell. In an aspect, the ribonucleoprotein forms outside the cell. In an aspect, the ribonucleoprotein forms in vivo. In an aspect, the ribonucleoprotein forms in vitro.

In an aspect, an edit provided herein comprises a mutation. As used herein, a "mutation" refers to a non-naturally occurring alteration to a nucleic acid or amino acid sequence as compared to a naturally occurring reference nucleic acid or amino acid sequence from the same organism. It will be appreciated that, when identifying a mutation, the reference sequence should be from the same nucleic acid (e.g, gene, non-coding RNA) or amino acid (e.g, protein). In determining if an difference between two sequences comprises a mutation, it will be appreciated in the art that the comparison should not be made between homologous sequences of two different species or between homologous sequences of two different varieties of a single species. Rather, the comparison should be made between the edited sequence and the endogenous, non-edited (e.g., "wildtype") sequence of the same organism.

In an aspect, a mutation comprises the insertion of at least one nucleotide or amino acid. In another aspect, a mutation comprises the deletion of at least one nucleotide or amino acid. In a further aspect, a mutation comprises the substitution of at least one nucleotide or amino acid. In still a further aspect, a mutation comprises the inversion of at least two nucleotides or amino acids. In another aspect, a mutation is selected from the group consisting of an insertion, a deletion, a substitution, and an inversion.

In an aspect, a mutation comprises a site-directed integration. In an aspect, a site-directed integration comprises the insertion of all or part of a template nucleic acid molecule into a target DNA molecule.

As used herein, "site-directed integration" refers to all, or a portion, of a desired sequence (e.g., template nucleic acid molecule) being inserted or integrated at a desired site or locus within the plant genome (e.g., target DNA molecule). The desired sequence can comprise a transgene or construct. In an aspect, a template nucleic acid molecule comprises one or two homology arms flanking the desired sequence to promote the targeted insertion event through homologous recombination and/or homology-directed repair.

Any site or locus within the genome of a plant, animal, fungi, or bacteria may potentially be chosen for site-directed integration of a transgene or construct of the present disclosure.

For site-directed integration, a double-strand break (DSB) or nick may first be made at a target DNA molecule via a RNA-guided CRISPR nuclease or ribonucleoprotein provided herein. In the presence of a template nucleic acid molecule, the DSB or nick can then be repaired by homologous recombination (HR) between the homology arm(s) of the template nucleic acid molecule and the target DNA molecule, or by non-homologous end joining (NHEJ), resulting in site-directed integration of all or part of the template nucleic acid molecule into the target DNA molecule to create the targeted insertion event at the site of the DSB or nick.

In an aspect, site-directed integration comprises the use of NHEJ repair mechanisms endogenous to a cell. In another aspect, site-directed integration comprises the use of HR repair mechanisms endogenous to a cell.

In an aspect, a mutation comprises the integration of at least 5 contiguous nucleotides of a template nucleic acid molecule into a target DNA molecule. In an aspect, a mutation comprises the integration of at least 10 contiguous nucleotides of a template nucleic acid molecule into a target DNA molecule. In an aspect, a mutation comprises the integration of at least 15 contiguous nucleotides of a template nucleic acid molecule into a target DNA molecule. In an aspect, a mutation comprises the integration of at least 20 contiguous nucleotides of a template nucleic acid molecule into a target DNA molecule. In an aspect, a mutation comprises the integration of at least 25 contiguous nucleotides of a template nucleic acid molecule into a target DNA molecule. In an aspect, a mutation comprises the integration of at least 50 contiguous nucleotides of a template nucleic acid molecule into a target DNA molecule. In an aspect, a mutation comprises the integration of at least 100 contiguous nucleotides of a template nucleic acid molecule into a target DNA molecule. In an aspect, a mutation comprises the integration of at least 250 contiguous nucleotides of a template nucleic acid molecule into a target DNA molecule. In an aspect, a mutation comprises the integration of at least 500 contiguous nucleotides of a template nucleic acid molecule into a target DNA molecule. In an aspect, a mutation comprises the integration of at least 1000 contiguous nucleotides of a template nucleic acid molecule into a target DNA molecule. In an aspect, a mutation comprises the integration of at least 2000 contiguous nucleotides of a template nucleic acid molecule into a target DNA molecule.

In an aspect, a mutation comprises the integration of between 5 contiguous nucleotides and 3500 contiguous nucleotides of a template nucleic acid molecule into a target DNA molecule. In an aspect, a mutation comprises the integration of between 5 contiguous nucleotides and 2500 contiguous nucleotides of a template nucleic acid molecule into a target DNA molecule. In an aspect, a mutation comprises the integration of between 5 contiguous nucleotides and 1500 contiguous nucleotides of a template nucleic acid molecule into a target DNA molecule. In an aspect, a mutation comprises the integration of between 5 contiguous nucleotides and 750 contiguous nucleotides of a template nucleic acid molecule into a target DNA molecule. In an aspect, a mutation comprises the integration of between 5 contiguous nucleotides and 500 contiguous nucleotides of a template nucleic acid molecule into a target DNA molecule. In an aspect, a mutation comprises the integration of between 5 contiguous nucleotides and 250 contiguous nucleotides of a template nucleic acid molecule into a target DNA molecule. In an aspect, a mutation comprises the integration of between 5 contiguous nucleotides and 150 contiguous nucleotides of a template nucleic acid molecule into a target DNA molecule. In an aspect, a mutation comprises the integration of between 25 contiguous nucleotides and 2500 contiguous nucleotides of a template nucleic acid molecule into a target DNA molecule. In an aspect, a mutation comprises the integration of between 25 contiguous nucleotides and 1500 contiguous nucleotides of a template nucleic acid molecule into a target DNA molecule. In an aspect, a mutation comprises the integration of between 25 contiguous nucleotides and 750 contiguous nucleotides of a template nucleic acid molecule into a target DNA molecule. In an aspect, a mutation comprises the integration of between 50 contiguous nucleotides and 2500 contiguous nucleotides of a template nucleic acid molecule into a target DNA molecule. In an aspect, a mutation comprises the integration of between 50 contiguous nucleotides and 1500 contiguous nucleotides of a template nucleic acid molecule into a target DNA molecule. In an aspect, a mutation comprises the integration of between 50 contiguous nucleotides and 750 contiguous nucleotides of a template nucleic acid molecule into a target DNA molecule. In an aspect, a mutation comprises the integration of between 100 contiguous nucleotides and 2500 contiguous nucleotides of a template nucleic acid molecule into a target DNA molecule. In an aspect, a mutation comprises the integration of between 100 contiguous nucleotides and 1500 contiguous nucleotides of a template nucleic acid molecule into a target DNA molecule. In an aspect, a mutation comprises the integration of between 100 contiguous nucleotides and 750 contiguous nucleotides of a template nucleic acid molecule into a target DNA molecule.

In an aspect, a method provided herein comprises detecting an edit or a mutation in a target DNA molecule. Any method available in the art capable of detecting an edit or a mutation in a target DNA molecule. Without being limiting, suitable methods for detecting an edit or a mutation include a Southern blot, polymerase chain reaction (PCR), and nucleic acid sequencing.

Any method provided herein can involve transient transfection or stable transformation of a cell of interest (e.g., a eukaryotic cell, a prokaryotic cell). In an aspect, a nucleic acid molecule provided herein is stably transformed into a cell. In an aspect, a nucleic acid molecule provided herein is transiently transfected into a cell.

In an aspect, a nucleic acid molecule encoding Cas12a nuclease is stably transformed into a cell. In another aspect, a nucleic acid molecule encoding a Cas12a nuclease is transiently transfected into a cell. In another aspect, a Cas12a nuclease is transfected into a cell.

In an aspect, a nucleic acid molecule encoding a CasX nuclease is stably transformed into a cell. In another aspect, a nucleic acid molecule encoding a CasX nuclease is transiently transfected into a cell. In another aspect, a CasX nuclease is transfected into a cell.

In an aspect, a nucleic acid molecule encoding a linker is stably transformed into a cell. In another aspect, a nucleic acid molecule encoding a linker is transiently transfected into a cell. In another aspect, a linker is transfected into a cell.

In an aspect, a nucleic acid molecule encoding a HUH endonuclease is stably transformed into a cell. In another aspect, a nucleic acid molecule encoding a HUH endonuclease is transiently transfected into a cell. In another aspect, a HUH endonuclease is transfected into a cell.

In an aspect, a nucleic acid molecule encoding a FBNYV HUH endonuclease is stably transformed into a cell. In another aspect, a nucleic acid molecule encoding a FBNYV HUH endonuclease is transiently transfected into a cell. In another aspect, a FBNYV HUH endonuclease is transfected into a cell.

In an aspect, a nucleic acid molecule encoding a PCV HUH endonuclease is stably transformed into a cell. In another aspect, a nucleic acid molecule encoding a PCV HUH endonuclease is transiently transfected into a cell. In another aspect, a PCV HUH endonuclease is transfected into a cell.

In an aspect, a nucleic acid molecule encoding a guide nucleic acid is stably transformed into a cell. In another aspect, a nucleic acid molecule encoding a guide nucleic acid is transiently transfected into a cell. In another aspect, a guide nucleic acid is transfected into a cell.

In an aspect, a nucleic acid molecule encoding a template nucleic acid molecule is stably transformed into a cell. In another aspect, a nucleic acid molecule encoding a template nucleic acid molecule is transiently transfected into a cell. In another aspect, a template nucleic acid molecule is transfected into a cell.

In an aspect, a nucleic acid molecule encoding one or more components of a ribonucleoprotein is stably transformed into a cell. In another aspect, a nucleic acid molecule encoding one or more components of a ribonucleoprotein is transiently transfected into a cell. In another aspect, a ribonucleoprotein is transfected into a cell.

Numerous methods for transforming cells with a recombinant nucleic acid molecule or construct are known in the art, which can be used according to methods of the present application. Any suitable method or technique for transformation of a cell known in the art can be used according to present methods. Effective methods for transformation of plants include bacterially mediated transformation, such as *Agrobacterium*-mediated or Rhizobium-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants.

In an aspect, a method comprises providing a cell with a nucleic acid molecule, a protein, or a ribonucleoprotein via *Agrobacterium*-mediated transformation. In an aspect, a method comprises providing a cell with a nucleic acid molecule, a protein, or a ribonucleoprotein via polyethylene glycol-mediated transformation. In an aspect, a method comprises providing a cell with a nucleic acid molecule, a protein, or a ribonucleoprotein via biolistic transformation. In an aspect, a method comprises providing a cell with a nucleic acid molecule, a protein, or a ribonucleoprotein via liposome-mediated transfection. In an aspect, a method comprises providing a cell with a nucleic acid molecule, a protein, or a ribonucleoprotein via viral transduction. In an aspect, a method comprises providing a cell with a nucleic acid molecule, a protein, or a ribonucleoprotein via use of one or more delivery particles. In an aspect, a method comprises providing a cell with a nucleic acid molecule, a protein, or a ribonucleoprotein via microinjection. In an aspect, a method comprises providing a cell with a nucleic acid molecule, a protein, or a ribonucleoprotein via electroporation.

In an aspect, a nucleic acid molecule is provided to a cell via a method selected from the group consisting of *Agrobacterium*-mediated transformation, polyethylene glycol-mediated transformation, biolistic transformation, liposome-mediated transfection, viral transduction, the use of one or more delivery particles, microinjection, and electroporation.

In an aspect, a protein is provided to a cell via a method selected from the group consisting of *Agrobacterium*-mediated transformation, polyethylene glycol-mediated transformation, biolistic transformation, liposome-mediated transfection, viral transduction, the use of one or more delivery particles, microinjection, and electroporation.

In an aspect, a ribonucleoprotein is provided to a cell via a method selected from the group consisting of *Agrobacterium*-mediated transformation, polyethylene glycol-mediated transformation, biolistic transformation, liposome-mediated transfection, viral transduction, the use of one or more delivery particles, microinjection, and electroporation.

Other methods for transformation, such as vacuum infiltration, pressure, sonication, and silicon carbide fiber agitation, are also known in the art and envisioned for use with any method provided herein.

Methods of transforming cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

Delivery vehicles, vectors, particles, nanoparticles, formulations and components thereof for expression of one or more elements of a nucleic acid molecule or a protein are as used in WO 2014/093622 (PCT/US2013/074667). In an aspect, a method of providing a nucleic acid molecule or a protein to a cell comprises delivery via a delivery particle. In an aspect, a method of providing a nucleic acid molecule or a protein to a cell comprises delivery via a delivery vesicle. In an aspect, a delivery vesicle is selected from the group consisting of an exosome and a liposome. In an aspect, a method of providing a nucleic acid molecule or a protein to a cell comprises delivery via a viral vector. In an aspect, a viral vector is selected from the group consisting of an adenovirus vector, a lentivirus vector, and an adeno-associated viral vector. In another aspect, a method providing a nucleic acid molecule or a protein to a cell comprises delivery via a nanoparticle. In an aspect, a method providing a nucleic acid molecule or a protein to a cell comprises microinjection. In an aspect, a method providing a nucleic acid molecule or a protein to a cell comprises polycations. In an aspect, a method providing a nucleic acid molecule or a protein to a cell comprises a cationic oligopeptide.

In an aspect, a delivery particle is selected from the group consisting of an exosome, an adenovirus vector, a lentivirus vector, an adeno-associated viral vector, a nanoparticle, a polycation, and a cationic oligopeptide. In an aspect, a method provided herein comprises the use of one or more delivery particles. In another aspect, a method provided herein comprises the use of two or more delivery particles. In another aspect, a method provided herein comprises the use of three or more delivery particles.

Suitable agents to facilitate transfer of proteins, nucleic acids, mutagens and ribonucleoproteins into a plant cell include agents that increase permeability of the exterior of the plant or that increase permeability of plant cells to oligonucleotides, polynucleotides, proteins, or ribonucleoproteins. Such agents to facilitate transfer of the composition into a plant cell include a chemical agent, or a physical agent, or combinations thereof. Chemical agents for conditioning includes (a) surfactants, (b) an organic solvents or an aqueous solutions or aqueous mixtures of organic solvents, (c) oxidizing agents, (e) acids, (f) bases, (g) oils, (h) enzymes, or combinations thereof Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils (such as those listed in the 9th Compendium of Herbicide Adjuvants, publicly available on line at herbicide [dot] adjuvants [dot] com) can be used, e.g., paraffinic oils, polyol fatty acid esters, or oils with short-chain molecules modified with amides or polyamines such as polyethyleneimine or N-pyrrolidine.

Examples of useful surfactants include sodium or lithium salts of fatty acids (such as tallow or tallowamines or phospholipids) and organosilicone surfactants. Other useful surfactants include organosilicone surfactants including nonionic organosilicone surfactants, e. g., trisiloxane ethoxylate surfactants or a silicone polyether copolymer such as a copolymer of polyalkylene oxide modified heptamethyl trisiloxane and allyloxypolypropylene glycol methylether (commercially available as Silwet® L-77).

Useful physical agents can include (a) abrasives such as carborundum, corundum, sand, calcite, pumice, garnet, and the like, (b) nanoparticles such as carbon nanotubes or (c) a physical force. Carbon nanotubes are disclosed by Kam et al. (2004)/. Am. Chem. Soc, 126 (22):6850-6851, Liu et al. (2009) Nano Lett, 9(3): 1007-1010, and Khodakovskaya et al. (2009) ACS Nano, 3(10):3221-3227. Physical force agents can include heating, chilling, the application of positive pressure, or ultrasound treatment. Embodiments of the method can optionally include an incubation step, a neutralization step (e.g., to neutralize an acid, base, or oxidizing agent, or to inactivate an enzyme), a rinsing step, or combinations thereof. The methods of the invention can further include the application of other agents which will have enhanced effect due to the silencing of certain genes. For example, when a polynucleotide is designed to regulate genes that provide herbicide resistance, the subsequent application of the herbicide can have a dramatic effect on herbicide efficacy.

Agents for laboratory conditioning of a plant cell to permeation by polynucleotides include, e.g., application of a chemical agent, enzymatic treatment, heating or chilling, treatment with positive or negative pressure, or ultrasound treatment. Agents for conditioning plants in a field include chemical agents such as surfactants and salts.

In an aspect, a transformed or transfected cell is a prokaryotic cell. In another aspect, a transformed or transfected cell is a eukaryotic cell. In another aspect, a transformed or transfected cell is a plant cell. In another aspect, a transformed or transfected cell is an animal cell. In another aspect, a transformed or transfected cell is a fungus cell.

Recipient plant cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell. Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat, Nos. 6,194,636 and 6,232,526 and U.S. Patent Application Publication 2004/0216189, all of which are incorporated herein by reference. Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction. In one aspect, this disclosure provides a non-reproductive plant cell.

In an aspect, any nucleic acid molecule, polypeptide, or ribonucleoprotein provided herein is within a cell. In another aspect, any nucleic acid molecule, polypeptide, or ribonucleoprotein provided herein a prokaryotic cell. In an aspect, any nucleic acid molecule, polypeptide, or ribonucleoprotein provided herein a eukaryotic cell.

In an aspect, any cell provided herein is a host cell. In an aspect, a host cell comprises any ribonucleoprotein provided herein. In an aspect, a host cell comprises any polypeptide provided herein. In an aspect, a host cell comprises any nucleic acid molecule provided herein.

In an aspect, a host cell is selected from the group consisting of a plant cell, a bacterial cell, a mammalian cell, a fungal cell, an insect cell, an arachnid cell, a bird cell, a fish cell, a reptile cell, and an amphibian cell. In another aspect, a host plant cell is selected from the group consisting of a corn cell, a soybean cell, a cotton cell, a canola cell, a rice cell, a wheat cell, a sorghum cell, an alfalfa cell, a sugarcane cell, a millet cell, a tomato cell, a potato cell, and an algae cell. In another aspect, a host cell is an *Escherichia coli* cell.

In an aspect, a prokaryotic cell is a cell from a phylum selected from the group consisting of prokaryotic cell is a cell from a phylum selected from the group consisting of Acidobacteria, Actinobacteria, Aquificae, Armatimonadetes, Bacteroidetes, Caldiserica, Chlamydie, Chlorobi, Chloroflexi, Chrysiogenetes, Coprothermobacterota, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospirae, Planctomycetes, Proteobacteria, Spirochaetes, Synergistetes, Tenericutes, Thermodesulfobacteria, Thermotogae, and Verrucomicrobia. In another aspect, a prokaryotic cell is an *Escherichia coli* cell. In another aspect, a prokaryotic cell is selected from a genus selected from the group consisting of *Escherichia, Agrobacterium, Rhizobium, Sinorhizobium,* and *Staphylococcus.*

In an aspect, a eukaryotic cell is an ex vivo cell. In another aspect, a eukaryotic cell is a plant cell. In another aspect, a eukaryotic cell is a plant cell in culture. In another aspect, a eukaryotic cell is an angiosperm plant cell. In another aspect, a eukaryotic cell is a gymnosperm plant cell. In another aspect, a eukaryotic cell is a monocotyledonous plant cell. In another aspect, a eukaryotic cell is a dicotyledonous plant cell. In another aspect, a eukaryotic cell is a corn cell. In another aspect, a eukaryotic cell is a rice cell. In another aspect, a eukaryotic cell is a sorghum cell. In another aspect, a eukaryotic cell is a wheat cell. In another aspect, a eukaryotic cell is a canola cell. In another aspect, a eukaryotic cell is an alfalfa cell. In another aspect, a eukaryotic cell is a soybean cell. In another aspect, a eukaryotic cell is a cotton cell. In another aspect, a eukaryotic cell is a tomato cell. In another aspect, a eukaryotic cell is a potato cell. In a further aspect, a eukaryotic cell is a cucumber cell. In another aspect, a eukaryotic cell is a millet cell. In another aspect, a eukaryotic cell is a barley cell. In another aspect, a eukaryotic cell is a Brassica cell. In another aspect, a eukaryotic cell is a grass cell. In another aspect, a eukaryotic cell is a Setaria cell. In another aspect, a eukaryotic cell is an Arabidopsis cell. In a further aspect, a eukaryotic cell is an algae cell.

In one aspect, a plant cell is an epidermal cell. In another aspect, a plant cell is a stomata cell. In another aspect, a plant cell is a trichome cell. In another aspect, a plant cell is a root cell. In another aspect, a plant cell is a leaf cell. In another aspect, a plant cell is a callus cell. In another aspect, a plant cell is a protoplast cell. In another aspect, a plant cell is a pollen cell. In another aspect, a plant cell is an ovary cell. In another aspect, a plant cell is a floral cell. In another aspect, a plant cell is a meristematic cell. In another aspect, a plant cell is an endosperm cell. In another aspect, a plant cell does not comprise reproductive material and does not mediate the natural reproduction of the plant. In another aspect, a plant cell is a somatic plant cell.

Additional provided plant cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue.

In a further aspect, a eukaryotic cell is an animal cell. In another aspect, a eukaryotic cell is an animal cell in culture. In a further aspect, a eukaryotic cell is a human cell. In another aspect, a eukaryotic cell is not a human stem cell. In a further aspect, a eukaryotic cell is a human cell in culture. In a further aspect, a eukaryotic cell is a somatic human cell. In a further aspect, a eukaryotic cell is a cancer cell. In a further aspect, a eukaryotic cell is a mammal cell. In a further aspect, a eukaryotic cell is a mouse cell. In a further aspect, a eukaryotic cell is a pig cell. In a further aspect, a eukaryotic cell is a bovid cell. In a further aspect, a eukaryotic cell is a bird cell. In a further aspect, a eukaryotic cell is a reptile cell. In a further aspect, a eukaryotic cell is an amphibian cell. In a further aspect, a eukaryotic cell is an insect cell. In a further aspect, a eukaryotic cell is an arthropod cell. In a further aspect, a eukaryotic cell is a cephalopod cell. In a further aspect, a eukaryotic cell is an arachnid cell. In a further aspect, a eukaryotic cell is a mollusk cell. In a further aspect, a eukaryotic cell is a nematode cell. In a further aspect, a eukaryotic cell is a fish cell.

In another aspect, a eukaryotic cell is a protozoan cell. In another aspect, a eukaryotic cell is a fungal cell. In an aspect, a fungal cell is a yeast cell. In an aspect, a yeast cell is a *Schizosaccharomyces pombe* cell. In another aspect, a yeast cell is a *Saccharomyces cerevisiae* cell.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise deoxyribonucleotides, ribonucleotides, or combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded.

As used herein, the term "recombinant" in reference to a nucleic acid (DNA or RNA) molecule, protein, construct, vector, etc., refers to a nucleic acid or amino acid molecule or sequence that is man-made and not normally found in nature, and/or is present in a context in which it is not normally found in nature, including a nucleic acid molecule (DNA or RNA) molecule, protein, construct, etc., comprising a combination of polynucleotide or protein sequences that would not naturally occur contiguously or in close proximity together without human intervention, and/or a polynucleotide molecule, protein, construct, etc., comprising at least two polynucleotide or protein sequences that are heterologous with respect to each other.

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo.

In an aspect, this disclosure provides a plasmid comprising any nucleic acid molecule provided herein. In another aspect, this disclosure provides a plasmid encoding any amino acid sequence provided herein. In another aspect, this disclosure provides a plasmid encoding any ribonucleoprotein provided herein.

In another aspect, a nucleic acid encoding a Cas12a nuclease or CasX nuclease is provided in a vector. In a further aspect, a nucleic acid encoding a linker is provided in a vector. In a further aspect, a nucleic acid encoding a HUH endonuclease is provided in a vector. In a further aspect, a nucleic acid encoding a guide nucleic acid is provided in a vector. In a further aspect, a nucleic acid encoding a template nucleic acid molecule is provided in a vector.

As used herein, the term "polypeptide" refers to a chain of at least two covalently linked amino acids. Polypeptides can be encoded by polynucleotides provided herein. An example of a polypeptide is a protein. Proteins provided herein can be encoded by nucleic acid molecules provided herein.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Without being limiting, nucleic acids can be detected using hybridization.

Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

The terms "percent sequence complementarity" or "percent complementarity" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

For optimal alignment of sequences to calculate their percent identity, various pair-wise or multiple sequence alignment algorithms and programs are known in the art, such as ClustalW or Basic Local Alignment Search Tool (BLAST®), etc., that can be used to compare the sequence identity or similarity between two or more nucleotide or protein sequences. Although other alignment and comparison methods are known in the art, the alignment and percent identity between two sequences (including the percent identity ranges described above) can be as determined by the ClustalW algorithm, see, e.g., Chenna R. et al., "Multiple sequence alignment with the Clustal series of programs," *Nucleic Acids Research* 31: 3497-3500 (2003); Thompson JD et al., "Clustal W: Improving the sensitivity of progressive multiple sequence alignment through sequence weighting, position-specific gap penalties and weight matrix choice," *Nucleic Acids Research* 22: 4673-4680 (1994); Larkin MA et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

As used herein, a first nucleic acid molecule can "hybridize" a second nucleic acid molecule via non-covalent interactions (e.g., Watson-Crick base-pairing) in a sequence-specific, antiparallel manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine pairing with thymine, adenine pairing with uracil, and guanine (G) pairing with cytosine (C) [DNA, RNA]. In addition, it is also known in the art that for hybridization between two RNA molecules (e.g., dsRNA), guanine base pairs with uracil. For example, G/U base-pairing is partially responsible for the degeneracy (redundancy) of the genetic code in the context of tRNA anti-codon base-pairing with codons in mRNA. In the context of this disclosure, a guanine of a protein-binding segment (dsRNA duplex) of a subject DNA-targeting RNA molecule is considered complementary to an uracil, and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer nucleotides) the position of mismatches becomes important (see Sambrook et al.). Typically, the length for a hybridizable nucleic acid is at least 10 nucleotides. Illustrative minimum lengths for a hybridizable nucleic acid are: at least 15 nucleotides; at least 18 nucleotides; at least 20 nucleotides; at least 22 nucleotides; at least 25 nucleotides; and at least 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST® programs (basic local alignment search tools) and PowerBLAST programs known in the art (see Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

As used herein, "in vivo" refers to within a living cell, tissue, or organism. As used herein, "in vitro" refers to within a labware. Non-limiting examples of labware include a test tube, a flask, a beaker, a graduated cylinder, a pipette, a petri dish, and a microtiter plate. As used herein, "ex vivo" refers to in a cell or tissue from an organism in an external environment. "Ex planta" refers to a plant cell or tissue in an external environment, while "in planta" refers to a cell within a living plant. As a non-limiting example, a plant protoplast in a petri dish or test tube would be considered both ex vivo and ex planta.

In an aspect, any nucleic acid molecule or polypeptide provided herein can be used in vivo. In an aspect, any nucleic acid molecule or polypeptide provided herein can be used in vitro. In an aspect, any nucleic acid molecule or polypeptide provided herein can be used ex vivo. In an aspect, any nucleic acid molecule or polypeptide provided herein can be used in planta. In an aspect, any nucleic acid molecule or polypeptide provided herein can be used ex planta.

In an aspect, any cell provided herein is present in vivo. In an aspect, any cell provided herein is present in vitro. In an aspect, any cell provided herein is present ex vivo. In an aspect, any plant cell provided herein is present in planta. In an aspect, any plant cell provided herein is present ex planta.

As commonly understood in the art, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, inducible, etc.

In an aspect, a recombinant nucleic acid provided herein comprises at least one promoter. In another aspect, a polynucleotide encoding a Cas12a nuclease is operably linked to at least one promoter. In another aspect, a polynucleotide encoding a CasX nuclease is operably linked to at least one promoter. In another aspect, a polynucleotide encoding a HUH endonuclease is operably linked to at least one promoter. In another aspect, a polynucleotide encoding a FBNYV HUH endonuclease is operably linked to at least one promoter. In another aspect, a polynucleotide encoding a PCV HUH endonuclease is operably linked to at least one promoter. In another aspect, a polynucleotide encoding a guide nucleic acid is operably linked to at least one promoter. In another aspect, a polynucleotide encoding a template nucleic acid molecule is operably linked to at least one promoter.

Promoters that drive expression in all or most tissues of the plant are referred to as "constitutive" promoters. Promoters that drive expression during certain periods or stages of development are referred to as "developmental" promoters. Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. Promoters that express within a specific tissue(s) of an organism, with little or no expression in other tissues, are referred to as "tissue-specific" promoters. An "inducible" promoter is a promoter that initiates transcription in response to an environmental stimulus such as heat, cold, drought, light, or other stimuli, such as wounding or chemical application. A promoter can also be classified in terms of its origin, such as being heterologous, homologous, chimeric, synthetic, etc.

As used herein, the term "heterologous" in reference to a promoter is a promoter sequence having a different origin relative to its associated transcribable DNA sequence, coding sequence or gene (or transgene), and/or not naturally occurring in the plant species to be transformed. The term "heterologous" can refer more broadly to a combination of two or more DNA molecules or sequences, such as a promoter and an associated transcribable DNA sequence, coding sequence or gene, when such a combination is man-made and not normally found in nature.

In an aspect, a promoter provided herein is a constitutive promoter. In another aspect, a promoter provided herein is a tissue-specific promoter. In a further aspect, a promoter provided herein is a tissue-preferred promoter. In still another aspect, a promoter provided herein is an inducible promoter. In an aspect, a promoter provided herein is selected from the group consisting of a constitutive promoter, a tissue-specific promoter, a tissue-preferred promoter, and an inducible promoter.

RNA polymerase III (Pol III) promoters can be used to drive the expression of non-protein coding RNA molecules. In an aspect, a promoter provided herein is a Pol III promoter. In another aspect, a Pol III promoter provided herein is operably linked to a nucleic acid molecule encoding a non-protein coding RNA. In yet another aspect, a Pol III promoter provided herein is operably linked to a nucleic acid molecule encoding a guide nucleic acid. In still another aspect, a Pol III promoter provided herein is operably linked to a nucleic acid molecule encoding a single-guide RNA. In a further aspect, a Pol III promoter provided herein is operably linked to a nucleic acid molecule encoding a CRISPR RNA (crRNA). In another aspect, a Pol III promoter provided herein is operably linked to a nucleic acid molecule encoding a tracer RNA (tracrRNA).

Non-limiting examples of Pol III promoters include a U6 promoter, an H1 promoter, a 5S promoter, an Adenovirus 2 (Ad2) VAI promoter, a tRNA promoter, and a 7SK promoter. See, for example, Schramm and Hernandez, 2002, *Genes & Development*, 16:2593-2620, which is incorporated by reference herein in its entirety. In an aspect, a Pol III promoter provided herein is selected from the group consisting of a U6 promoter, an H1 promoter, a 5S promoter, an Adenovirus 2 (Ad2) VAI promoter, a tRNA promoter, and a 7SK promoter. In another aspect, a guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a single-guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a CRISPR RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a tracer RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter.

In an aspect, a promoter provided herein is a Dahlia Mosaic Virus (DaMV) promoter. In another aspect, a promoter provided herein is a U6 promoter. In another aspect, a promoter provided herein is an actin promoter.

Examples describing a promoter that can be used herein include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Molecular Biology* (1987) 9: 315-324), the CaMV 35S promoter (Odell et al., *Nature* (1985) 313: 810-812), the figwort mosaic virus 35S-promoter (U.S. Pat. Nos. 6,051,753; 5,378,619), the sucrose synthase promoter (Yang and Russell, *Proceedings of the National Academy of Sciences*, USA (1990) 87: 4144-4148), the R gene complex promoter (Chandler et al., *Plant Cell* (1989) 1: 1175-1183), and the chlorophyll a/b binding protein gene promoter, PC1SV (U.S. Pat. No. 5,850, 019), and AGRtu.nos (GenBank Accession V00087; Depicker et al., *Journal of Molecular and Applied Genetics* (1982) 1: 561-573; Bevan et al., 1983) promoters.

Promoter hybrids can also be used and constructed to enhance transcriptional activity (see U.S. Pat. No. 5,106, 739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

It is appreciated in the art that a fragment of a promoter sequence can function to drive transcription of an operably linked nucleic acid molecule. For example, without being limiting, if a 1000 bp promoter is truncated to 500 bp, and the 500 bp fragment is capable of driving transcription, the 500 bp fragment is referred to as a "functional fragment."

As used herein, a "nuclear localization signal" (NLS) refers to an amino acid sequence that "tags" a protein for import into the nucleus of a cell. In an aspect, a nucleic acid molecule provided herein encodes a nuclear localization signal. In another aspect, a nucleic acid molecule provided herein encodes two or more nuclear localization signals.

In an aspect, a Cas12a nuclease provided herein comprises a nuclear localization signal. In an aspect, a nuclear localization signal is positioned on the N-terminal end of a Cas12a nuclease. In a further aspect, a nuclear localization signal is positioned on the C-terminal end of a Cas12a nuclease. In yet another aspect, a nuclear localization signal is positioned on both the N-terminal end and the C-terminal end of a Cas12a nuclease.

In an aspect, a CasX nuclease provided herein comprises a nuclear localization signal. In an aspect, a nuclear localization signal is positioned on the N-terminal end of a CasX nuclease. In a further aspect, a nuclear localization signal is positioned on the C-terminal end of a CasX nuclease. In yet another aspect, a nuclear localization signal is positioned on both the N-terminal end and the C-terminal end of a CasX nuclease.

In an aspect, a HUH endonuclease provided herein comprises a nuclear localization signal. In an aspect, a nuclear localization signal is positioned on the N-terminal end of a HUH endonuclease. In a further aspect, a nuclear localization signal is positioned on the C-terminal end of a HUH endonuclease. In yet another aspect, a nuclear localization signal is positioned on both the N-terminal end and the C-terminal end of a HUH endonuclease.

In an aspect, a FBNYV HUH endonuclease provided herein comprises a nuclear localization signal. In an aspect, a nuclear localization signal is positioned on the N-terminal end of a FBNYV HUH endonuclease. In a further aspect, a nuclear localization signal is positioned on the C-terminal end of a FBNYV HUH endonuclease. In yet another aspect, a nuclear localization signal is positioned on both the N-terminal end and the C-terminal end of a FBNYV HUH endonuclease.

In an aspect, a PCV HUH endonuclease provided herein comprises a nuclear localization signal. In an aspect, a nuclear localization signal is positioned on the N-terminal end of a PCV HUH endonuclease. In a further aspect, a nuclear localization signal is positioned on the C-terminal end of a PCV HUH endonuclease. In yet another aspect, a nuclear localization signal is positioned on both the N-terminal end and the C-terminal end of a PCV HUH endonuclease.

In an aspect, a ribonucleoprotein comprises at least one nuclear localization signal. In another aspect, a ribonucleoprotein comprises at least two nuclear localization signals.

In an aspect, a nuclear localization signal provided herein is encoded by SEQ ID NO: 8. In an aspect, a nuclear localization signal provided herein is encoded by SEQ ID NO: 9. In another aspect, a nuclear localization signal is selected from the group consisting of SEQ ID NOs: 8 and 9.

Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www[dot]kazusa[dot] or[dot]jp[forwards slash]codon and these tables can be adapted in a number of ways. See Nakamura et al., 2000, *Nucl. Acids Res.* 28:292. Computer algorithms for codon optimizing a particular sequence for expression in a particular host cell are also available, such as Gene Forge (Aptagen; Jacobus, PA), are also available.

As used herein, "codon optimization" refers to a process of modifying a nucleic acid sequence for enhanced expression in a host cell of interest by replacing at least one codon (e.g., at least 1, 2, 3, 4, 5, 10, 15, 20, 25, 50, or more codons) of a sequence with codons that are more frequently or most frequently used in the genes of the host cell while maintaining the original amino acid sequence (e.g., introducing silent mutations).

In an aspect, one or more codons (e.g., 1, 2, 3, 4, 5, 10, 15, 20, 25, 50, or more, or all codons) in a sequence encoding a Cas12a nuclease, a CasX nuclease, or a HUH endonuclease correspond to the most frequently used codon for a particular amino acid. As to codon usage in plants, including algae, reference is made to Campbell and Gowri, 1990, *Plant Physiol.*, 92: 1-11; and Murray et al., 1989, *Nucleic Acids Res.*, 17:477-98, each of which is incorporated herein by reference in their entireties.

In one aspect, a nucleic acid molecule provided herein encodes a Cas12a nuclease that is codon optimized for a prokaryotic cell. In one aspect, a nucleic acid molecule provided herein encodes a Cas12a nuclease that is codon optimized for a *Escherichia coli* cell. In one aspect, a nucleic acid molecule provided herein encodes a Cas12a nuclease that is codon optimized for a eukaryotic cell. In an aspect, a nucleic acid molecule provided herein is codon optimized for an animal cell. In an aspect, a nucleic acid molecule provided herein is codon optimized for a fungus cell. In an aspect, a nucleic acid molecule provided herein is codon optimized for a yeast cell. In another aspect, a nucleic acid molecule provided herein encodes a Cas12a nuclease that is codon optimized for a plant cell. In another aspect, a nucleic acid molecule provided herein encodes a Cas12a nuclease that is codon optimized for a monocotyledonous plant species. In another aspect, a protein-coding nucleic acid molecule is codon optimized for a dicotyledonous plant species. In a further aspect, a nucleic acid molecule provided herein encodes a Cas12a nuclease that is codon optimized for a gymnosperm plant species. In a further aspect, a nucleic acid molecule provided herein encodes a Cas12a nuclease that is codon optimized for an angiosperm plant species. In a further aspect, a nucleic acid molecule provided herein encodes a Cas12a nuclease that is codon optimized for a corn cell. In a further aspect, a nucleic acid molecule provided herein encodes a Cas12a nuclease that is codon optimized for a soybean cell. In a further aspect, a nucleic acid molecule provided herein encodes a Cas12a nuclease that is codon optimized for a rice cell. In a further aspect, a nucleic acid molecule provided herein encodes a Cas12a nuclease that is codon optimized for a wheat cell. In a further aspect, a nucleic acid molecule provided herein encodes a Cas nuclease that is codon optimized for a cotton cell. In a further aspect, a nucleic acid molecule provided herein encodes a Cas12a nuclease that is codon optimized for a sorghum cell. In a further aspect, a nucleic acid molecule provided herein encodes a Cas nuclease that is codon optimized for an alfalfa cell. In a further aspect, a nucleic acid molecule provided herein encodes a Cas12a nuclease that is codon optimized for a sugar cane cell. In a further aspect, a nucleic acid molecule provided herein encodes a Cas12a nuclease that is codon optimized for an Arabidopsis cell. In a further aspect, a nucleic acid molecule provided herein encodes a Cas12a nuclease that is codon optimized for a tomato cell. In a further aspect, a nucleic acid molecule provided herein encodes a Cas12a nuclease that is codon optimized for a cucumber cell. In a further aspect, a nucleic acid molecule provided herein encodes a Cas12a nuclease that is codon optimized for a potato cell. In a further aspect, a nucleic acid molecule provided herein encodes a Cas12a nuclease that is codon optimized for an algae cell.

In one aspect, a nucleic acid molecule provided herein encodes a CasX nuclease that is codon optimized for a prokaryotic cell. In one aspect, a nucleic acid molecule provided herein encodes a CasX nuclease that is codon optimized for a *Escherichia coli* cell. In one aspect, a nucleic acid molecule provided herein encodes a CasX nuclease that is codon optimized for a eukaryotic cell. In an aspect, a nucleic acid molecule provided herein is codon optimized for an animal cell. In an aspect, a nucleic acid molecule provided herein is codon optimized for a fungus cell. In an aspect, a nucleic acid molecule provided herein is codon optimized for a yeast cell. In another aspect, a nucleic acid molecule provided herein encodes a CasX nuclease that is codon optimized for a plant cell. In another aspect, a nucleic acid molecule provided herein encodes a CasX nuclease that is codon optimized for a monocotyledonous plant species. In another aspect, a protein-coding nucleic acid molecule is codon optimized for a dicotyledonous plant species. In a further aspect, a nucleic acid molecule provided herein encodes a CasX nuclease that is codon optimized for a gymnosperm plant species. In a further aspect, a nucleic acid molecule provided herein encodes a CasX nuclease that is codon optimized for an angiosperm plant species. In a further aspect, a nucleic acid molecule provided herein encodes a CasX nuclease that is codon optimized for a corn cell. In a further aspect, a nucleic acid molecule provided herein encodes a CasX nuclease that is codon optimized for a soybean cell. In a further aspect, a nucleic acid molecule provided herein encodes a CasX nuclease that is codon optimized for a rice cell. In a further aspect, a nucleic acid molecule provided herein encodes a CasX nuclease that is codon optimized for a wheat cell. In a further aspect, a nucleic acid molecule provided herein encodes a CasX nuclease that is codon optimized for a cotton cell. In a further aspect, a nucleic acid molecule provided herein encodes a CasX nuclease that is codon optimized for a sorghum cell. In a further aspect, a nucleic acid molecule provided herein encodes a CasX nuclease that is codon optimized for an alfalfa cell. In a further aspect, a nucleic acid molecule provided herein encodes a CasX nuclease that is codon optimized for a sugar cane cell. In a further aspect, a nucleic acid molecule provided herein encodes a CasX nuclease that is codon optimized for an *Arabidopsis* cell. In a further aspect, a nucleic acid molecule provided herein encodes a CasX nuclease that is codon optimized for a tomato cell. In a further aspect, a nucleic acid molecule provided herein encodes a CasX nuclease that is codon optimized for a cucumber cell. In a further aspect, a nucleic acid molecule provided herein encodes a CasX nuclease that is codon optimized for a potato cell. In a further aspect, a nucleic acid molecule provided herein encodes a CasX nuclease that is codon optimized for an algae cell.

In one aspect, a nucleic acid molecule provided herein encodes a HUH endonuclease that is codon optimized for a prokaryotic cell. In one aspect, a nucleic acid molecule provided herein encodes a HUH endonuclease that is codon optimized for a *Escherichia coli* cell. In one aspect, a nucleic acid molecule provided herein encodes a HUH endonuclease that is codon optimized for a eukaryotic cell. In an aspect, a nucleic acid molecule provided herein is codon optimized for an animal cell. In an aspect, a nucleic acid molecule provided herein is codon optimized for a fungus cell. In an aspect, a nucleic acid molecule provided herein is codon optimized for a yeast cell. In another aspect, a nucleic acid molecule provided herein encodes a HUH endonuclease that is codon optimized for a plant cell. In another aspect, a nucleic acid molecule provided herein encodes a HUH endonuclease that is codon optimized for a monocotyledonous plant species. In another aspect, a protein-coding nucleic acid molecule is codon optimized for a dicotyledonous plant species. In a further aspect, a nucleic acid molecule provided herein encodes a HUH endonuclease that is codon optimized for a gymnosperm plant species. In a further aspect, a nucleic acid molecule provided herein encodes a HUH endonuclease that is codon optimized for an angiosperm plant species. In a further aspect, a nucleic acid molecule provided herein encodes a HUH endonuclease that is codon optimized for a corn cell. In a further aspect, a nucleic acid molecule provided herein encodes a HUH endonuclease that is codon optimized for a soybean cell. In a further aspect, a nucleic acid molecule provided herein encodes a HUH endonuclease that is codon optimized for a rice cell. In a further aspect, a nucleic acid molecule provided herein encodes a HUH endonuclease that is codon optimized for a wheat cell. In a further aspect, a nucleic acid molecule provided herein encodes a HUH endonuclease that is codon optimized for a cotton cell. In a further aspect, a nucleic acid molecule provided herein encodes a HUH endonuclease that is codon optimized for a sorghum cell. In a further aspect, a nucleic acid molecule provided herein encodes a HUH endonuclease that is codon optimized for an alfalfa cell. In a further aspect, a nucleic acid molecule provided herein encodes a HUH endonuclease that is codon optimized for a sugar cane cell. In a further aspect, a nucleic acid molecule provided herein encodes a HUH endonuclease that is codon optimized for an *Arabidopsis* cell. In a further aspect, a nucleic acid molecule provided herein encodes a HUH endonuclease that is codon optimized for a tomato cell. In a further aspect, a nucleic acid molecule provided herein encodes a HUH endonuclease that is codon optimized for a cucumber cell. In a further aspect, a nucleic acid molecule provided herein encodes a HUH endonuclease that is codon optimized for a potato cell. In a further aspect, a nucleic acid molecule provided herein encodes a HUH endonuclease that is codon optimized for an algae cell.

In one aspect, a nucleic acid molecule provided herein encodes a FBNYV HUH endonuclease that is codon optimized for a prokaryotic cell. In one aspect, a nucleic acid molecule provided herein encodes a FBNYV HUH endonuclease that is codon optimized for a *Escherichia coli* cell. In one aspect, a nucleic acid molecule provided herein encodes a FBNYV HUH endonuclease that is codon optimized for a eukaryotic cell. In an aspect, a nucleic acid molecule provided herein is codon optimized for an animal cell. In an aspect, a nucleic acid molecule provided herein is codon optimized for a fungus cell. In an aspect, a nucleic acid molecule provided herein is codon optimized for a yeast cell. In another aspect, a nucleic acid molecule provided herein encodes a FBNYV HUH endonuclease that is codon optimized for a plant cell. In another aspect, a nucleic acid molecule provided herein encodes a FBNYV HUH endonuclease that is codon optimized for a monocotyledonous plant species. In another aspect, a protein-coding nucleic acid molecule is codon optimized for a dicotyledonous plant species. In a further aspect, a nucleic acid molecule provided herein encodes a FBNYV HUH endonuclease that is codon optimized for a gymnosperm plant species. In a further aspect, a nucleic acid molecule provided herein encodes a FBNYV HUH endonuclease that is codon optimized for an angiosperm plant species. In a further aspect, a nucleic acid molecule provided herein encodes a FBNYV HUH endonuclease that is codon optimized for a corn cell. In a further aspect, a nucleic acid molecule provided herein encodes a FBNYV HUH endonuclease that is codon optimized for a soybean cell. In a further aspect, a nucleic acid molecule provided herein encodes a FBNYV HUH endonuclease that is codon optimized for a rice cell. In a further aspect, a nucleic acid molecule provided herein encodes a FBNYV HUH endonuclease that is codon optimized for a wheat cell. In a further aspect, a nucleic acid molecule provided herein encodes a FBNYV HUH endonuclease that is codon optimized for a cotton cell. In a further aspect, a nucleic acid molecule provided herein encodes a FBNYV HUH endonuclease that is codon optimized for a sorghum cell. In a further aspect, a nucleic acid molecule provided herein encodes a FBNYV HUH endonuclease that is codon optimized for an alfalfa cell. In a further aspect, a nucleic acid molecule provided herein encodes a FBNYV HUH endonuclease that is codon optimized for a sugar cane cell. In a further aspect, a nucleic acid molecule provided herein encodes a FBNYV HUH endonuclease that is codon optimized for an Arabidopsis cell. In a further aspect, a nucleic acid molecule provided herein encodes a FBNYV HUH endonuclease that is codon optimized for a tomato cell. In a further aspect, a nucleic acid molecule provided herein encodes a FBNYV HUH endonuclease that is codon optimized for a cucumber cell. In a further aspect, a nucleic acid molecule provided herein encodes a FBNYV HUH endonuclease that is codon optimized for a potato cell. In a further aspect, a nucleic acid molecule provided herein encodes a FBNYV HUH endonuclease that is codon optimized for an algae cell.

In one aspect, a nucleic acid molecule provided herein encodes a PCV HUH endonuclease that is codon optimized for a prokaryotic cell. In one aspect, a nucleic acid molecule provided herein encodes a PCV HUH endonuclease that is codon optimized for a *Escherichia coli* cell. In one aspect, a nucleic acid molecule provided herein encodes a PCV HUH endonuclease that is codon optimized for a eukaryotic cell. In an aspect, a nucleic acid molecule provided herein is codon optimized for an animal cell. In an aspect, a nucleic acid molecule provided herein is codon optimized for a fungus cell. In an aspect, a nucleic acid molecule provided herein is codon optimized for a yeast cell. In another aspect, a nucleic acid molecule provided herein encodes a PCV HUH endonuclease that is codon optimized for a plant cell. In another aspect, a nucleic acid molecule provided herein encodes a PCV HUH endonuclease that is codon optimized for a monocotyledonous plant species. In another aspect, a protein-coding nucleic acid molecule is codon optimized for a dicotyledonous plant species. In a further aspect, a nucleic acid molecule provided herein encodes a PCV HUH endonuclease that is codon optimized for a gymnosperm plant species. In a further aspect, a nucleic acid molecule provided herein encodes a PCV HUH endonuclease that is codon optimized for an angiosperm plant species. In a further aspect, a nucleic acid molecule provided herein encodes a PCV HUH endonuclease that is codon optimized for a corn cell. In a further aspect, a nucleic acid molecule provided herein encodes a PCV HUH endonuclease that is codon optimized for a soybean cell. In a further aspect, a nucleic acid molecule provided herein encodes a PCV HUH endonuclease that is codon optimized for a rice cell. In a further aspect, a nucleic acid molecule provided herein encodes a PCV HUH endonuclease that is codon optimized for a wheat cell. In a further aspect, a nucleic acid molecule provided herein encodes a PCV HUH endonuclease that is codon optimized for a cotton cell. In a further aspect, a nucleic acid molecule provided herein encodes a PCV HUH endonuclease that is codon optimized for a sorghum cell. In a further aspect, a nucleic acid molecule provided herein encodes a PCV HUH endonuclease that is codon optimized for an alfalfa cell. In a further aspect, a nucleic acid molecule provided herein encodes a PCV HUH endonuclease that is codon optimized for a sugar cane cell. In a further aspect, a nucleic acid molecule provided herein encodes a PCV HUH endonuclease that is codon optimized for an Arabidopsis cell. In a further aspect, a nucleic acid molecule provided herein encodes a PCV HUH endonuclease that is codon optimized for a tomato cell. In a further aspect, a nucleic acid molecule provided herein encodes a PCV HUH endonuclease that is codon optimized for a cucumber cell. In a further aspect, a nucleic acid molecule provided herein encodes a PCV HUH endonuclease that is codon optimized for a potato cell. In a further aspect, a nucleic acid molecule provided herein encodes a PCV HUH endonuclease that is codon optimized for an algae cell.

In one aspect, a nucleic acid molecule provided herein encodes a linker that is codon optimized for a prokaryotic cell. In one aspect, a nucleic acid molecule provided herein encodes a linker that is codon optimized for a *Escherichia coli* cell. In one aspect, a nucleic acid molecule provided herein encodes a linker that is codon optimized for a eukaryotic cell. In an aspect, a nucleic acid molecule provided herein is codon optimized for an animal cell. In an aspect, a nucleic acid molecule provided herein is codon optimized for a fungus cell. In an aspect, a nucleic acid molecule provided herein is codon optimized for a yeast cell. In another aspect, a nucleic acid molecule provided herein encodes a linker that is codon optimized for a plant cell. In another aspect, a nucleic acid molecule provided herein encodes a linker that is codon optimized for a monocotyledonous plant species. In another aspect, a protein-coding nucleic acid molecule is codon optimized for a dicotyledonous plant species. In a further aspect, a nucleic acid molecule provided herein encodes a linker that is codon optimized for a gymnosperm plant species. In a further aspect, a nucleic acid molecule provided herein encodes a linker that is codon optimized for an angiosperm plant species. In a further aspect, a nucleic acid molecule provided herein encodes a linker that is codon optimized for a corn cell. In a further aspect, a nucleic acid molecule provided herein encodes a linker that is codon optimized for a soybean cell. In a further aspect, a nucleic acid molecule provided herein encodes a linker that is codon optimized for a rice cell. In a further aspect, a nucleic acid molecule provided herein encodes a linker that is codon optimized for a wheat cell. In a further aspect, a nucleic acid molecule provided herein encodes a linker that is codon optimized for a cotton cell. In a further aspect, a nucleic acid molecule provided herein encodes a linker that is codon optimized for a sorghum cell. In a further aspect, a nucleic acid molecule provided herein encodes a linker that is codon optimized for an alfalfa cell. In a further aspect, a nucleic acid molecule provided herein encodes a linker that is codon optimized for a sugar cane cell. In a further aspect, a nucleic acid molecule provided herein encodes a linker that is codon optimized for an *Arabidopsis* cell. In a further aspect, a nucleic acid molecule provided herein encodes a linker that is codon optimized for a tomato cell. In a further aspect, a nucleic acid molecule provided herein encodes a linker that is codon optimized for a cucumber cell. In a further aspect, a nucleic acid molecule provided herein encodes a linker that is codon optimized for a potato cell. In a further aspect, a nucleic acid molecule provided herein encodes a linker that is codon optimized for an algae cell.

EXAMPLES

Example 1

Design of Expression Vectors

Cys-free LbCas12a protein (SEQ ID NO: 1) was fused to an HUH endonuclease (SEQ ID NO: 2) from Faba Bean Necrotic Yellow Virus (FBNYV) via a novel sixteen amino-acid-long flexible linker (SEQ ID NO: 3). One of the optimal features of the linker is the presence of a high number of glycine, serine, and threonine residues. Without being limited by any scientific theory, these residues are not hydrophobic and can readily associate with the solvent in between the two protein domains. Without being limited by any scientific theory, these residues are also among the most flexible amino acids thereby providing the linker the ability to adopt many different conformations which in turn allows the two protein domains the freedom to move relative to one another. Also without being limited by any scientific theory, the aspartic acid and glutamic acid residues are highly charged, a feature that promotes interaction with the solvent, reducing the likelihood of protein aggregation.

The sequences encoding the three components of the fusion protein (cys-free LbCas12a, linker, HUH) were codon-optimized for optimal expression in *Escherichia coli*. The nucleotide sequence encoding cys-free LbCas12a is set forth as SEQ ID NO: 4. The nucleotide sequence encoding HUH endonuclease is set forth as SEQ ID NO: 5, and the nucleotide sequence encoding the linker is set forth as SEQ ID NO:6. Both N- and C-terminal HUH fusion proteins were designed. The nucleotide sequence encoding the cys-free LbCas12a:linker:HUH is set forth as SEQ ID NO: 7 and the nucleotide sequence encoding the HUH :linker: cys-free LbCas12a is set forth as SEQ ID NO: 17. Nuclear localization signals (NLS) (SEQ ID NOs: 8 and 9) were introduced at the 5'- and 3'-ends of the LbCas12a-linker:HUH open reading frame, respectively. Additionally, a nucleotide sequence encoding a histidine (HIS) tag (SEQ ID NO:10) was introduced 5' to the 5' NLS sequence. The nucleotide sequence encoding the HIS tag:NLS1:cys-free LbCas12a: linker:HUH:NLS2 (referred to below as "cys-free LbCas12a:HUH") sequence was placed under the control of the P-Ec.tac promoter (SEQ ID NO:11) and inserted into a bacterial expression vector. Graphical illustrations of the N- and C-terminal HUH fusion protein expression cassettes are shown in FIG. 1B. A control expression vector comprising a HIS tag:NLS1:cys-freeLbCas12a:NLS2 (referred to below as "cys-free LbCas12a control") sequence under the control of the P-Ec.tac promoter was also designed. See FIG. 1B. cys-free LbCas12a:HUH and cys-free LbCas12a control proteins were expressed and purified from E. coli cells transformed with the expression vectors described above.

Example 2

Testing of Fusion Proteins

To test whether cys-free LbCas12a:HUH could recognize and cleave chromosomal DNA in the presence of a cognate guide RNA, three unique target sites within the soybean (Glycine max) genome were chosen. crRNAs were designed to guide the cys-free LbCas12a:HUH and cys-free LbCas12a control proteins to each target site. Ribonucleoprotein (RNP) complexes comprising the purified cys-free LbCas12a:HUH fusion protein or cys-free LbCas12a and cognate crRNAs were assembled.

A 70-nucleotide long ssDNA template was designed. The template comprises a 10-nucleotide signature motif flanked by homology arms that comprise homology to sequences flanking the GmTS1 site. The ssDNA template was fused to the 15-nucleotide origin (ori) HUH recognition sequence (SEQ ID NO:12) of PCV . As shown in Example 6, the ori sequence from PCV is compatible with the FBNYV HUH endonuclease.

This single-stranded DNA template (ssDNA template) was added to the RNP complex. Next, this tri-partite RNP complex (see FIG. 1A) was tested in vitro for the expected functionalities of the two fusion domains: (a) targeted DNA cleavage and (b) covalent tethering of the ssDNA template. A gel-shift assay was performed to investigate the covalent tethering of the ssDNA template to cys-free LbCas12a:HUH (see Table 1). The gel-shift assay confirmed that in the presence of cys-free LbCas12a:HUH, the ssDNA template migrated significantly slower than it did in the either the presence of either cys-free LbCas12a control or the ssDNA template in its unbound state (see Table 1). The slower migration is indicative of the formation of cys-free LbCas12a:HUH::ssDNA tethered complexes.

TABLE 1

Gel shift assay investigating the covalent tethering of the ssDNA template to cys-free LbCas12a:HUH.

| Assay type | cys-free LbCas12a:HUH | cys-free LbCas12a Control | crRNA | ssDNA template | Upward shift in ssDNA migration observed |
|---|---|---|---|---|---|
| Control | − | − | — | + | No |
| Test | + | − | crRNA-TS1 | + | Yes |
| Control | − | + | crRNA-TS1 | + | No |
| Control | − | + | crRNA-TS1 | − | N/A |
| Control | − | − | — | + | No |
| Test | + | − | crRNA-TS2 | + | Yes |
| Control | − | + | crRNA-TS2 | + | No |
| Control | − | + | crRNA-TS2 | − | N/A |
| Control | − | − | — | + | No |
| Test | + | − | crRNA-TS3 | + | Yes |
| Control | − | + | crRNA-TS3 | + | No |
| Control | − | + | crRNA-TS3 | − | N/A |

"+" indicates presence;
"−" indicates absence.
"TS1" revers to GmTS1;
"TS2" refers to GmTS2; and
"TS3" refers to GmTS3.
"N/A" refers to Not applicable.

The ability of cys-free LbCas12a:HUH to cleave target DNA was assessed via an in vitro assay. A 1020-nucleotide PCR amplicon spanning two of the target sites (GmTS1 and GmTS2) was generated from the wild type soybean germplasm A3555. The ability of cys-free LbCas12a:HUH to cleave the PCR amplicon at expected sites in the presence of the cognate crRNAs was tested. Cys-freeLbCas12a was used as a positive control and assays lacking nucleases served as negative controls.

Targeted-cleavage of PCR amplicon by cys-freeLbCas12a in the presence of crRNA-TS1 is expected to result in 892-nucleotide and 128-nucleotide digestion products. Targeted cleavage of PCR amplicon by cys-free LbCas12a in the presence of crRNA-TS2 is expected to result in 734-nucleotide and 286-nucleotide digestion products. As shown in Table 2, the PCR amplicon was digested by both the cys-free LbCas12a:HUH complexes and cys-free LbCas12a control complexes in the expected patterns.

TABLE 2

Investigating the cleavage capabilities of cys-free LbCas12a:HUH and cys-free LbCas12a control fusion proteins.

| Type of assay | cys-free LbCas12a:HUH | cys-free LbCas12a | crRNA | ssDNA | Digestion products observed |
|---|---|---|---|---|---|
| Test | + | − | crRNA-TS1 | + | 892 nt; 128 nt |
| Positive Control | − | + | crRNA-TS1 | + | 892 nt; 128 nt |
| Negative Control | − | − | crRNA-TS1 | + | none |
| Test | + | − | crRNA-TS2 | + | 734 nt; 286 nt |
| Positive Control | − | + | crRNA-TS2 | + | 734 nt; 286 nt |
| Negative Control | − | − | crRNA-TS2 | + | none |

"+" indicates presence;
"−" indicates absence.
"TS1" refers to GmTS1;
"TS2" refers to GmTS2.

Example 3

Testing of Fusion Proteins in Protoplasts

The tripartite cys-free LbCas12a:HUH/crRNA/ssDNA template RNP complex was tested for chromosome cleavage in protoplast cells. Protoplasts were prepared from soybean embryos and were subsequently transformed with the RNP complexes comprising cys-free LbCas12a:HUH/crRNA/ssDNA template and their positive control counterparts carrying cys-free LbCas12a, by standard methods known in the art. Negative controls included matching crRNAs and ssDNA templates, but no fusion proteins (see Table 3).

A qualitative assay (Table 3) was developed to investigate the activity of cys-free LbCas12a:HUH. Following a two-day incubation at room temperature, total genomic DNA was isolated from all samples and 1020 nucleotide PCR amplicons spanning target sites GmTS1 and GmTS2 were generated. The amplicons were expected to comprise a heterogenous population of DNA sequences that comprised wildtype and edited target sites, the latter comprising INDELs. The PCR amplified amplicons were subsequently re-digested by cys-free LbCas12a in vitro. Undigested amplicons, indicative of edited target sites, were observed in both test and positive controls. Undigested amplicons were undetectable in negative controls. Sequencing of the undigested fractions confirmed presence of targeted INDELS in both tests and positive controls.

TABLE 3

Assay investigating the activity of cys-freeLbCas12-HUH in protoplast cells.

| Type of Assay | PCR Amplicon | cys-free LbCas12a:HUH | cys-free LbCas12a | crRNA-TS2 | Template | Undigested Amplicons observed |
|---|---|---|---|---|---|---|
| Test | + | + | − | + | + | Yes |
| Positive control | + | − | + | + | + | Yes |

TABLE 3-continued

Assay investigating the activity of cys-freeLbCas12-HUH in protoplast cells.

| Type of Assay | PCR Amplicon | cys-free LbCas12a:HUH | cys-free LbCas12a | crRNA-TS2 | Template | Undigested Amplicons observed |
|---|---|---|---|---|---|---|
| Negative control | + | − | − | + | + | No |

"+" indicates presence; "−" indicates absence.

Figure 2:
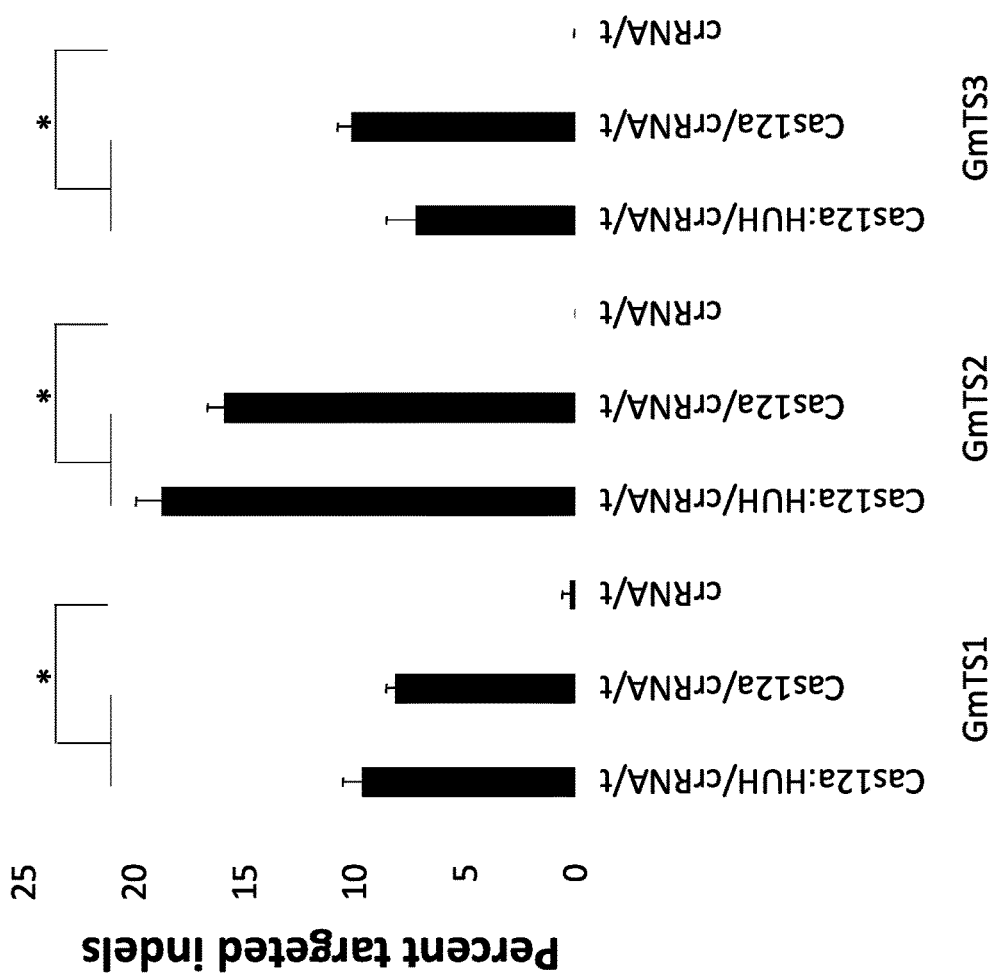
FIG. 2 depicts quantification of targeted indels by next generation sequencing at three target sites. Cys-free LbCas12a:HUH fusions and cys-free LbCas12a had comparable activities. Bars represent average indel rates of four technical replicates. Both experimental (cys-freeLbCas12a:HUH/crRNA/template) and positive controls (cys-free LbCas12a/crRNA/template) produced significantly higher percentages of indels compared to negative controls (crRNA/template) at p =0.05. "t" refers to template.

For quantitative comparison among treatments, amplicons spanning the target site were generated and sequenced by Next Generation Sequencing (NGS), by standard methods known in the art. Sequencing reads were considered mutant if they included indels in the seven-nucleotide LbCas12a cut site, which was positioned 18 to 24 nucleotides downstream of the LbCas12a PAM site. Seven to nineteen percent indel rates were detected in both test and positive controls across all three target sites tested. The negative controls had no more than 0.3% indel rates in the same region, which is significantly below the test/positive control cleavage rates for all sites (FIG. 2).

Example 4

In Planta Testing of Fusion Proteins

Figure 3:
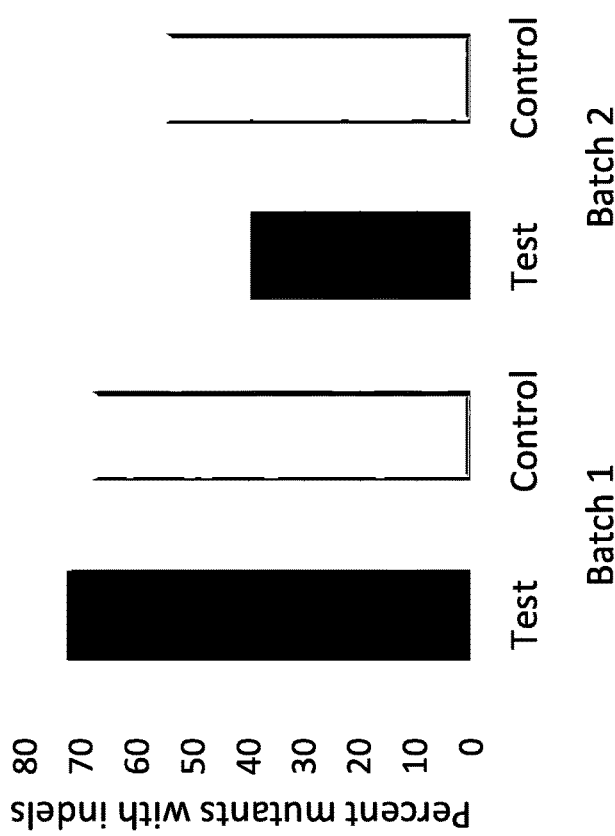
FIG. 3A shows a pictorial representations of test and control systems for testing fusion proteins in planta. The control system lacks an ori sequence required for the ssDNA template to bind to the HUH endonuclease.
FIG. 3B shows results from two independent particle bombardment experiments using the test and control systems shown FIG. 3A. Chromosome cleavage activities of Cas12a were determined by quantifying targeted indels within a seven nucleotide target site. Plants that generated at least 20% targeted indel reads are considered mutants.
Figure 3:
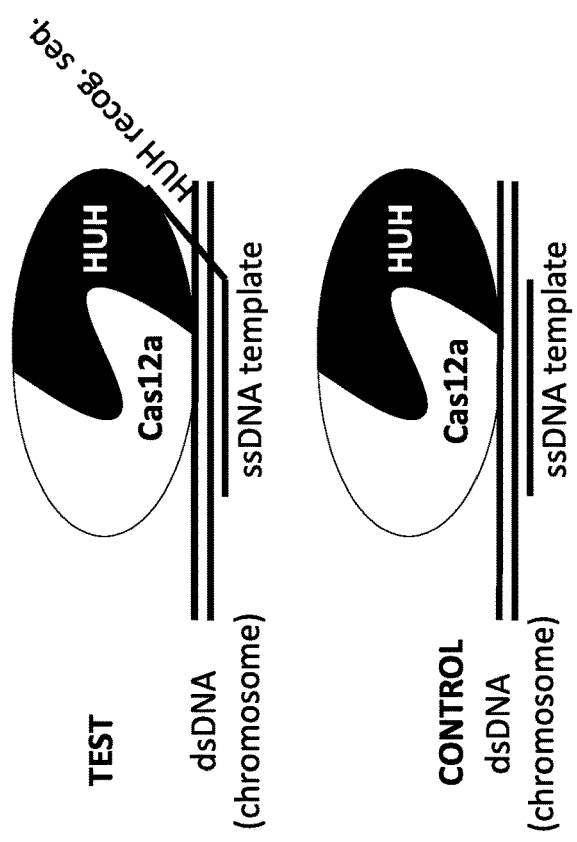

The cys-freeLbCas12a:HUH/crRNA/template complex was tested for chromosome cleavage and for targeted integrations in planta. The test and control samples both included the cys-freeLbCas12a:HUH fusion proteins and the crRNA for the GmTS1 target site as described in Example 1. The template in the Test assay included the ssDNA template comprising a 15-nucleotide ori HUH-recognition sequence from PCV as described in Example 2. The control assay comprised an ssDNA template that lacked the ori sequence. See FIG. 3A.

RNP complexes were assembled to be used for plant transformation. Two independent transformations were performed using particle bombardment. The RNP (cys-free LbCas12a:HUH/crRNA/template) complex together with a linear dsDNA fragment encoding for the spectinomycin resistance gene aadA was coated on 0.6$_1$,tm gold particles using a mixture of CaC12 and spermidine as coating agents. The coated particles were delivered into soybean dry excised embryos using the Biolistic PDS-1000/HE Particle Delivery System (Biorad).

Transformed seedlings were grown in tissue culture using spectinomycin for selection. Assuming near-stochiometric delivery of RNPs and the spectinomycin selectable marker gene, surviving plants were expected to be enriched for those carrying the RNP complex. Seedlings with at least one trifoliate leaf were sampled for DNA analysis.

Amplicons spanning the GmTS1 target site were generated and subjected to NGS using standard methods known in the art. Chromosome cleavage activity of cys-free LbCas12a:HUH was determined by quantifying the presence of targeted indels within the 7-nucleotide GmTS lcut site. Plants that generated at least 20% targeted indel reads were called mutants (see Table 4; and FIG. 3B). Mutation rates were >30% in all treatments, suggesting robust cleavage activity by the cys-freeLbCas12a:HUH fusion protein. (see Table 4; and FIG. 3B).

TABLE 4

Results of in planta editing using cys-free LbCas12a:HUH/crRNA/template with an ori sequence (Test) and cys-free LbCas12a:HUH/crRNA/template without an ori sequence (Control).

| | Batch 1 | | | Batch 2 | | |
|---|---|---|---|---|---|---|
| | Test | Control | P Value | Test | Control | P Value |
| Total R0 Events | 239 | 153 | | 113 | 182 | |
| Total mutants (20% mutant read threshold) | 173 | 104 | | 45 | 100 | |
| Percent mutants (20% mutant read threshold) | 72.4 | 68.0 | 0.35 | 39.8 | 54.9 | 0.010 |

Figure 4:
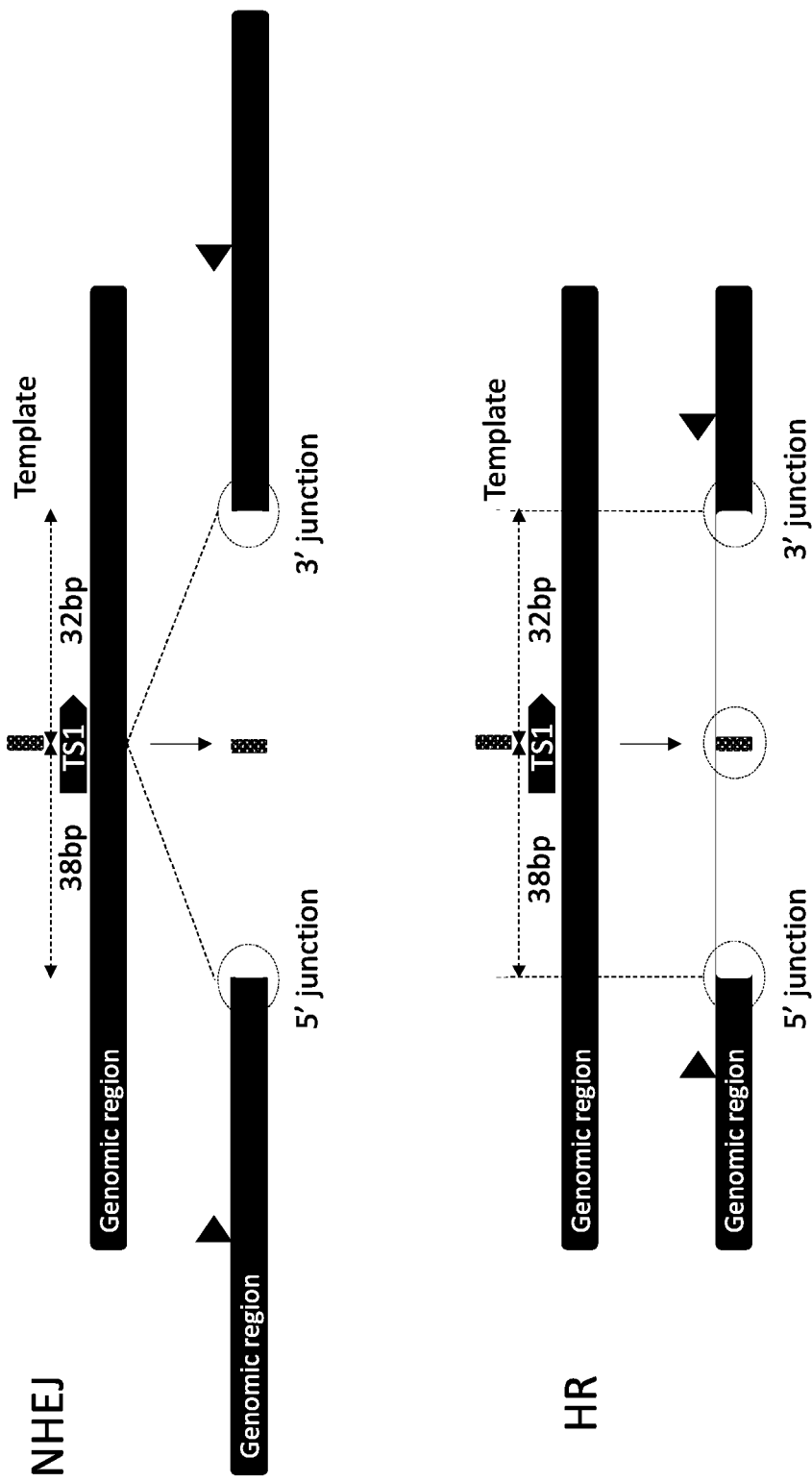
FIG. 4 depicts the genomic region flanking the GmTS1 target site and the matching, exogenous template added to the ribonucleoprotein complexes. The differential, middle signature motif of the template is shaded. Upon double-strand chromosome cutting, the template can integrate by non-homologous end-joining (NHEJ) or homologous recombination (HR). After sequencing, the presence/absence of the middle signature motif indicates targeted integration. The nature of integration, e.g., NHEJ, HR or a combination thereof is indicated by the sequences at the 5' and 3' chromosome-template junctions as shown. Not shown in this illustration is the ori recognition sequence that was present at the 5' end of the template used in the test samples. The ori recognition sequence was not present in the negative controls. Black triangles indicate PCR primers.

Targeted integrations were defined by the presence of a unique signature motif of the template in the NGS amplicons spanning the GmTS1 target site (see FIG. 4). Integrations can occur through two basic DNA repair processes, non-homologous end-joining (NHEJ) and homologous recombination (HR), or a combination of NHEJ and HR. Different template-chromosomes junctions are created by NHEJ and HR, which can be used to determine the mechanism of integration (see FIG. 4).

Figure 5:
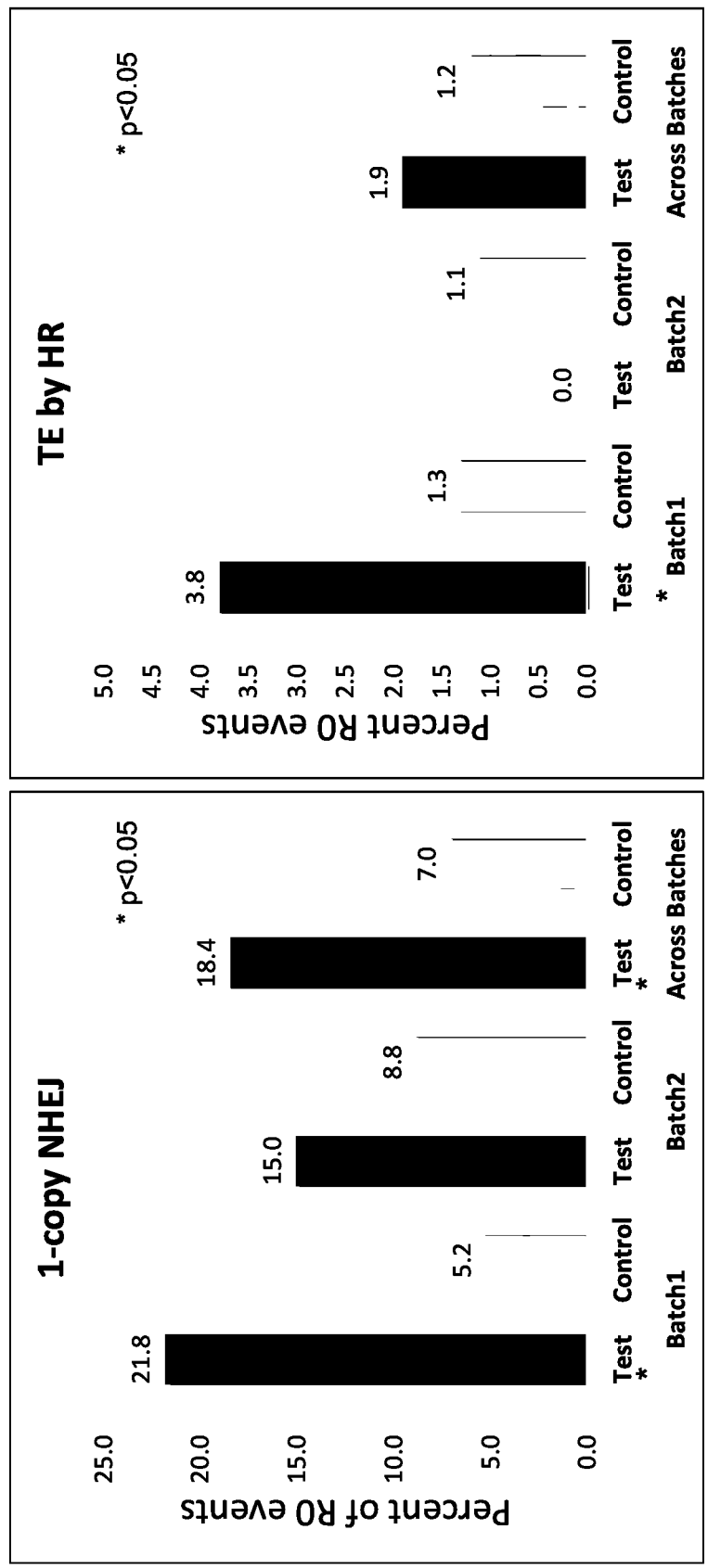
FIG. 5 shows the results from in planta testing of cys-free LbCas12a:HUH fusion proteins for targeted integrations in R0 plants.

Overall, HUH-mediated tethering of exogenous ssDNA to cys-free LbCas12a promoted targeted integrations (See Table 5; Table 6; and FIG. 5). For example, integration of single-copy template by NHEJ was significantly higher in tests as compared to controls in all batches. For homologous recombination, up to 3.8% integration was detected in tests as compared to no more than 1.3% in controls. Covalently tethering a ssDNA template to LbCas12a:HUH enhances targeted template integration in planta.

TABLE 5

In planta testing of LbCas12a:HUH fusion proteins for targeted integrations using cys-freeLbCas12a:HUH/crRNA/template with an ori sequence (Test) and cys-freeLbCas12a:HUH/crRNA/template without an ori sequence (Control).

| | Batch 1 | | Batch 2 | |
|---|---|---|---|---|
| | Test | Control | Test | Control |
| Total R0 Events | 239 | 153 | 113 | 182 |
| 1-copy NHEJ | 52 | 8 | 17 | 16 |
| 2-copy NHEJ | 3 | 0 | 2 | 2 |
| Total NHEJ | 55 | 8 | 19 | 18 |
| TE by HR | 9 | 2 | 0 | 2 |
| Total integration (NHEJ + HR) | 64 | 10 | 19 | 20 |

"TE" refers to templated editing via integration of template DNA by HR.
"1-copy" indicates single copy of the template inserted within the target site.
"2-copy" indicates two copies of the template integrated into the target site

TABLE 6

In planta testing of LbCas12a:HUH fusion proteins for targeted integrations using cys-free LbCas12a:HUH/crRNA/template with an ori sequence (Test) and cys-free LbCas12a:HUH/crRNA/template without an ori sequence (Control). Percentages are based on the total number of plants described above in Table 5. "TE" refers to templated editing via integration of template DNA by HR.

| | Batch 1 | | | Batch 2 | | | p-value across batches |
|---|---|---|---|---|---|---|---|
| | Test | Control | p-value | Test | Control | p-value | |
| Total R0 Events | 100% | 100% | N/A | 100% | 100% | N/A | N/A |
| 1-copy NHEJ | 21.8% | 5.20% | $2.8 \times 10^{-7}$* | 15.0% | 8.8% | 0.11 | 0.023* |
| 2-copy NHEJ | 1.3% | 0% | 0.16 | 1.8% | 1.1% | 0.64 | 0.15 |
| Total NHEJ | 23.1% | 5.20% | $5.07 \times 10^{-8}$* | 16.8% | 9.9% | 0.095 | 0.012* |
| TE by HR | 3.80% | 1.30% | 0.11 | 0.0% | 1.1% | 0.29 | 0.77 |
| Total integration (NHEJ + HR) | 26.9% | 6.5% | $6.79 \times 10^{-9}$* | 16.8% | 11.0% | 0.17 | 0.066 |

*indicates a statistically significant p-value.
N/A refers to not applicable.

Example 5

Testing of N- and C-Terminal HUH Fusion Proteins in Protoplasts

Figure 6:
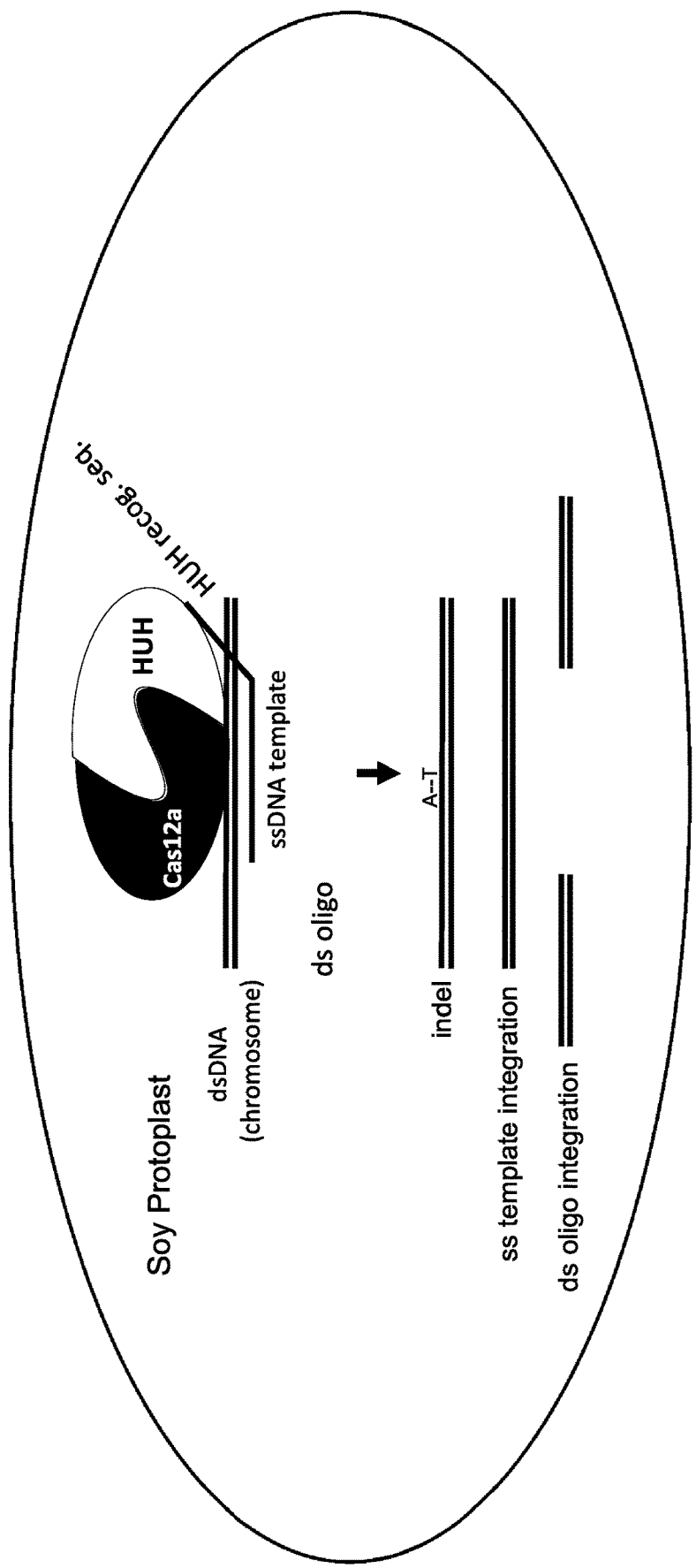
FIG. 6 shows the expected editing outcomes when RNP complexes comprising N-terminal or C-Terminal HUH fusion protein, crRNA targeting the GmTS1 genomic site, and templates comprising either a single-stranded DNA template (ss template) or a double-stranded DNA oligo (dsOligo) are concomitantly delivered into soy protoplasts.

The N- and C-terminal configurations of LbCas12a with FBNYV HUH fusion protein described in Example 1 and FIG. 1B were tested for targeted chromosome cleavage and subsequent DNA repair ex planta, at the GmTS1 target site in soy protoplasts (see FIG. 6). Protoplasts were transformed using various combinations of reagents as listed in Table 7 by standard methods known in the art. The reagents included the "N-terminal" (HUH: cys-free Lb C as12a) or the "C-terminal" (cys-free Lb C as12a: HUH) protein, the crRNA for the GmTS1 target site, a 70 nt ssDNA template (described in example 4) with or without the 5' PCV ori extension which facilitates tethering to the HUH domain and a 90 bp dsDNA oligonucleotide (dsDNA oligo).

TABLE 7

Combination of reagents used in the 16 protoplast treatments described in Example 5.

| | Treatments (Tr) | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| HUH:LbCas12a | + | + | − | − | + | + | − | − | − | − | + | − | + | − | − | − |
| LbCas12a:HUH | − | − | + | + | − | − | + | + | − | − | − | + | − | + | − | − |
| crRNA GmTS1 | + | + | + | + | + | + | + | + | + | + | + | + | − | − | + | + |
| ssTemplate + ori | + | − | + | − | + | − | + | − | + | − | − | − | − | − | + | − |
| ssTemplate | − | + | − | + | − | + | − | + | − | + | − | − | − | − | − | + |
| dsDNA Oligo | + | + | + | + | − | − | − | − | − | − | + | + | + | + | + | + |

"+" indicates presence.
"−" indicates absence.

After two days of incubation at room temperature, total genomic DNA was isolated. PCR was performed using primers flanking the Gm TS1 target site. The amplicons were sequenced using the MiSeq technology (illumina [dot] com). The sequences were analyzed for (1) targeted insertions and deletions (indels), (2) targeted integration of the ssDNA template by either HR or alternative mechanisms, which were collectively labeled as NHEJ-mediated integrations. In this latter case, single-copy and multiple-copy integrations were also distinguished. HR, by definition can integrate only one copy of the template. (3) Multiple-copy and single-copy integrations of the dsDNA oligonucleotide by NHEJ were also quantified.

Figure 7:
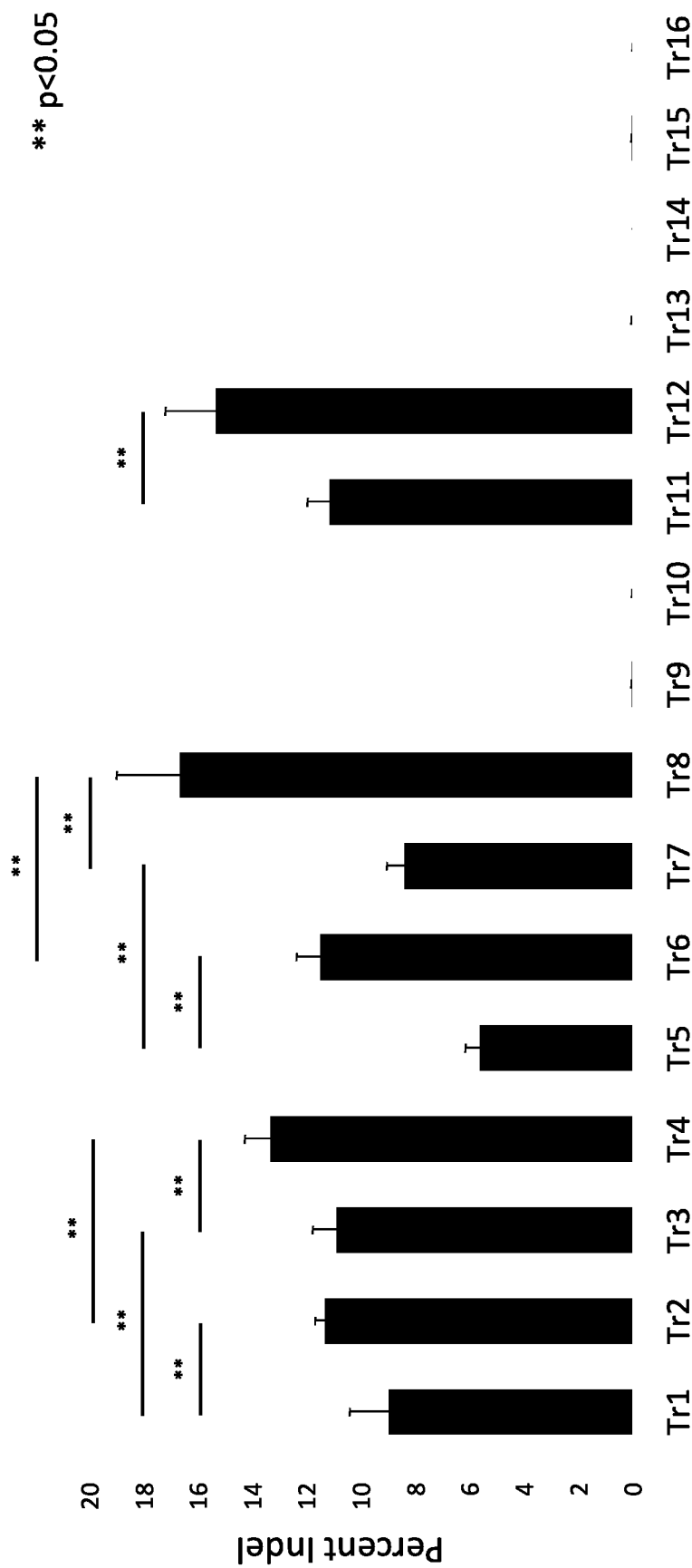
FIG. 7 shows chromosome cutting by N-terminal (HUH:cys-free LbCas12a) and C-Terminal (cys-free LbCas12a:HUH) fusion derivatives of LbCas12a across sixteen treatments (Tr) including various combinations of the enzymes, the cognate crRNA, ss templates with or without the ori sequence and a dsOligo with DNA sequence unrelated to the target region. See Table 7 for combination of reagents in each protoplast treatment. Chromosome cutting was quantified by targeted indel rates. Bars represent averages of four biological replicates, error bars are standard deviations. Statistical significance among a few important treatments are illustrated by horizontal lines above the bars.
Figure 8:
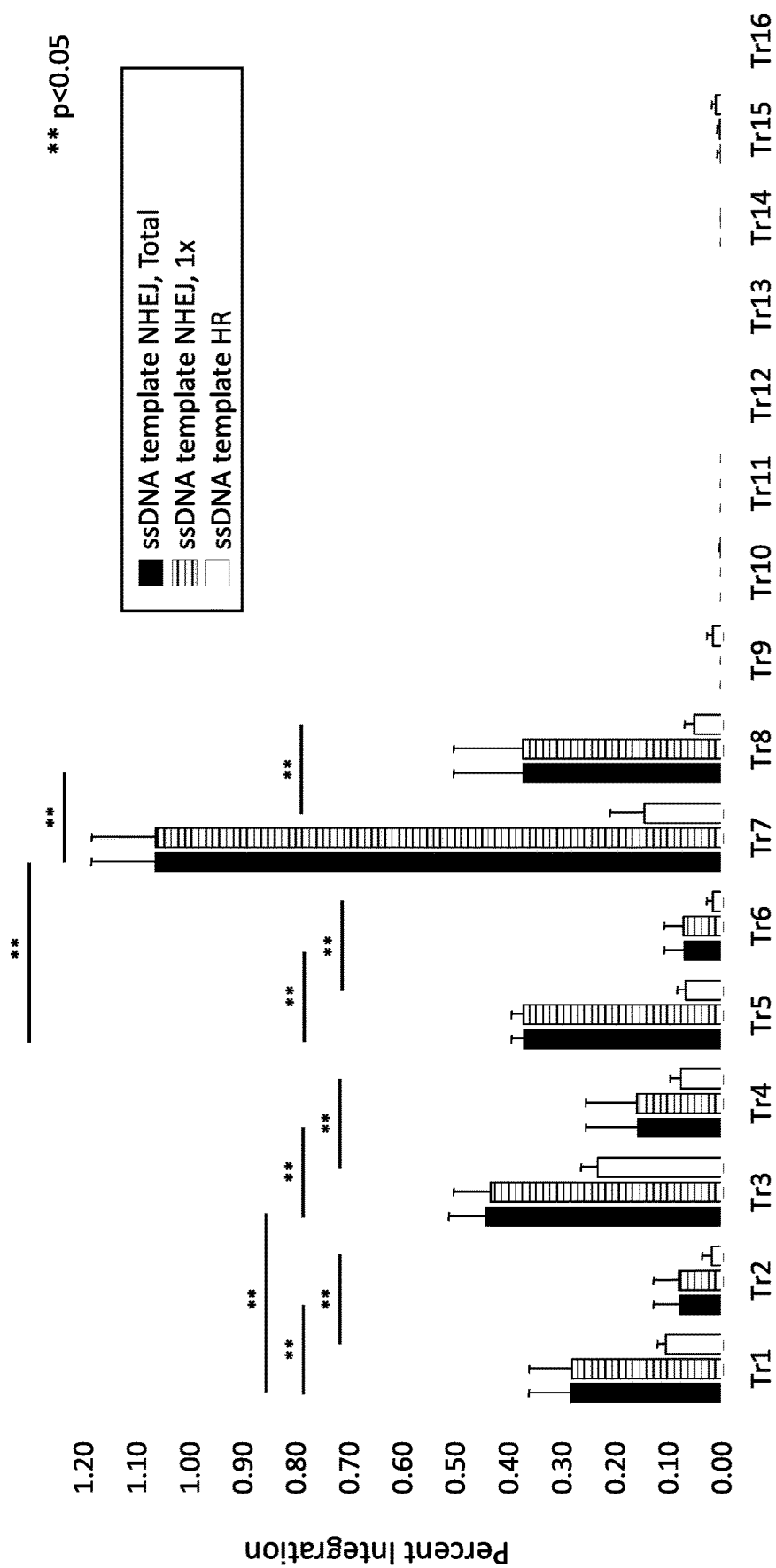
FIG. 8 shows targeted integrations of templates using N-terminal (HUH:cys-free LbCas12a) and C-terminal (cys-free LbCas12a:HUH) fusion derivatives of LbCas12a. Bars represent averages of four biological replicates, error bars are standard deviations. Total integrations by NHEJ (sum of targeted single- and multiple-copy integrations; black bars), single-copy integrations by NHEJ (dark gray bars) and templated edits by HR (light gray bars) were all significantly better when the templates were tethered to the RNP complexes. See Table 7 for combination of reagents in each treatment. Statistical significance among a few important treatments are illustrated by horizontal lines above the bars.
Figure 9:
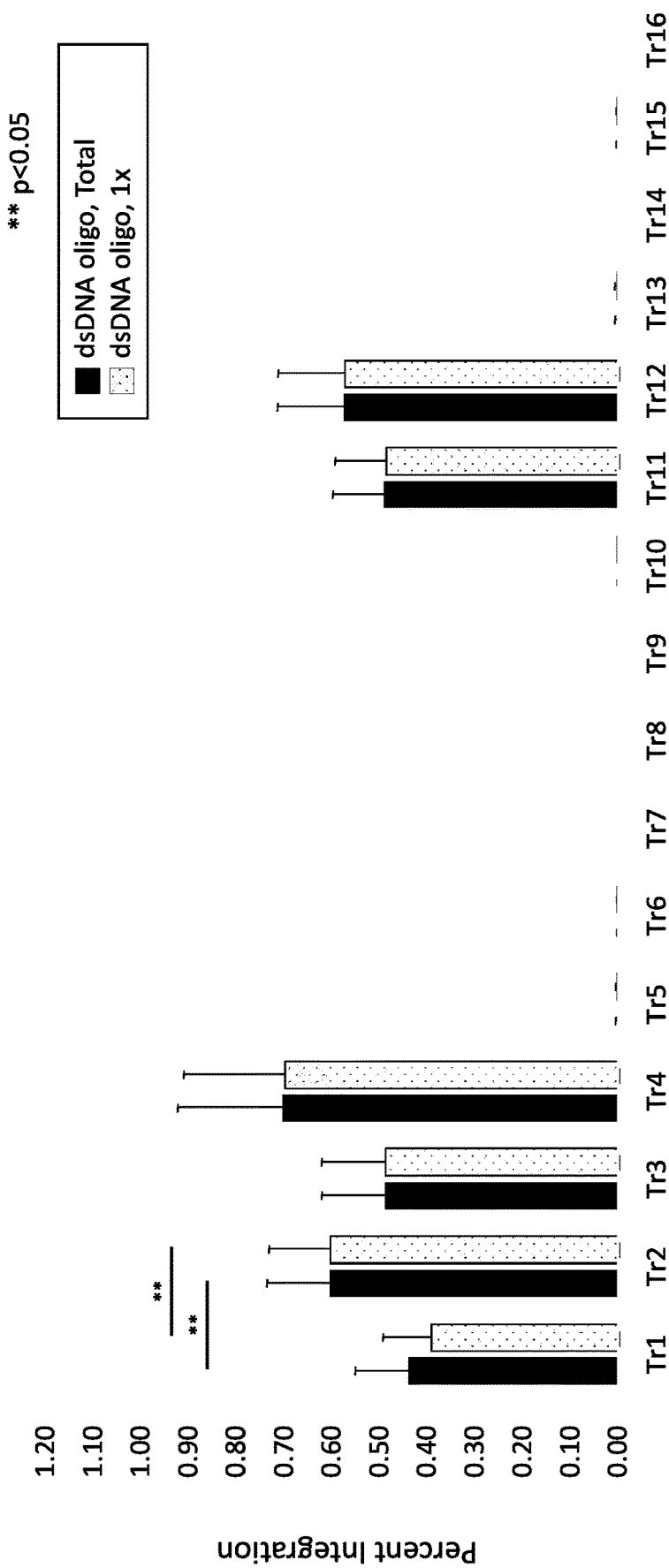
FIG. 9 shows targeted integrations of an exogenous, untethered ds oligonucleotide (90bp) by NHEJ using N-terminal (HUH:cys-free LbCas12a) and C-terminal (cys-free LbCas12a:HUH) fusion derivatives of LbCas12a. Bars represent averages of four biological replicates, error bars are standard deviations. "dsDNA oligo, Total" indicates sum of targeted single- and multiple-copy integrations by NHEJ (black bars). "dsDNA oligo, 1x" indicates single-copy integrations by NHEJ (dark gray bars). See Table 7 for combination of reagents in each treatment. Statistical significance among a few important treatments are illustrated by horizontal lines above the bars.

Chromosome cutting was confirmed for both N- and C-terminal enzyme configurations (HUH:cys-free LbCas12a and cys-free LbCas12a:HUH) as evidenced by the presence of indels at the target site in the presence of either fusion protein and cognate gRNA. See for example treatments 1-8, 11 and 12 compared to the control treatments 13-16 in FIG. 7. Cys-free LbCas12a:HUH ("C-terminal" fusion) showed higher indel rates and therefore better cutting rates than HUH: cys-free LbCas12a ("N-terminal fusion"). Tethering the ssDNA template to the HUH domain adversely affected chromosome cutting rates. Without being bound by any particular theory, spatial interference between the DNA template and the Cas12a-chromosome interface could interfere with nuclease activity. However, template integration by NHEJ was significantly higher when templates were tethered to the HUH domain for both protein configurations (see FIG. 8). Similarly, ssDNA template integration by HR was significantly higher when templates were tethered to the HUH domain for both protein configurations (see FIGS. 8 and Table 8). Integration rates for the dsDNA oligo were higher than those for ssDNA template apart from the effect of HUH tethering (see FIG. 9). In concordance with the indel rates, the C-terminal fusion protein exhibited improved activity compared to the N-terminal fusion protein for integrating the ds oligo, even though this difference was not statistically significant. Also, in line with the findings in the indel rates, targeted integrations of the ds oligo were adversely affected by tethering the ssDNA template to the fusion proteins. In general, NHEJ-mediated integrations of either the ssDNA or dsDNA oligonucleotides showed close correlation with chromosome cutting rates.

TABLE 8

P values for the ssDNA HR dataset with pairwise comparisons among treatments 1 to 16 using random z test (z = δ/δ_SE).

| | Tr 1 | Tr 2 | Tr 3 | Tr 4 | Tr 5 | Tr 6 | Tr 7 | Tr 8 |
|---|---|---|---|---|---|---|---|---|
| Tr 1 | | | | | | | | |
| Tr 2 | $5.9*10^{-05}$ ‡ | | | | | | | |
| Tr 3 | $1.8*10^{-09}$ ‡ | $2.4*10^{-01}$ | | | | | | |
| Tr 4 | $1.2*10^{-14}$ ‡ | $3.5*10^{-10}$ ‡ | $7.0*10^{-06}$ ‡ | | | | | |
| Tr 5 | $4.8*10^{-07}$ ‡ | $2.1*10^{-59}$ ‡ | $1.9*10^{-38}$ ‡ | $1.8*10^{-35}$ ‡ | | | | |
| Tr 6 | $9.1*10^{-15}$ ‡ | $6.0*10^{-01}$ | $1.6*10^{-04}$ ‡ | $3.6*10^{-04}$ ‡ | $1.1*10^{-67}$ ‡ | | | |
| Tr 7 | $4.1*10^{-01}$ | $5.4*10^{-46}$‡ | $1.6*10^{-06}$ ‡ | $5.5*10^{-197}$ ‡ | $4.2*10^{-09}$ ‡ | $8.1*10^{-11}$ ‡ | | |
| Tr 8 | $2.5*10^{-08}$ ‡ | $7.2*10^{-06}$ ‡ | $3.7*10^{-05}$ ‡ | $1.6*10^{-03}$ ‡ | $1.3*10^{-18}$ ‡ | $3.5*10^{-05}$ ‡ | $4.9*10^{-16}$ ‡ | |
| Tr 9 | $3.3*10^{-34}$ ‡ | $0.0*10^{-0}$ ‡ | $5.9*10^{-133}$ ‡ | $4.7*10^{-172}$ ‡ | $4.4*10^{-109}$ ‡ | $5.2*10^{-164}$ ‡ | $1.0*10^{-150}$ ‡ | $3.2*10^{-38}$ ‡ |
| Tr 10 | $7.4*10^{-34}$ ‡ | $0.0*10^{-0}$ ‡ | $1.2*10^{-129}$ ‡ | $1.9*10^{-171}$ ‡ | $1.9*10^{-113}$ ‡ | $4.4*10^{-162}$ ‡ | $3.2*10^{-150}$ ‡ | $1.4*10^{-38}$ ‡ |
| Tr 11 | $2.0*10^{-03}$ ‡ | $6.5*10^{-01}$ | $6.1*10^{-01}$ | $1.5*10^{-09}$ ‡ | $1.5*10^{-42}$ ‡ | $4.6*10^{-01}$ | $9.1*10^{-30}$ ‡ | $4.5*10^{-15}$ ‡ |
| Tr 12 | $1.4*10^{-06}$ ‡ | $7.8*10^{-05}$ ‡ | $1.5*10^{-04}$ ‡ | $7.7*10^{-02}$ | $3.1*10^{-35}$ ‡ | $2.1*10^{-04}$ ‡ | $4.6*10^{-12}$ ‡ | $2.1*10^{-01}$ |
| Tr 13 | $2.1*10^{-34}$ ‡ | $0.0*10^{-0}$ ‡ | $2.6*10^{-130}$ ‡ | $1.2*10^{-190}$ ‡ | $3.8*10^{-102}$ ‡ | $5.1*10^{-164}$ ‡ | $3.8*10^{-175}$ ‡ | $2.0*10^{-39}$ ‡ |
| Tr 14 | $8.7*10^{-34}$ ‡ | $0.0*10^{-0}$ ‡ | $8.1*10^{-128}$ ‡ | $4.9*10^{-177}$ ‡ | $6.9*10^{-110}$ ‡ | $1.4*10^{-160}$ ‡ | $1.9*10^{-157}$ ‡ | $5.4*10^{-39}$ ‡ |
| Tr 15 | $3.0*10^{-34}$ ‡ | $0.0*10^{-0}$ ‡ | $2.2*10^{-131}$ ‡ | $5.7*10^{-176}$ ‡ | $1.0*10^{-116}$ ‡ | $1.2*10^{-166}$ ‡ | $7.7*10^{-156}$ ‡ | $5.4*10^{-39}$ ‡ |
| Tr 16 | $5.8*10^{-34}$ ‡ | $0.0*10^{-0}$ ‡ | $3.4*10^{-130}$ ‡ | $8.4*10^{-174}$ ‡ | $6.4*10^{-109}$ ‡ | $1.5*10^{-161}$ ‡ | $4.4*10^{-153}$ ‡ | $1.6*10^{-38}$ ‡ |

| | Tr 9 | Tr 10 | Tr 11 | Tr 12 | Tr 13 | Tr 14 | Tr 15 | Tr 16 |
|---|---|---|---|---|---|---|---|---|
| Tr 1 | | | | | | | | |
| Tr 2 | | | | | | | | |
| Tr 3 | | | | | | | | |
| Tr 4 | | | | | | | | |
| Tr 5 | | | | | | | | |
| Tr 6 | | | | | | | | |
| Tr 7 | | | | | | | | |
| Tr 8 | | | | | | | | |
| Tr 9 | | | | | | | | |
| Tr 10 | $2.0*10^{-01}$ | | | | | | | |
| Tr 11 | $4.1*10^{-258}$ ‡ | $3.6*10^{-261}$ ‡ | | | | | | |
| Tr 12 | $6.4*10^{-64}$ ‡ | $2.1*10^{-65}$ ‡ | $1.0*10^{-06}$ ‡ | | | | | |
| Tr 13 | $6.2*10^{-01}$ | $7.9*10^{-01}$ | $8.9*10^{-282}$ ‡ | $3.5*10^{-64}$ ‡ | | | | |
| Tr 14 | $3.0*10^{-02}$ ‡ | $1.4*10^{-01}$ | $3.1*10^{-267}$ ‡ | $1.4*10^{-65}$ ‡ | $1.1*10^{-01}$ | | | |
| Tr 15 | $8.2*10^{-01}$ | $7.6*10^{-02}$ | $1.5*10^{-273}$ ‡ | $9.2*10^{-66}$ ‡ | $4.5*10^{-01}$ | $5.9*10^{-04}$ ‡ | | |
| Tr 16 | $2.4*10^{-04}$ ‡ | $1.4*10^{-01}$ | $5.8*10^{-260}$ ‡ | $1.2*10^{-64}$ ‡ | $2.9*10^{-01}$ | $8.9*10^{-01}$ | $7.4*10^{-03}$ ‡ | |

‡ indicates P values that are smaller than 0.05 and thus denote significant differences between the corresponding treatments.

Example 6: Compatibility of Viral Replication Prigins from various Species with the FBNYV-HUH Endonuclease Fused to cys-Free LbCas12a Both the Faba bean necrotic yellow virus (FBNYV) and the Porcine circovirus 2 (PCV) belong to the class of Arfiviricetes and carry HUH proteins with conserved structures. Likewise, their replication origins (ori) share the same nonamer core sequence (agtattacc) minimally required for recognition and cleavage. See Vega-Rocha et al., 2007, *Biochemistry* 46: 6201 and Timchenko et al., 1999, *J of Virol.* 73: 10173. The recognition of the FBNYV ori (SEQ IDS NO: 27) and PCV ori (SEQ ID NO: 12) sequences by the Cas12a fusion proteins carrying the FBNYV HUH endonuclease was investigated. Tral ori sequence (SEQ ID NO: 28) from the unrelated HUH relaxase Tral from the bacterial conjugation F plasmid (see Dostal et al., 2011, *Nucleic Acids Res* 39: 2658) and a "mock" ori sequence comprising a 15bp soy fragment similar in size to the PCV2 ori were incorporated as negative controls. The three ori sequences and the mock ori sequence were fused to the 70-nucleotide long ssDNA template and gel shifts assays similar to those described in Example 2 were performed.

Gel-shift assays (see table 6) confirmed that in the presence of cys-free LbCas12a:HUH, the ssDNA templates comprising the FBNYV ori and PCV ori migrated significantly slower than those comprising the Tral ori or the mock ori. The slower migration is indicative of the formation of cys-free LbCas12a:HUH::ssDNA tethered complexes. Gel shift of tethered oligos indicates that ori sequences from PCV and FBNYV are compatible with the HUH protein of FBNYV, while ori from the distant homolog Tral and a similar-sized mock ori are not.

TABLE 9

Gel shift assay to detect compatibility of the HUH(FBNYV) fusion proteins with various ori sequences fused to the ssDNA template.

| Assay type | LbCas12a enzyme | crRNA-TS1 | Ori fused to ssDNA template | Upward shift in ssDNA migration observed |
|---|---|---|---|---|
| Test | Cys-free LbCas12a:HUH | + | PCV ori | Yes |
| Test | HUH:cys-free LbCas12a | + | PCV ori | Yes |
| Control | Cys free LbCas12a | + | PCV ori | No |
| Control | — | – | PCV ori | No |
| Test | Cys-free LbCas12a:HUH | + | FBNYV ori | Yes |
| Test | HUH:cys-free LbCas12a | + | FBNYV ori | Yes |
| Control | Cys free LbCas12a | + | FBNYV ori | No |
| Control | — | – | FBNYV ori | No |
| Control | Cys-free LbCas12a:HUH | + | Tral ori | No |
| Control | HUH:cys-free LbCas12a | + | Tral ori | No |
| Control | Cys free LbCas12a | + | Tral ori | No |
| Control | — | – | Tral ori | No |
| Control | Cys-free LbCas12a:HUH | + | Mock ori | No |
| Control | HUH:cys-free LbCas12a | + | Mock ori | No |
| Control | Cys free LbCas12a | + | Mock ori | No |
| Control | — | – | Mock ori | No |
| Control | Cys-free LbCas12a:HUH | + | — | No |
| Control | HUH:cys-free LbCas12a | + | — | No |
| Control | Cys free LbCas12a | + | — | No |
| Control | — | – | — | No |

"+" indicates presence;
"–" indicates absence.

The invention claimed is:

1. A ribonucleoprotein comprising:
   (a) a recombinant polypeptide comprising:
      (i) an amino acid sequence encoding a cysteine-free (cys-free) Cas12a nuclease comprising an amino acid sequence having at least 95% sequence identity to the amino acid sequence of SEQ ID NO: 1;
      (ii) an amino acid sequence encoding a linker comprising an amino acid sequence at least 93% identical to the amino acid sequence of SEQ ID NO: 3; and
      (iii) an amino acid sequence encoding a HUH nuclease selected from the group consisting of a *faba* bean necrosis yellow virus (FBNYV) HUH endonuclease, a porcine circovirus2 (PCV) HUH endonuclease, a duck circovirus (DCV) HUH endonuclease, a *Streptococcus agalactiae* replication protein RepB (RepB), a Fructobacillus tropaeoli RepB RepBm), an *Escherichia coli* (*E. coli*) conjugation protein TraI (TraI), an *E. coli* mobilization protein A (mMobA), and a *Staphylococcus aureus* nicking enzyme (NES); and
   (b) at least one guide nucleic acid.

2. The ribonucleoprotein of claim 1, wherein the HUH nuclease comprises an amino acid sequence having at least 95% sequence identity to an amino acid sequence selected from the group consisting of SEQ ID NOs: 2 and 14.

3. The ribonucleoprotein of claim 1, wherein the recombinant polypeptide comprises an amino acid sequence at least 95% identical to an amino acid sequence selected from the group consisting of SEQ ID NOs: 20 and 21.

4. The ribonucleoprotein of claim 1, wherein the ribonucleoprotein further comprises at least one template nucleic acid molecule.

5. The ribonucleoprotein of claim 4, wherein the template nucleic acid molecule comprises single-stranded DNA.

6. The ribonucleoprotein of claim 4, wherein the template nucleic acid molecule comprises a nucleic acid sequence encoding an origin of replication (ori) that is capable of hybridizing to the HUH nuclease.

7. The ribonucleoprotein or recombinant nucleic acid of claim 6, wherein the origin of replication comprises SEQ ID NO: 12 or SEQ ID NO: 27.

8. A host cell comprising the ribonucleoprotein of claim 1.

9. The host cell of claim 8, wherein the host cell is a plant cell.

10. A method of generating an edit in a target DNA molecule comprising contacting the target DNA molecule with a ribonucleoprotein, wherein the ribonucleoprotein comprises:
   (a) a recombinant polypeptide comprising:
      (i) an amino acid sequence encoding a cys-free Cas12a nuclease comprising an amino acid sequence having at least 95% sequence identity to the amino acid sequence of SEQ ID NO: 1;
      (ii) an amino acid sequence encoding a linker comprising an amino acid sequence at least 93% identical to the amino acid sequence of SEQ ID NO: 3; and
      (iii) an amino acid sequence encoding a HUH nuclease selected from the group consisting of a *faba* bean necrosis yellow virus (FBNYV) HUH endonuclease, a porcine circovirus2 (PCV) HUH endonuclease, a duck circovirus (DCV) HUH endonuclease, a *Streptococcus agalactiae* replication protein RepB (RepB), a Fructobacillus tropaeoli RepB (RepBm), an *Escherichia coli* conjugation protein TraI (TraI), an *E. coli* mobilization protein A (mMobA), and a *Staphylococcus aureus* nicking enzyme (NES);
   (b) at least one guide nucleic acid targeted to a selected sequence in the target DNA molecule; and
   (c) at least one template nucleic acid molecule that specifically interacts with the HUH nuclease of step (a)(iii),
   wherein the ribonucleoprotein generates at least one edit in the target DNA molecule;
   wherein covalent tethering of the template nucleic acid molecule to the cys-free Cas12a nuclease-HUH nuclease-guide nucleic acid complex promotes genome editing compared to the cys-free Cas12a nuclease alone.

11. A method of generating an edit in a target DNA molecule comprising providing to a cell:
   (a) a recombinant polypeptide comprising:
      (i) an amino acid sequence encoding a cys-free Cas12a nuclease comprising an amino acid sequence having at least 95% sequence identity to the amino acid sequence of SEQ ID NO: 1;
      (ii) an amino acid sequence encoding a linker comprising an amino acid sequence at least 93% identical to the amino acid sequence of SEQ ID NO: 3; and
      (iii) an amino acid sequence encoding a HUH nuclease selected from the group consisting of a *faba* bean necrosis yellow virus (FBNYV) HUH endonuclease, a porcine circovirus2 (PCV) HUH endonuclease, a duck circovirus (DCV) HUH endonuclease, a *Streptococcus agalactiae* replication protein RepB (RepB), a Fructobacillus tropaeoli RepB (RepBm), an *Escherichia coli* conjugation protein TraI (TraI), an *E. coli* mobilization protein A (mMobA), and a

*Staphylococcus aureus* nicking enzyme (NES), or one or more nucleic acid molecules encoding the recombinant polypeptide;

(b) at least one guide nucleic acid targeted to a selected sequence in the target DNA molecule of the cell, or at least one nucleic acid molecule encoding the at least one guide nucleic acid; and (c) at least one template nucleic acid molecule that specifically interacts with the HUH nuclease of step (a)(iii), or at least one nucleic acid molecule encoding the at least one template nucleic acid molecule, wherein the recombinant polypeptide, at least one guide nucleic acid, and at least one template nucleic acid molecule form a ribonucleoprotein, and wherein the ribonucleoprotein generates at least one edit in the target DNA molecule within the cell; wherein covalent tethering of the template nucleic acid molecule to the cys-free Cas12a nuclease-HUH nuclease-guide nucleic acid complex promotes genome editing compared to the cys-free Cas12a nuclease alone.

12. The method of claim 10, wherein the at least one edit comprises a mutation.

13. The method of claim 12, wherein the mutation comprises a site-directed integration.

14. The method of claim 10, wherein the target DNA molecule comprises non-genic DNA.

15. The method of claim 10, wherein the target DNA molecule comprises genic DNA.

16. The method of claim 11, wherein the cell is selected from the group consisting of a corn cell, a soybean cell, a cotton cell, a canola cell, a rice cell, a wheat cell, a sorghum cell, an alfalfa cell, a sugarcane cell, a millet cell, a tomato cell, a potato cell, a cucumber cell, a barley cell, a grass cell, a *Setaria* cell, an *Arabidopsis* cell, an eell-*Escherichia coli* cell, or an algal cell.

17. The method of claim 10, wherein the target DNA molecule is a genomic DNA molecule selected from the group consisting of a nuclear genome DNA molecule, a mitochondrial genome DNA molecule, and a plastid genome DNA molecule.

18. The method of claim 11, wherein the at least one edit comprises a mutation.

19. The method of claim 11 wherein the target DNA molecule comprises non-genic DNA.

20. The method of claim 11, wherein the target DNA molecule comprises genic DNA.

21. The method of claim 11 wherein the target DNA molecule is a genomic DNA molecule selected from the group consisting of a nuclear genome DNA molecule, a mitochondrial genome DNA molecule, and a plastid genome DNA molecule.

* * * * *